(12) United States Patent
Ho et al.

(10) Patent No.: US 11,802,163 B2
(45) Date of Patent: Oct. 31, 2023

(54) CHIMERIC ANTIGEN RECEPTORS TARGETING GLYPICAN-3 OR MESOTHELIN

(71) Applicant: The U.S.A., as represented by the Secretary, Department of Health and Human Services, Bethesda, MD (US)

(72) Inventors: Mitchell Ho, Urbana, MD (US); Nan Li, Laurel, MD (US); Dan Li, Bethesda, MD (US)

(73) Assignee: The U.S.A., as represented by the Secretary, Department of Health and Human Services, Bethesda, MD (US)

( * ) Notice: Subject to any disclaimer, the term of this patent is extended or adjusted under 35 U.S.C. 154(b) by 540 days.

(21) Appl. No.: 16/762,459

(22) PCT Filed: Nov. 7, 2018

(86) PCT No.: PCT/US2018/059645
§ 371 (c)(1),
(2) Date: May 7, 2020

(87) PCT Pub. No.: WO2019/094482
PCT Pub. Date: May 16, 2019

(65) Prior Publication Data
US 2021/0371542 A1  Dec. 2, 2021

Related U.S. Application Data

(60) Provisional application No. 62/584,421, filed on Nov. 10, 2017.

(51) Int. Cl.
| | | |
|---|---|---|
| C07K 16/30 | (2006.01) | |
| A61P 35/00 | (2006.01) | |
| A61K 35/17 | (2015.01) | |
| C07K 14/725 | (2006.01) | |
| C07K 14/705 | (2006.01) | |
| C07K 14/71 | (2006.01) | |
| C07K 14/715 | (2006.01) | |
| A61K 39/00 | (2006.01) | |

(52) U.S. Cl.
CPC ............ *C07K 16/303* (2013.01); *A61K 35/17* (2013.01); *A61P 35/00* (2018.01); *C07K 14/7051* (2013.01); *C07K 14/70517* (2013.01); *C07K 14/70521* (2013.01); *C07K 14/70578* (2013.01); *C07K 14/71* (2013.01); *C07K 14/7153* (2013.01); *A61K 2039/505* (2013.01); *C07K 2317/569* (2013.01); *C07K 2317/622* (2013.01); *C07K 2319/02* (2013.01); *C07K 2319/03* (2013.01)

(58) Field of Classification Search
CPC ................ C07K 14/7051; C07K 14/71; A61K 2039/505
See application file for complete search history.

(56) References Cited

U.S. PATENT DOCUMENTS

| | | |
|---|---|---|
| 8,906,682 B2 | 12/2014 | June et al. |
| 9,272,002 B2 | 3/2016 | Powell, Jr. et al. |
| 9,394,368 B2 | 7/2016 | Brogdon et al. |
| 9,402,865 B2 | 8/2016 | Powell et al. |
| 9,446,105 B2 | 9/2016 | Powell, Jr. |
| 9,447,194 B2 | 9/2016 | Jensen |
| 9,573,988 B2 | 2/2017 | Brogdon et al. |
| 9,580,685 B2 | 2/2017 | Jensen |
| 2015/0139943 A1 | 5/2015 | Campana et al. |
| 2016/0215261 A1 | 7/2016 | Li et al. |
| 2016/0333114 A1 | 11/2016 | Williams et al. |
| 2017/0081405 A1 | 3/2017 | Adusumilli et al. |

FOREIGN PATENT DOCUMENTS

| | | |
|---|---|---|
| CN | 104780939 A | 7/2015 |
| CN | 105949324 A | 9/2016 |
| EP | 2 995 682 | 3/2016 |
| WO | WO 2011/056894 | 5/2011 |
| WO | WO 2012/145469 | 10/2012 |
| WO | WO 2013/070468 | 5/2013 |
| WO | WO 2013/123061 | 8/2013 |
| WO | WO 2013/181543 | 12/2013 |
| WO | WO 2014/031476 | 2/2014 |
| WO | WO 2014/031687 A1 | 2/2014 |
| WO | WO 2015/157391 | 10/2015 |
| WO | WO 2015/157432 | 10/2015 |

(Continued)

OTHER PUBLICATIONS

Bosse et al., "Identification of GPC2 as an Oncoprotein and Candidate Immunotherapeutic Target in High-Risk Neuroblastoma," *Cancer Cell* 32:295-309, 2017.

Baumhoer et al., "Glypican 3 Expression in Human Noneoplastic, Preneoplastic, and Neoplastic Tissues," *Am. J. Clin. Pathol.*, vol. 129:899-906, 2008.

EBI Accession No. BAE63125, Dec. 20, 2012.

(Continued)

*Primary Examiner* — Elly-Gerald Stoica
(74) *Attorney, Agent, or Firm* — KLARQUIST SPARKMAN, LLP

(57) ABSTRACT

Nucleic acid constructs encoding a chimeric antigen receptor (CAR) and a truncated human epidermal growth factor receptor (huEGFRt) are described. The encoded CARs include a tumor antigen-specific monoclonal antibody, such as a glypican-3 (GPC3)-specific, a GPC2-specific or a mesothelin-specific monoclonal antibody, fused to a CD8α hinge region, a CD8α transmembrane region, a 4-1BB co-stimulatory domain and a CD3ζ signaling domain. Isolated host cells, such as isolated T cells that co-express the disclosed CARs and huEGFRt are also described. T cells transduced with the disclosed CAR constructs can be used for cancer immunotherapy.

36 Claims, 40 Drawing Sheets
Specification includes a Sequence Listing.

(56) References Cited

FOREIGN PATENT DOCUMENTS

| WO | WO 2016/040441 | 3/2016 |
|---|---|---|
| WO | WO 2017/027291 | 2/2017 |
| WO | WO 2017/044699 | 3/2017 |
| WO | WO 2018/026533 | 2/2018 |

OTHER PUBLICATIONS

EBI Accession No. BAS65485, Oct. 24, 2013.
EBI Accession No. BAS65487, Oct. 24, 2013.
EBI Accession No. BAS65491, Oct. 24, 2013.
EBI Accession No. BBA60241, Jan. 30, 2014.
Feng et al., "Therapeutically Targeting Glypican-3 via a Conformation-Specific Single-Domain Antibody in Hepatocellular Carcinoma," *Proc. Nat. Acad. Sci.*, vol. 110:E1083-E1091, 2013.
Ho et al., "Glypican-3: A New Target for Cancer Immunotherapy," *Eur. J. Cancer*, vol. 47:333-338, 2011.
International Search Report and Written Opinion for PCT Application No. PCT/US2018/059645, dated Apr. 5, 2019.
Kowolik et al., "CD28 Costimulation Provided through a CD19-Specific Chimeric Antigen Receptor Enhances in vivo Persistence and Antitumor Efficacy of Adoptively Transferred T Cells," *Cancer Res.*, vol. 66:10995-11004, 2006.
Li et al., "Therapeutically Targeting Glypican-2 via Single-Domain Antibody-Based Chimeric Antigen Receptors and Immunotoxins in Neuroblastoma," *Proc. Nat. Acad. Sci.*, vol. 114: E6623-E6631, 2017.
Saikali et al., "Expression of Glypican 3 (GPC3) in Embryonal Tumors," *Int. J. Cancer (Pred. Oncol.)*, vol. 89:418-422, 2000.
Wang et al., "A Transgene-Encoded Cell Surface Polypeptide for Selection, in Vivo Tracking, and Ablation of Engineered Cells," *Blood*, vol. 118:1255-1263, 2011.
Wee et al., "Epidermal Growth Factor Receptor Cell Proliferation Signaling Pathways," *Cancers*, vol. 9:52, 2017.
Yu et al., "Chimeric Antigen Receptor T Cells: A Novel Therapy for Solid Tumors," *J. Hematol. Oncol.*, vol. 10:78-91, 2017.
Zhang et al., "Humanization of High-Affinity Antibodies Targeting Glypican-3 in Hepatocellular Carcinoma," *Sci. Rep.*, vol. 6:33878, 2016.
Tomar et al., "Development of Highly Effective Anti-Mesothelin hYP218 Chimeric Antigen Receptor T Cells With Increased Tumor Infiltration and Persistence for Treating Solid Tumors," *Mol Cancer Ther* 21:1195-1206, 2022.

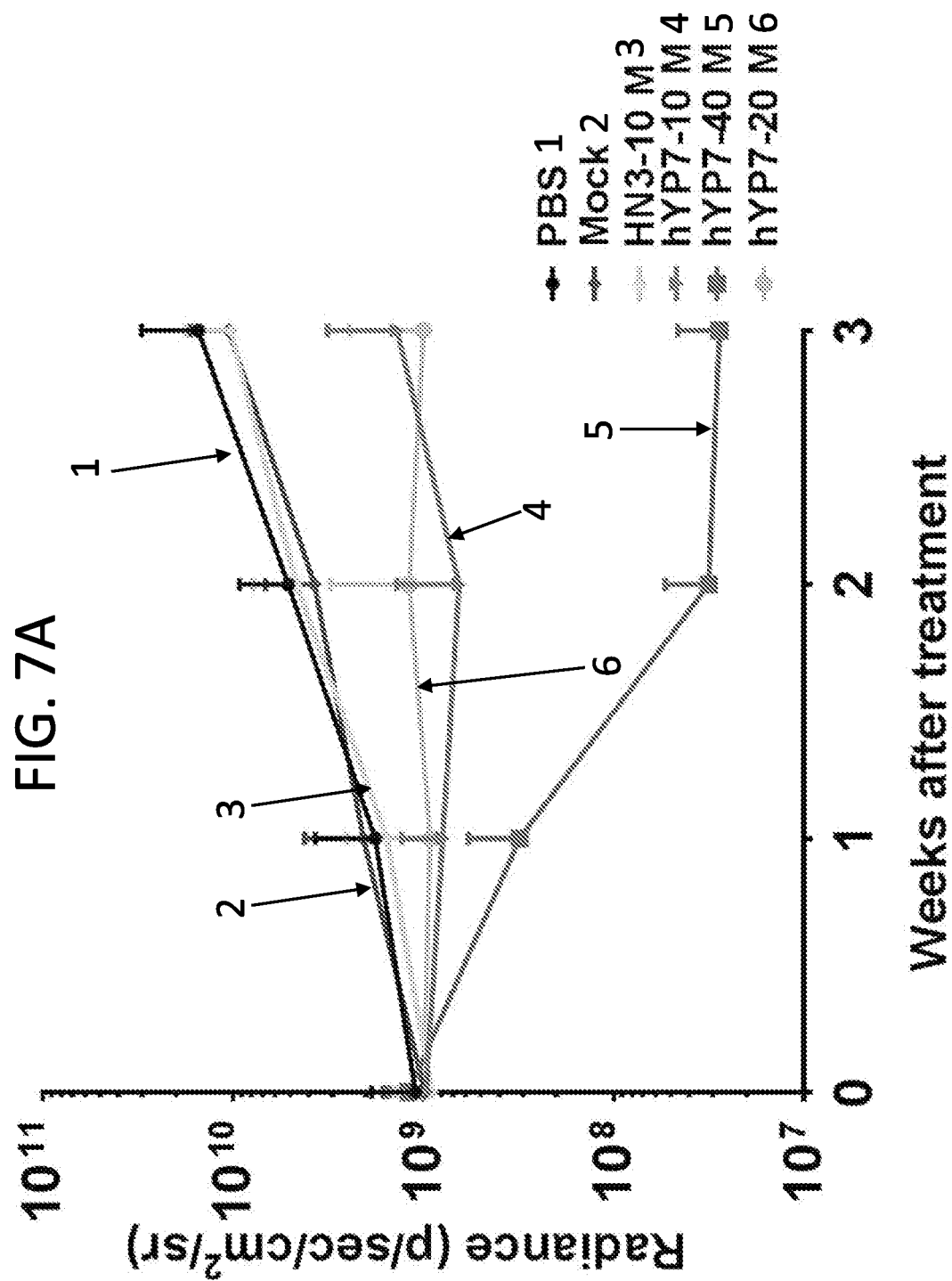

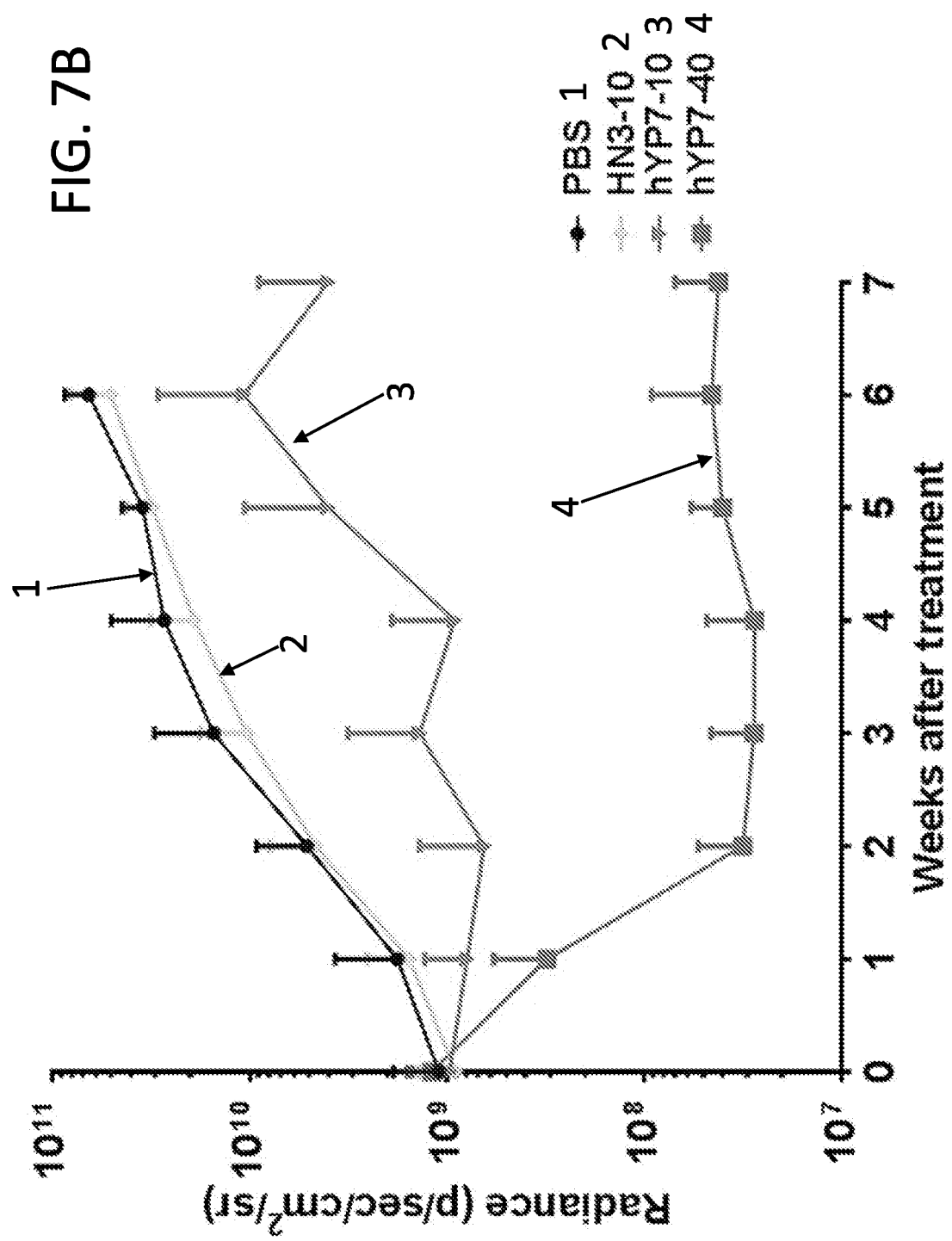

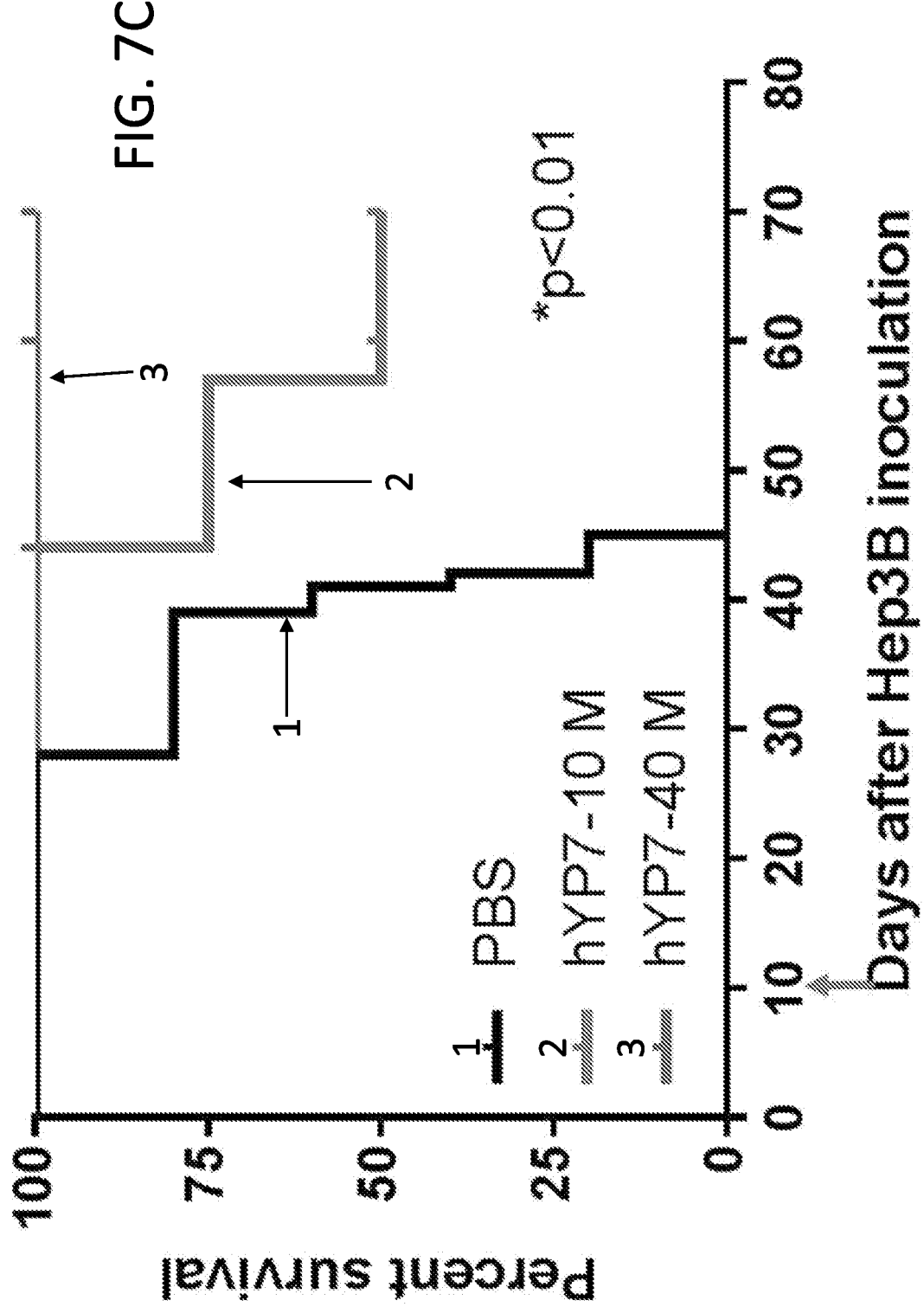

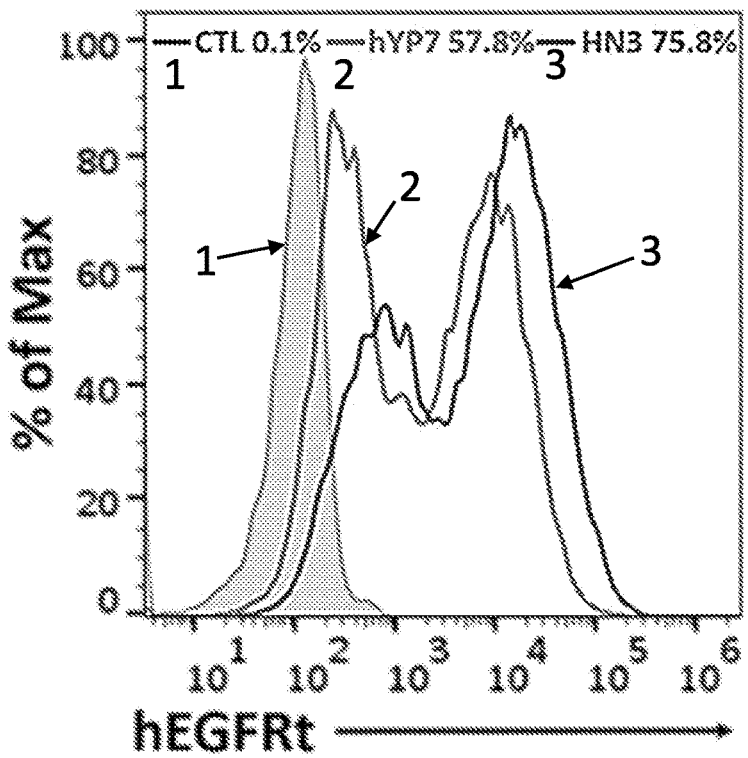
FIG. 10C
FIG. 10D
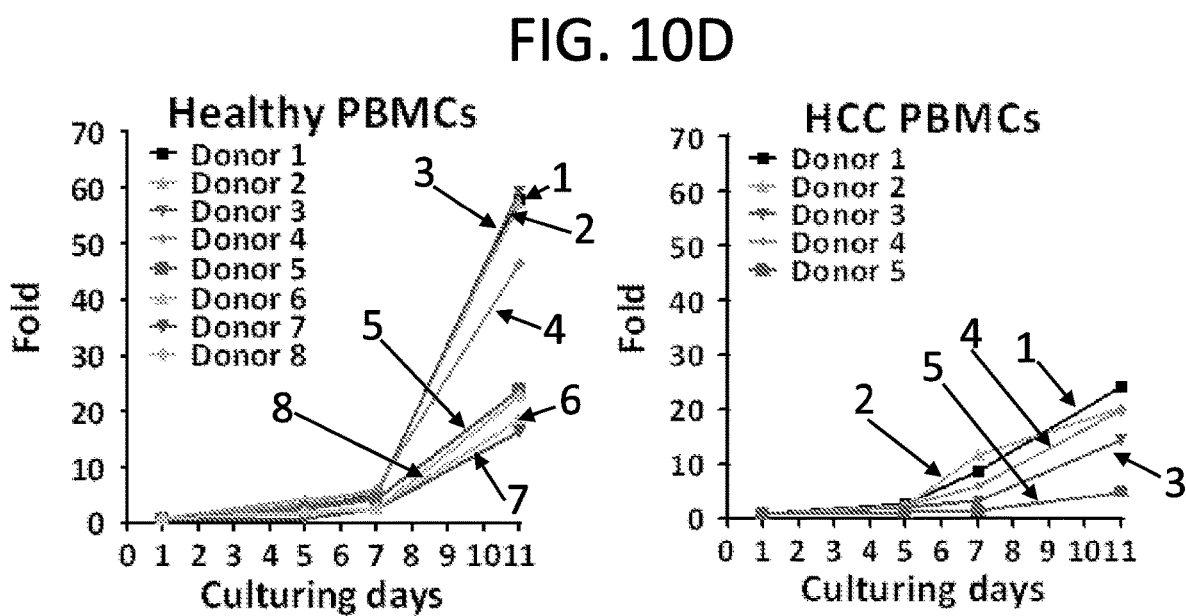

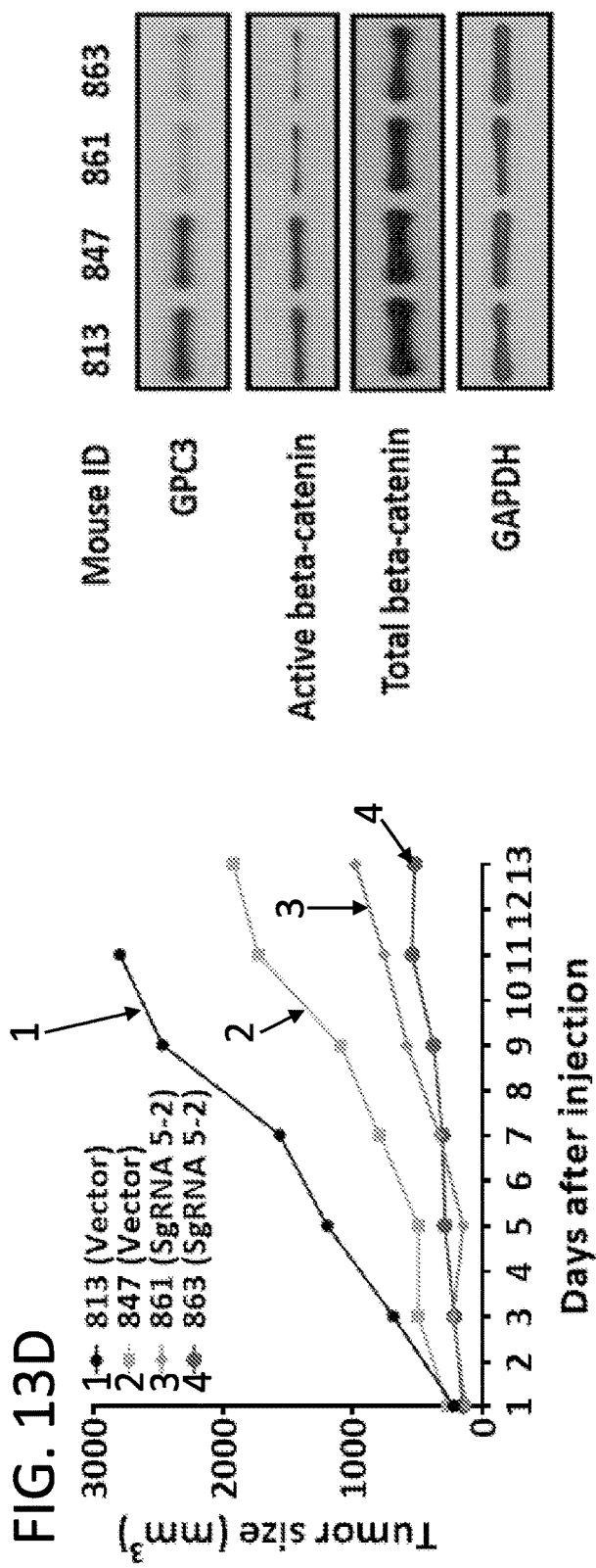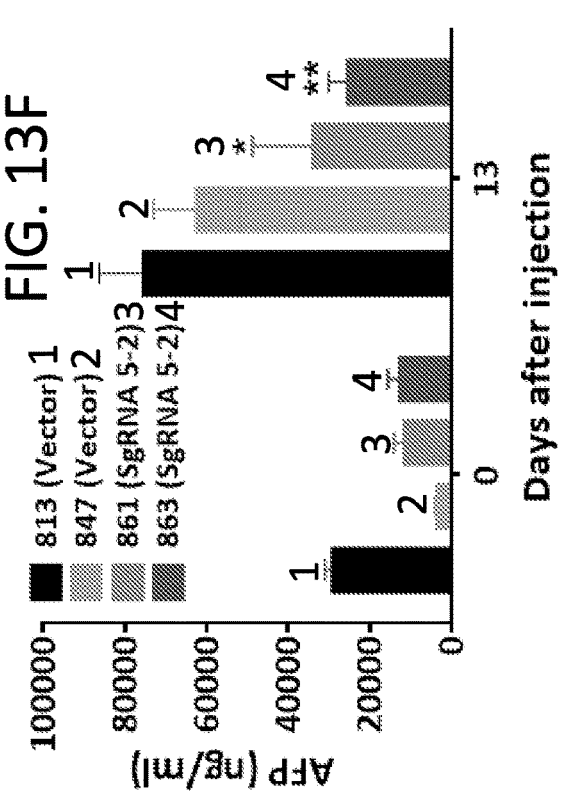

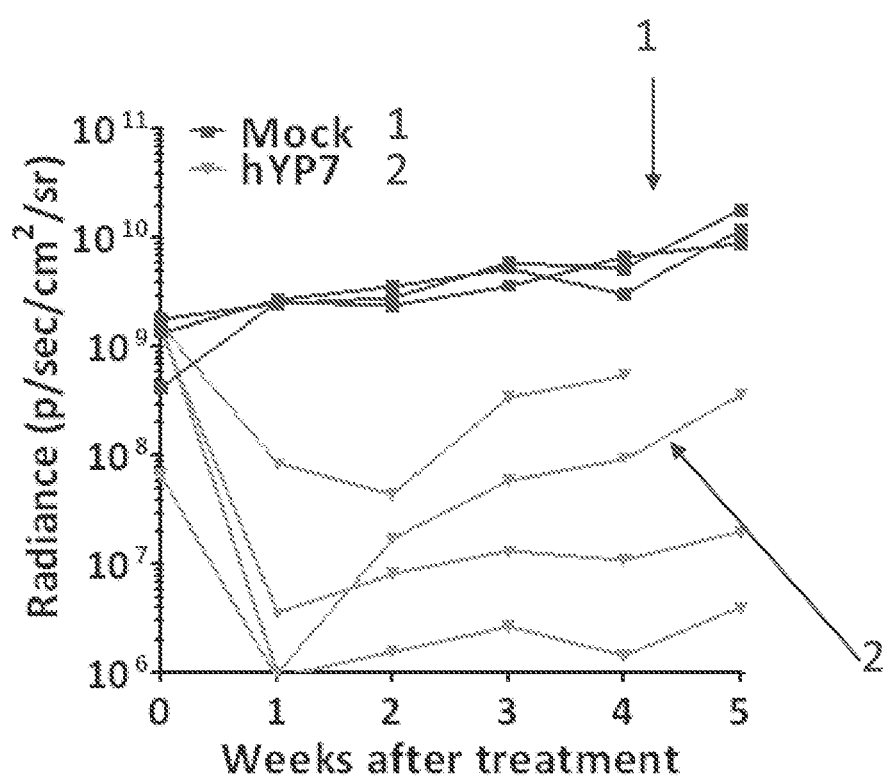

```
                         SEQUENCE LISTING

<160> NUMBER OF SEQ ID NOS: 51

<210> SEQ ID NO 1
<211> LENGTH: 66
<212> TYPE: DNA
<213> ORGANISM: Artificial Sequence
<220> FEATURE:
<223> OTHER INFORMATION: Synthetic polynucleotide (GMCSFRss)

<400> SEQUENCE: 1
atgcttctcc tggtgacaag ccttctgctc tgtgagttac cacacccagc attcctcctg      60
atccca                                                                66

<210> SEQ ID NO 2
<211> LENGTH: 22
<212> TYPE: PRT
<213> ORGANISM: Artificial Sequence
<220> FEATURE:
<223> OTHER INFORMATION: Synthetic peptide (GMCSFRss)

<400> SEQUENCE: 2

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 3
<211> LENGTH: 135
<212> TYPE: DNA
<213> ORGANISM: Artificial Sequence
<220> FEATURE:
<223> OTHER INFORMATION: Synthetic polynucleotide (CD8alpha hinge)

<400> SEQUENCE: 3
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg     120
gacttcgcct gtgac                                                     135

<210> SEQ ID NO 4
<211> LENGTH: 45
<212> TYPE: PRT
<213> ORGANISM: Artificial Sequence
<220> FEATURE:
<223> OTHER INFORMATION: Synthetic polypeptide (CD8alpha hinge)
```

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 5
<211> LENGTH: 63
<212> TYPE: DNA
<213> ORGANISM: Artificial Sequence
<220> FEATURE:
<223> OTHER INFORMATION: Synthetic polynucleotide (CD8alpha TM)

<400> SEQUENCE: 5
atctacatct gggcgccctt ggccgggact tgtggggtcc ttctcctgtc actggttatc    60
acc                                                                 63

<210> SEQ ID NO 6
<211> LENGTH: 21
<212> TYPE: PRT
<213> ORGANISM: Artificial Sequence
<220> FEATURE:
<223> OTHER INFORMATION: Synthetic polypeptide (CD8alpha TM)

<400> SEQUENCE: 6

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 7
<211> LENGTH: 126
<212> TYPE: DNA
<213> ORGANISM: Artificial Sequence
<220> FEATURE:
<223> OTHER INFORMATION: Synthetic polynucleotide (4-1BB)

<400> SEQUENCE: 7
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126

<210> SEQ ID NO 8
<211> LENGTH: 42
<212> TYPE: PRT
<213> ORGANISM: Artificial Sequence
<220> FEATURE:
<223> OTHER INFORMATION: Synthetic polypeptide (4-1BB)

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 9
<211> LENGTH: 336

```
<212> TYPE: DNA
<213> ORGANISM: Artificial Sequence
<220> FEATURE:
<223> OTHER INFORMATION: Synthetic polynucleotide (CD3zeta signaling
      domain)

<400> SEQUENCE: 9
agagtgaagt tcagcaggag cgcagacgcc cccgcgtacc agcagggcca gaaccagctc     60
tataacgagc tcaatctagg acgaagagag gagtacgatg ttttggacaa gagacgtggc    120
cgggaccctg agatggggggg aaagccgaga aggaagaacc ctcaggaagg cctgtacaat    180
gaactgcaga agataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgc                              336

<210> SEQ ID NO 10
<211> LENGTH: 112
<212> TYPE: PRT
<213> ORGANISM: Artificial Sequence
<220> FEATURE:
<223> OTHER INFORMATION: Synthetic polypeptide (CD3zeta signaling
      domain)

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 11
<211> LENGTH: 54
<212> TYPE: DNA
<213> ORGANISM: Artificial Sequence
<220> FEATURE:
<223> OTHER INFORMATION: Synthetic polynucleotide (T2A)

<400> SEQUENCE: 11
gagggcagag gaagtcttct aacatgcggt gacgtggagg agaatcccgg ccct           54

<210> SEQ ID NO 12
<211> LENGTH: 18
<212> TYPE: PRT
<213> ORGANISM: Artificial Sequence
<220> FEATURE:
<223> OTHER INFORMATION: Synthetic peptide (T2A)

<400> SEQUENCE: 12

Glu Gly Arg Gly Ser Leu Leu Thr Cys Gly Asp Val Glu Glu Asn Pro
1               5                   10                  15

Gly Pro
```

<210> SEQ ID NO 13
<211> LENGTH: 1005
<212> TYPE: DNA
<213> ORGANISM: Artificial Sequence
<220> FEATURE:
<223> OTHER INFORMATION: Synthetic polynucleotide (huEGFRt)

<400> SEQUENCE: 13

```
cgcaaagtgt gtaacggaat aggtattggt gaatttaaag actcactctc cataaatgct    60
acgaatatta aacacttcaa aaactgcacc tccatcagtg gcgatctcca catcctgccg   120
gtggcattta ggggtgactc cttcacacat actcctcctc tggatccaca ggaactggat   180
attctgaaaa ccgtaaagga atcacaggg tttttgctga ttcaggcttg gcctgaaaac   240
aggacggacc tccatgcctt tgagaaccta gaaatcatac gcggcaggac caagcaacat   300
ggtcagtttt ctcttgcagt cgtcagcctg aacataacat ccttgggatt acgctccctc   360
aaggagataa gtgatggaga tgtgataatt tcaggaaaca aaaatttgtg ctatgcaaat   420
acaataaact ggaaaaaact gtttgggacc tccggtcaga aaaccaaaat tataagcaac   480
agaggtgaaa acagctgcaa ggccacaggc caggtctgcc atgccttgtg ctcccccgag   540
ggctgctggg gcccggagcc cagggactgc gtctcttgcc ggaatgtcag ccgaggcagg   600
gaatgcgtgg acaagtgcaa ccttctggag ggtgagccaa gggagtttgt ggagaactct   660
gagtgcatac agtgccaccc agagtgcctg cctcaggcca tgaacatcac ctgcacagga   720
cggggaccag acaactgtat ccagtgtgcc cactacattg acggccccca ctgcgtcaag   780
acctgcccgg caggagtcat gggagaaaac aacaccctgg tctggaagta cgcagacgcc   840
ggccatgtgt gccacctgtg ccatccaaac tgcacctacg gatgcactgg gccaggtctt   900
gaaggctgtc caacgaatgg gcctaagatc ccgtccatcg ccactgggat ggtgggggcc   960
ctcctcttgc tgctggtggt ggccctgggg atcggcctct tcatg             1005
```

<210> SEQ ID NO 14
<211> LENGTH: 335
<212> TYPE: PRT
<213> ORGANISM: Artificial Sequence
<220> FEATURE:
<223> OTHER INFORMATION: Synthetic polypeptide (huEGFRt)

<400> SEQUENCE: 14

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
```

```
                    130                 135                 140
Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335
```

<210> SEQ ID NO 15
<211> LENGTH: 2601
<212> TYPE: DNA
<213> ORGANISM: Artificial Sequence
<220> FEATURE:
<223> OTHER INFORMATION: Synthetic construct (pMH289)

<400> SEQUENCE: 15

| | | | | | |
|---|---|---|---|---|---|
| atgcttctcc | tggtgacaag | ccttctgctc | tgtgagttac | cacacccagc | attcctcctg | 60 |
| atcccacata | tggaggtgca | gcttgttgag | tctggtggag | gattggtgca | gcctggaggg | 120 |
| tcattgagac | tctcatgtgc | agcctctgga | ttcaccttca | ataagaatgc | catgaattgg | 180 |
| gtccgccagg | ctccaggaaa | gggtttggaa | tgggttggcc | gcataagaaa | taaaactaat | 240 |
| aattatgcaa | catattatgc | cgattcagtg | aaagccaggt | ttaccatctc | cagagatgat | 300 |
| tcaaagaact | cactctatct | gcaaatgaac | agcttgaaaa | ccgaggacac | agccgtgtac | 360 |
| tattgtgtgg | ctggtaactc | gtttgcttac | tggggccaag | ggactctggt | cactgtctct | 420 |
| gcaggcggag | gcggatcagg | tggtggcgga | tctggaggtg | gcggaagcga | cattgtgatg | 480 |
| acccagtctc | cagactccct | agctgtgtca | ctgggagaga | gggccactat | caactgcaag | 540 |
| tccagtcaga | gccttttata | tagcagcaat | caaaagaact | acttggcctg | gtaccaacag | 600 |
| aaaccagggc | agcctcctaa | actgctgatt | tactgggcat | ccagtaggga | atctggggtc | 660 |
| cctgatcgct | tcagtggcag | tggatctggg | acagatttca | ctctcaccat | cagcagtctg | 720 |
| caggctgaag | acgtggcagt | ttattactgt | cagcaatatt | ataactatcc | gctcacgttc | 780 |
| ggtcagggga | ccaagttgga | gatcaaaact | gtaccacga | cgccagcgcc | gcgaccacca | 840 |
| acaccggcgc | ccaccatcgc | gtcgcagccc | ctgtccctgc | gcccagaggc | gtgccggcca | 900 |
| gcggcggggg | gcgcagtgca | cacgaggggg | ctggacttcg | cctgtgacat | ctacatctgg | 960 |

```
gcgcccttgg ccgggacttg tggggtcctt ctcctgtcac tggttatcac caaacggggc    1020
agaaagaaac tcctgtatat attcaaacaa ccatttatga ccagtacaa aactactcaa    1080 gaggaagatg gctgtagctg ccgatttcca gaagaagaag aaggaggatg tgaactgaga    1140
gtgaagttca gcaggagcgc agacgccccc gcgtaccagc agggccagaa ccagctctat    1200
aacgagctca atctaggacg aagagaggag tacgatgttt tggacaagag acgtggccgg    1260
gaccctgaga tgggggggaaa gccgagaagg aagaaccctc aggaaggcct gtacaatgaa    1320
ctgcagaaag ataagatggc ggaggcctac agtgagattg ggatgaaagg cgagcgccgg    1380
aggggcaagg ggcacgatgg cctttaccag ggtctcagta cagccaccaa ggacacctac    1440 gacgccttc acatgcaggc cctgcccct cgcgagggca gaggaagtct tctaacatgc    1500
ggtgacgtgg aggagaatcc cggccctatg cttctcctgg tgacaagcct tctgctctgt    1560
gagttaccac acccagcatt cctcctgatc ccacgcaaag tgtgtaacgg aataggtatt    1620
ggtgaattta aagactcact ctccataaat gctacgaata ttaaacactt caaaaactgc    1680
acctccatca gtggcgatct ccacatcctg ccggtggcat ttagggggtga ctccttcaca    1740 catactcctc ctctggatcc acaggaactg gatattctga aaaccgtaaa ggaaatcaca    1800 gggttttgc tgattcaggc ttggcctgaa acaggacgg acctccatgc ctttgagaac    1860
ctagaaatca tacgcggcag gaccaagcaa catggtcagt tttctcttgc agtcgtcagc    1920
ctgaacataa catccttggg attacgctcc ctcaaggaga taagtgatgg agatgtgata    1980
atttcaggaa acaaaaattt gtgctatgca aatacaataa actggaaaaa actgtttggg    2040
acctccggtc agaaaaccaa aattataagc aacagaggtg aaaacagctg caaggccaca    2100
ggccaggtct gccatgcctt gtgctccccc gagggctgct ggggcccgga gcccagggac    2160
tgcgtctctt gccggaatgt cagccgaggc agggaatgcg tggacaagtg caacttcctg    2220
gagggtgagc caagggagtt tgtggagaac tctgagtgca tacagtgcca cccagagtgc    2280
ctgcctcagg ccatgaacat cacctgcaca ggacggggac cagacaactg tatccagtgt    2340
gcccactaca ttgacggccc ccactgcgtc aagacctgcc cggcaggagt catgggagaa    2400
aacaacaccc tggtctggaa gtacgcagac gccggccatg tgtgccacct gtgccatcca    2460
aactgcacct acggatgcac tgggccaggt cttgaaggct gtccaacgaa tgggcctaag    2520
atcccgtcca tcgccactgg gatggtgggg gccctcctct tgctgctggt ggtggccctg    2580
gggatcggcc tcttcatgtg a                                              2601
```

<210> SEQ ID NO 16
<211> LENGTH: 866
<212> TYPE: PRT
<213> ORGANISM: Artificial Sequence
<220> FEATURE:
<223> OTHER INFORMATION: Synthetic polypeptide (hYP7-CAR)

<400> SEQUENCE: 16

```
Met Leu Leu Leu Val Thr Ser Leu Leu Leu Cys Glu Leu Pro His Pro
 1               5                  10                  15

Ala Phe Leu Leu Ile Pro His Met Glu Val Gln Leu Val Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Asn Lys Asn Ala Met Asn Trp Val Arg Gln Ala
    50                  55                  60
```

-continued

```
Pro Gly Lys Gly Leu Glu Trp Val Gly Arg Ile Arg Asn Lys Thr Asn
 65                  70                  75                  80

Asn Tyr Ala Thr Tyr Tyr Ala Asp Ser Val Lys Ala Arg Phe Thr Ile
                 85                  90                  95

Ser Arg Asp Asp Ser Lys Asn Ser Leu Tyr Leu Gln Met Asn Ser Leu
            100                 105                 110

Lys Thr Glu Asp Thr Ala Val Tyr Tyr Cys Val Ala Gly Asn Ser Phe
        115                 120                 125

Ala Tyr Trp Gly Gln Gly Thr Leu Val Thr Val Ser Ala Gly Gly Gly
    130                 135                 140

Gly Ser Gly Gly Gly Gly Ser Gly Gly Gly Gly Ser Asp Ile Val Met
145                 150                 155                 160

Thr Gln Ser Pro Asp Ser Leu Ala Val Ser Leu Gly Glu Arg Ala Thr
                165                 170                 175

Ile Asn Cys Lys Ser Ser Gln Ser Leu Leu Tyr Ser Ser Asn Gln Lys
            180                 185                 190

Asn Tyr Leu Ala Trp Tyr Gln Gln Lys Pro Gly Gln Pro Pro Lys Leu
        195                 200                 205

Leu Ile Tyr Trp Ala Ser Ser Arg Glu Ser Gly Val Pro Asp Arg Phe
    210                 215                 220

Ser Gly Ser Gly Ser Gly Thr Asp Phe Thr Leu Thr Ile Ser Ser Leu
225                 230                 235                 240

Gln Ala Glu Asp Val Ala Val Tyr Tyr Cys Gln Gln Tyr Tyr Asn Tyr
                245                 250                 255

Pro Leu Thr Phe Gly Gln Gly Thr Lys Leu Glu Ile Lys Thr Ser Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Glu Gly Arg Gly Ser
```

```
                        485                 490                 495
Leu Leu Thr Cys Gly Asp Val Glu Glu Asn Pro Gly Pro Met Leu Leu
                500                 505                 510
Leu Val Thr Ser Leu Leu Cys Glu Leu Pro His Pro Ala Phe Leu
            515                 520                 525
Leu Ile Pro Arg Lys Val Cys Asn Gly Ile Gly Ile Gly Glu Phe Lys
            530                 535                 540
Asp Ser Leu Ser Ile Asn Ala Thr Asn Ile Lys His Phe Lys Asn Cys
545                 550                 555                 560
Thr Ser Ile Ser Gly Asp Leu His Ile Leu Pro Val Ala Phe Arg Gly
                565                 570                 575
Asp Ser Phe Thr His Thr Pro Pro Leu Asp Pro Gln Glu Leu Asp Ile
                580                 585                 590
Leu Lys Thr Val Lys Glu Ile Thr Gly Phe Leu Leu Ile Gln Ala Trp
            595                 600                 605
Pro Glu Asn Arg Thr Asp Leu His Ala Phe Glu Asn Leu Glu Ile Ile
            610                 615                 620
Arg Gly Arg Thr Lys Gln His Gly Gln Phe Ser Leu Ala Val Val Ser
625                 630                 635                 640
Leu Asn Ile Thr Ser Leu Gly Leu Arg Ser Leu Lys Glu Ile Ser Asp
                645                 650                 655
Gly Asp Val Ile Ile Ser Gly Asn Lys Asn Leu Cys Tyr Ala Asn Thr
                660                 665                 670
Ile Asn Trp Lys Lys Leu Phe Gly Thr Ser Gly Gln Lys Thr Lys Ile
            675                 680                 685
Ile Ser Asn Arg Gly Glu Asn Ser Cys Lys Ala Thr Gly Gln Val Cys
            690                 695                 700
His Ala Leu Cys Ser Pro Glu Gly Cys Trp Gly Pro Glu Pro Arg Asp
705                 710                 715                 720
Cys Val Ser Cys Arg Asn Val Ser Arg Gly Arg Glu Cys Val Asp Lys
                725                 730                 735
Cys Asn Leu Leu Glu Gly Glu Pro Arg Glu Phe Val Glu Asn Ser Glu
                740                 745                 750
Cys Ile Gln Cys His Pro Glu Cys Leu Pro Gln Ala Met Asn Ile Thr
            755                 760                 765
Cys Thr Gly Arg Gly Pro Asp Asn Cys Ile Gln Cys Ala His Tyr Ile
            770                 775                 780
Asp Gly Pro His Cys Val Lys Thr Cys Pro Ala Gly Val Met Gly Glu
785                 790                 795                 800
Asn Asn Thr Leu Val Trp Lys Tyr Ala Asp Ala Gly His Val Cys His
                805                 810                 815
Leu Cys His Pro Asn Cys Thr Tyr Gly Cys Thr Gly Pro Gly Leu Glu
                820                 825                 830
Gly Cys Pro Thr Asn Gly Pro Lys Ile Pro Ser Ile Ala Thr Gly Met
            835                 840                 845
Val Gly Ala Leu Leu Leu Leu Leu Val Val Ala Leu Gly Ile Gly Leu
            850                 855                 860
Phe Met
865

<210> SEQ ID NO 17
<211> LENGTH: 2214
<212> TYPE: DNA
<213> ORGANISM: Artificial Sequence
```

<220> FEATURE:
<223> OTHER INFORMATION: Synthetic construct (pMH288)

<400> SEQUENCE: 17

```
atgcttctcc tggtgacaag ccttctgctc tgtgagttac cacacccagc attcctcctg      60
atcccacata tgcaggtgca gctggtgcag tctgggggag gcttggtaca gcctggaggg     120
tccctgagac tctcctgtgc agcctcttat ttcgatttcg attcttatga aatgagctgg     180
gtccgccagg ctccagggaa gggcctagag tggattggga gtatctatca tagtgggagc     240
acctactaca acccgtccct caagagtcga gtcaccatct ccagagacaa ttccaagaac     300
acgctgtatc tgcaaatgaa caccctgaga gccgaggaca cagccacgta ttactgtgcg     360
agagtaaata tggaccgatt tgactactgg ggccagggaa ccctggtcac cgtctcctca     420
actagtacca cgacgccagc gccgcgacca ccaacaccgg cgccaccat cgcgtcgcag     480
cccctgtccc tgcgcccaga ggcgtgccgg ccagcggcgg ggggcgcagt gcacacgagg     540
gggctggact cgcctgtga catctacatc tgggcgccct tggccgggac ttgtggggtc     600
cttctcctgt cactggttat caccaaacgg ggcagaaaga aactcctgta tatattcaaa     660
caaccattta tgagaccagt acaaactact caagaggaag atggctgtag ctgccgattt     720
ccagaagaag aagaaggagg atgtgaactg agagtgaagt tcagcaggag cgcagacgcc     780
cccgcgtacc agcagggcca gaaccagctc tataacgagc tcaatctagg acgaagagag     840
gagtacgatg ttttggacaa gagacgtggc cgggaccctg atggggggg aaagccgaga     900
aggaagaacc ctcaggaagg cctgtacaat gaactgcaga agataagat ggcggaggcc     960
tacagtgaga ttgggatgaa aggcgagcgc cggaggggca aggggcacga tggcctttac    1020
cagggtctca gtacagccac caaggacacc tacgacgccc ttcacatgca ggccctgccc    1080
cctcgcgagg gcagaggaag tcttctaaca tgcggtgacg tggaggagaa tcccggccct    1140
atgcttctcc tggtgacaag ccttctgctc tgtgagttac cacacccagc attcctcctg    1200
atcccacgca aagtgtgtaa cggaataggt attggtgaat ttaaagactc actctccata    1260
aatgctacga atattaaaca cttcaaaaac tgcacctcca tcagtggcga tctccacatc    1320
ctgccggtgg catttagggg tgactccttc acacatactc ctcctctgga tccacaggaa    1380
ctggatattc tgaaaaccgt aaaggaaatc acagggtttt tgctgattca ggcttggcct    1440
gaaaacagga cggacctcca tgcctttgag aacctagaaa tcatacgcgg caggaccaag    1500
caacatggtc agttttctct tgcagtcgtc agcctgaaca taacatcctt gggattacgc    1560
tccctcaagg agataagtga tggagatgtg ataatttcag gaaacaaaaa tttgtgctat    1620
gcaaatacaa taaactggaa aaaactgttt gggacctccg gtcagaaaac caaaattata    1680
agcaacagag tgaaaacag ctgcaaggcc acaggcagg tctgccatgc cttgtgctcc    1740
cccgagggct gctggggccc ggagcccagg gactgcgtct cttgccggaa tgtcagccga    1800
ggcagggaat gcgtggacaa gtgcaaccctt ctggagggtg agccaaggga gtttgtggag    1860
aactctgagt gcatacagtg ccaccccagag tgcctgcctc aggccatgaa catcacctgc    1920
acaggacggg gaccagacaa ctgtatccag tgtgcccact acattgacgg cccccactgc    1980
gtcaagacct gcccggcagg agtcatggga gaaaacaaca cctggtctg gaagtacgca    2040
gacgccggcc atgtgtgcca cctgtgccat ccaaactgca cctacggatg cactgggcca    2100
ggtcttgaag ctgtccaac gaatgggcct aagatcccgt ccatcgccac tgggatggtg    2160
ggggccctcc tcttgctgct ggtggtggcc ctggggatcg gcctcttcat gtga          2214
```

<210> SEQ ID NO 18
<211> LENGTH: 737
<212> TYPE: PRT
<213> ORGANISM: Artificial Sequence
<220> FEATURE:
<223> OTHER INFORMATION: Synthetic polypeptide (HN3-CAR)

<400> SEQUENCE: 18

```
Met Leu Leu Leu Val Thr Ser Leu Leu Leu Cys Glu Leu Pro His Pro
1               5                   10                  15

Ala Phe Leu Leu Ile Pro His Met Gln Val Gln Leu Val Gln Ser Gly
            20                  25                  30

Gly Gly Leu Val Gln Pro Gly Gly Ser Leu Arg Leu Ser Cys Ala Ala
        35                  40                  45

Ser Tyr Phe Asp Phe Asp Ser Tyr Glu Met Ser Trp Val Arg Gln Ala
    50                  55                  60

Pro Gly Lys Gly Leu Glu Trp Ile Gly Ser Ile Tyr His Ser Gly Ser
65                  70                  75                  80

Thr Tyr Tyr Asn Pro Ser Leu Lys Ser Arg Val Thr Ile Ser Arg Asp
                85                  90                  95

Asn Ser Lys Asn Thr Leu Tyr Leu Gln Met Asn Thr Leu Arg Ala Glu
            100                 105                 110

Asp Thr Ala Thr Tyr Tyr Cys Ala Arg Val Asn Met Asp Arg Phe Asp
        115                 120                 125

Tyr Trp Gly Gln Gly Thr Leu Val Thr Val Ser Ser Thr Ser Thr Thr
    130                 135                 140

Thr Pro Ala Pro Arg Pro Thr Pro Ala Pro Thr Ile Ala Ser Gln
145                 150                 155                 160

Pro Leu Ser Leu Arg Pro Glu Ala Cys Arg Pro Ala Ala Gly Gly Ala
                165                 170                 175

Val His Thr Arg Gly Leu Asp Phe Ala Cys Asp Ile Tyr Ile Trp Ala
            180                 185                 190

Pro Leu Ala Gly Thr Cys Gly Val Leu Leu Leu Ser Leu Val Ile Thr
        195                 200                 205

Lys Arg Gly Arg Lys Lys Leu Leu Tyr Ile Phe Lys Gln Pro Phe Met
    210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Gln Gln Gly Gln Asn Gln Leu Tyr Asn
            260                 265                 270

Glu Leu Asn Leu Gly Arg Arg Glu Glu Tyr Asp Val Leu Asp Lys Arg
        275                 280                 285

Arg Gly Arg Asp Pro Glu Met Gly Gly Lys Pro Arg Arg Lys Asn Pro
    290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
                325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg Glu Gly Arg Gly Ser Leu
        355                 360                 365
```

Leu Thr Cys Gly Asp Val Glu Glu Asn Pro Gly Pro Met Leu Leu Leu
370                 375                 380

Val Thr Ser Leu Leu Leu Cys Glu Leu Pro His Pro Ala Phe Leu Leu
385                 390                 395                 400

Ile Pro Arg Lys Val Cys Asn Gly Ile Gly Ile Gly Glu Phe Lys Asp
            405                 410                 415

Ser Leu Ser Ile Asn Ala Thr Asn Ile Lys His Phe Lys Asn Cys Thr
            420                 425                 430

Ser Ile Ser Gly Asp Leu His Ile Leu Pro Val Ala Phe Arg Gly Asp
            435                 440                 445

Ser Phe Thr His Thr Pro Pro Leu Asp Pro Gln Glu Leu Asp Ile Leu
450                 455                 460

Lys Thr Val Lys Glu Ile Thr Gly Phe Leu Leu Ile Gln Ala Trp Pro
465                 470                 475                 480

Glu Asn Arg Thr Asp Leu His Ala Phe Glu Asn Leu Glu Ile Ile Arg
            485                 490                 495

Gly Arg Thr Lys Gln His Gly Gln Phe Ser Leu Ala Val Val Ser Leu
            500                 505                 510

Asn Ile Thr Ser Leu Gly Leu Arg Ser Leu Lys Glu Ile Ser Asp Gly
            515                 520                 525

Asp Val Ile Ile Ser Gly Asn Lys Asn Leu Cys Tyr Ala Asn Thr Ile
530                 535                 540

Asn Trp Lys Lys Leu Phe Gly Thr Ser Gly Gln Lys Thr Lys Ile Ile
545                 550                 555                 560

Ser Asn Arg Gly Glu Asn Ser Cys Lys Ala Thr Gly Gln Val Cys His
            565                 570                 575

Ala Leu Cys Ser Pro Glu Gly Cys Trp Gly Pro Glu Pro Arg Asp Cys
            580                 585                 590

Val Ser Cys Arg Asn Val Ser Arg Gly Arg Glu Cys Val Asp Lys Cys
            595                 600                 605

Asn Leu Leu Glu Gly Glu Pro Arg Glu Phe Val Glu Asn Ser Glu Cys
610                 615                 620

Ile Gln Cys His Pro Glu Cys Leu Pro Gln Ala Met Asn Ile Thr Cys
625                 630                 635                 640

Thr Gly Arg Gly Pro Asp Asn Cys Ile Gln Cys Ala His Tyr Ile Asp
            645                 650                 655

Gly Pro His Cys Val Lys Thr Cys Pro Ala Gly Val Met Gly Glu Asn
            660                 665                 670

Asn Thr Leu Val Trp Lys Tyr Ala Asp Ala Gly His Val Cys His Leu
            675                 680                 685

Cys His Pro Asn Cys Thr Tyr Gly Cys Thr Gly Pro Gly Leu Glu Gly
690                 695                 700

Cys Pro Thr Asn Gly Pro Lys Ile Pro Ser Ile Ala Thr Gly Met Val
705                 710                 715                 720

Gly Ala Leu Leu Leu Leu Leu Val Val Ala Leu Gly Ile Gly Leu Phe
            725                 730                 735

Met

<210> SEQ ID NO 19
<211> LENGTH: 2226
<212> TYPE: DNA
<213> ORGANISM: Artificial Sequence
<220> FEATURE:
<223> OTHER INFORMATION: Synthetic construct (pMH290)

<400> SEQUENCE: 19

```
atgcttctcc tggtgacaag ccttctgctc tgtgagttac cacacccagc attcctcctg      60
atcccacata tgcaggtgca gctggtgcag tctgggggag gcttggtaca gcctggaggg     120
tccctgagac tctcctgtgc agcctctgat ttctatttct atgattatga aatgagctgg     180
gtccgccagg ctccagggaa gggtctggag tggattggga ctgtctccta tagtgggagc     240
acctactaca acccgtccct caagagtcga gtcaccatct ccagagacaa ttccaagaac     300
acgctgtatc tgcaaatgaa caccctaaga gccgaggaca cagccatgta ttactgtgcg     360
agaggttaca gctatgatga ctcccgatat tttgactact ggggccaggg aaccctggtc     420
accgtctcct caactagtac cacgacgcca gcgccgcgac caccaacacc ggcgcccacc     480
atcgcgtcgc agcccctgtc cctgcgccca gaggcgtgcc ggccagcggc gggggcgca     540
gtgcacacga gggggctgga cttcgcctgt gacatctaca tctgggcgcc cttggccggg     600
acttgtgggg tccttctcct gtcactggtt atcaccaaac ggggcagaaa gaaactcctg     660
tatatattca acaaccatt tatgagacca gtacaaacta ctcaagagga gatggctgt      720
agctgccgat ttccagaaga agaagaagga ggatgtgaac tgagagtgaa gttcagcagg     780
agcgcagacg cccccgcgta ccagcagggc cagaaccagc tctataacga gctcaatcta     840
ggacgaagag aggagtacga tgttttggac aagagacgtg gccgggaccc tgagatgggg     900
ggaaagccga aaggaagaa ccctcaggaa ggcctgtaca tgaactgca gaaagataag       960
atggcggagg cctacagtga gattgggatg aaaggcgagc gccggagggg caaggggcac    1020
gatggccttt accagggtct cagtacagcc accaaggaca cctacgacgc ccttcacatg    1080
caggccctgc cccctcgcga gggcagagga agtcttctaa catgcggtga cgtggaggag    1140
aatcccggcc ctatgcttct cctggtgaca agccttctgc tctgtgagtt accacacca    1200
gcattcctcc tgatcccacg caaagtgtgt aacggaatag gtattggtga atttaaagac    1260
tcactctcca taaatgctac gaatattaaa cacttcaaaa actgcaccctc catcagtggc    1320
gatctccaca tcctgccggt ggcatttagg ggtgactcct tcacacatac tcctcctctg    1380
gatccacagg aactggatat tctgaaaacc gtaaaggaaa tcacagggtt tttgctgatt    1440
caggcttggc ctgaaaacag gacggacctc catgcctttg agaacctaga aatcatacgc    1500
ggcaggacca gcaacatgg tcagttttct cttgcagtcg tcagcctgaa cataacatcc    1560
ttgggattac gctccctcaa ggagataagt gatggagatg tgataatttc aggaaacaaa    1620
aatttgtgct atgcaaatac aataaactgg aaaaaactgt ttgggacctc cggtcagaaa    1680
accaaaatta taagcaacag aggtgaaaac agctgcaagg ccacaggcca ggtctgccat    1740
gccttgtgct cccccgaggg ctgctggggc ccggagccca gggactgcgt ctcttgccgg    1800
aatgtcagcc gaggcaggga atgcgtggac aagtgcaacc ttctggaggg tgagccaagg    1860
gagtttgtgg agaactctga gtgcatacag tgccacccag agtgcctgcc tcaggccatg    1920
aacatcacct gcacaggacg ggaccagac aactgtatcc agtgtgccca ctacattgac    1980
ggcccccact gcgtcaagac ctgcccggca ggagtcatgg agaaaacaa cacccctggtc    2040
tggaagtacg cagacgccgg ccatgtgtgc cacctgtgcc atccaaactg cacctacgga    2100
tgcactgggc caggtcttga aggctgtcca acgaatgggc taagatccc gtccatcgcc    2160
actgggatgg tgggggccct cctcttgctg ctggtggtgg ccctggggat cggcctcttc    2220
atgtga                                                              2226
```

<210> SEQ ID NO 20
<211> LENGTH: 741
<212> TYPE: PRT
<213> ORGANISM: Artificial Sequence
<220> FEATURE:
<223> OTHER INFORMATION: Synthetic polypeptide (LH7-CAR)

<400> SEQUENCE: 20

```
Met Leu Leu Leu Val Thr Ser Leu Leu Leu Cys Glu Leu Pro His Pro
1               5                   10                  15

Ala Phe Leu Leu Ile Pro His Met Gln Val Gln Leu Val Gln Ser Gly
            20                  25                  30

Gly Gly Leu Val Gln Pro Gly Gly Ser Leu Arg Leu Ser Cys Ala Ala
        35                  40                  45

Ser Asp Phe Tyr Phe Tyr Asp Tyr Glu Met Ser Trp Val Arg Gln Ala
    50                  55                  60

Pro Gly Lys Gly Leu Glu Trp Ile Gly Thr Val Ser Tyr Ser Gly Ser
65                  70                  75                  80

Thr Tyr Tyr Asn Pro Ser Leu Lys Ser Arg Val Thr Ile Ser Arg Asp
                85                  90                  95

Asn Ser Lys Asn Thr Leu Tyr Leu Gln Met Asn Thr Leu Arg Ala Glu
            100                 105                 110

Asp Thr Ala Met Tyr Tyr Cys Ala Arg Gly Tyr Ser Tyr Asp Asp Ser
        115                 120                 125

Arg Tyr Phe Asp Tyr Trp Gly Gln Gly Thr Leu Val Thr Val Ser Ser
    130                 135                 140

Thr Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Lys Arg Gly Arg Lys Lys Leu Leu Tyr Ile Phe Lys
    210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu Arg Val
                245                 250                 255

Lys Phe Ser Arg Ser Ala Asp Ala Pro Ala Tyr Gln Gln Gly Gln Asn
            260                 265                 270

Gln Leu Tyr Asn Glu Leu Asn Leu Gly Arg Arg Glu Glu Tyr Asp Val
        275                 280                 285

Leu Asp Lys Arg Arg Gly Arg Asp Pro Glu Met Gly Gly Lys Pro Arg
    290                 295                 300

Arg Lys Asn Pro Gln Glu Gly Leu Tyr Asn Glu Leu Gln Lys Asp Lys
305                 310                 315                 320

Met Ala Glu Ala Tyr Ser Glu Ile Gly Met Lys Gly Glu Arg Arg Arg
                325                 330                 335

Gly Lys Gly His Asp Gly Leu Tyr Gln Gly Leu Ser Thr Ala Thr Lys
            340                 345                 350

Asp Thr Tyr Asp Ala Leu His Met Gln Ala Leu Pro Pro Arg Glu Gly
        355                 360                 365

Arg Gly Ser Leu Leu Thr Cys Gly Asp Val Glu Glu Asn Pro Gly Pro
```

```
            370                 375                 380
Met Leu Leu Leu Val Thr Ser Leu Leu Leu Cys Glu Leu Pro His Pro
385                 390                 395                 400

Ala Phe Leu Leu Ile Pro Arg Lys Val Cys Asn Gly Ile Gly Ile Gly
                405                 410                 415

Glu Phe Lys Asp Ser Leu Ser Ile Asn Ala Thr Asn Ile Lys His Phe
                420                 425                 430

Lys Asn Cys Thr Ser Ile Ser Gly Asp Leu His Ile Leu Pro Val Ala
                435                 440                 445

Phe Arg Gly Asp Ser Phe Thr His Thr Pro Pro Leu Asp Pro Gln Glu
                450                 455                 460

Leu Asp Ile Leu Lys Thr Val Lys Glu Ile Thr Gly Phe Leu Leu Ile
465                 470                 475                 480

Gln Ala Trp Pro Glu Asn Arg Thr Asp Leu His Ala Phe Glu Asn Leu
                485                 490                 495

Glu Ile Ile Arg Gly Arg Thr Lys Gln His Gly Gln Phe Ser Leu Ala
                500                 505                 510

Val Val Ser Leu Asn Ile Thr Ser Leu Gly Leu Arg Ser Leu Lys Glu
                515                 520                 525

Ile Ser Asp Gly Asp Val Ile Ile Ser Gly Asn Lys Asn Leu Cys Tyr
                530                 535                 540

Ala Asn Thr Ile Asn Trp Lys Lys Leu Phe Gly Thr Ser Gly Gln Lys
545                 550                 555                 560

Thr Lys Ile Ile Ser Asn Arg Gly Glu Asn Ser Cys Lys Ala Thr Gly
                565                 570                 575

Gln Val Cys His Ala Leu Cys Ser Pro Glu Gly Cys Trp Gly Pro Glu
                580                 585                 590

Pro Arg Asp Cys Val Ser Cys Arg Asn Val Ser Arg Gly Arg Glu Cys
                595                 600                 605

Val Asp Lys Cys Asn Leu Leu Glu Gly Glu Pro Arg Glu Phe Val Glu
                610                 615                 620

Asn Ser Glu Cys Ile Gln Cys His Pro Glu Cys Leu Pro Gln Ala Met
625                 630                 635                 640

Asn Ile Thr Cys Thr Gly Arg Gly Pro Asp Asn Cys Ile Gln Cys Ala
                645                 650                 655

His Tyr Ile Asp Gly Pro His Cys Val Lys Thr Cys Pro Ala Gly Val
                660                 665                 670

Met Gly Glu Asn Asn Thr Leu Val Trp Lys Tyr Ala Asp Ala Gly His
                675                 680                 685

Val Cys His Leu Cys His Pro Asn Cys Thr Tyr Gly Cys Thr Gly Pro
                690                 695                 700

Gly Leu Glu Gly Cys Pro Thr Asn Gly Pro Lys Ile Pro Ser Ile Ala
705                 710                 715                 720

Thr Gly Met Val Gly Ala Leu Leu Leu Leu Val Val Ala Leu Gly
                725                 730                 735

Ile Gly Leu Phe Met
                740

<210> SEQ ID NO 21
<211> LENGTH: 351
<212> TYPE: DNA
<213> ORGANISM: Artificial Sequence
<220> FEATURE:
<223> OTHER INFORMATION: Synthetic polynucleotide (YP7 VH domain)
```

<400> SEQUENCE: 21

| | | |
|---|---|---|
| gaggtgcagc ttgttgagac tggtggagga atggtgcagc ctgaagggtc attgaaactc | 60 |
| tcatgtgcag cctctggatt caccttcaat aagaatgcca tgaattgggt ccgccaggct | 120 |
| ccaggaaagg gtttggaatg ggttgctcgc ataagaaata aaactaataa ttatgcaaca | 180 |
| tattatgccg attcagtgaa agccaggttt accatctcca gagatgattc acaaagcatg | 240 |
| ctctatctgc aaatgaacaa cttgaaaatt gaggacacag ccatgtacta ttgtgtggct | 300 |
| ggtaactcgt ttgcttactg gggccaaggg actctggtca ctgtctctgc a | 351 |

<210> SEQ ID NO 22
<211> LENGTH: 117
<212> TYPE: PRT
<213> ORGANISM: Artificial Sequence
<220> FEATURE:
<223> OTHER INFORMATION: Synthetic polypeptide (YP7 VH domain)

<400> SEQUENCE: 22

Glu Val Gln Leu Val Glu Thr Gly Gly Gly Met Val Gln Pro Glu Gly
1               5                   10                  15

Ser Leu Lys Leu Ser Cys Ala Ala Ser Gly Phe Thr Phe Asn Lys Asn
            20                  25                  30

Ala Met Asn Trp Val Arg Gln Ala Pro Gly Lys Gly Leu Glu Trp Val
        35                  40                  45

Ala Arg Ile Arg Asn Lys Thr Asn Asn Tyr Ala Thr Tyr Tyr Ala Asp
    50                  55                  60

Ser Val Lys Ala Arg Phe Thr Ile Ser Arg Asp Asp Ser Gln Ser Met
65                  70                  75                  80

Leu Tyr Leu Gln Met Asn Asn Leu Lys Ile Glu Asp Thr Ala Met Tyr
                85                  90                  95

Tyr Cys Val Ala Gly Asn Ser Phe Ala Tyr Trp Gly Gln Gly Thr Leu
            100                 105                 110

Val Thr Val Ser Ala
        115

<210> SEQ ID NO 23
<211> LENGTH: 339
<212> TYPE: DNA
<213> ORGANISM: Artificial Sequence
<220> FEATURE:
<223> OTHER INFORMATION: Synthetic polynucleotide (YP7 VL domain)

<400> SEQUENCE: 23

| | | |
|---|---|---|
| gacattgtga tgtcacagtc tccatcctcc ctagttgtgt caattggaga gaaggttact | 60 |
| atgacctgca agtccagtca gagccttttta tatagcagca atcaaaagaa ctacttggcc | 120 |
| tggtaccaac agaaaccagg gcagtctcct aaactgctga tttactgggc atccagtagg | 180 |
| gaatctgggg tccctgatcg cttcacaggc agtggatctg gacagatttt cactctcacc | 240 |
| atcagcagtg tgaaggctga agacctggca gtttattact gtcagcaata ttataactat | 300 |
| ccgctcacgt tcggtgctgg gaccaagttg gagctgaaa | 339 |

<210> SEQ ID NO 24
<211> LENGTH: 113
<212> TYPE: PRT
<213> ORGANISM: Artificial Sequence
<220> FEATURE:
<223> OTHER INFORMATION: Synthetic polypeptide (YP7 VL domain)

<400> SEQUENCE: 24

-continued

```
Asp Ile Val Met Ser Gln Ser Pro Ser Ser Leu Val Val Ser Ile Gly
1               5                   10                  15

Glu Lys Val Thr Met Thr Cys Lys Ser Ser Gln Ser Leu Leu Tyr Ser
                20                  25                  30

Ser Asn Gln Lys Asn Tyr Leu Ala Trp Tyr Gln Lys Pro Gly Gln
            35                  40                  45

Ser Pro Lys Leu Leu Ile Tyr Trp Ala Ser Arg Glu Ser Gly Val
50                      55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Tyr Pro Leu Thr Phe Gly Ala Gly Thr Lys Leu Glu Leu
            100                 105                 110

Lys
```

<210> SEQ ID NO 25
<211> LENGTH: 351
<212> TYPE: DNA
<213> ORGANISM: Artificial Sequence
<220> FEATURE:
<223> OTHER INFORMATION: Synthetic polynucleotide (hYP7 VH domain)

<400> SEQUENCE: 25

```
gaggtgcagc ttgttgagtc tggtggagga ttggtgcagc ctggagggtc attgagactc    60
tcatgtgcag cctctggatt caccttcaat aagaatgcca tgaattgggt ccgccaggct   120
ccaggaaagg gtttggaatg ggttggccgc ataagaaata aaactaataa ttatgcaaca   180
tattatgccg attcagtgaa agccaggttt accatctcca gagatgattc aaagaactca   240
ctctatctgc aaatgaacag cttgaaaacc gaggacacag ccgtgtacta ttgtgtggct   300
ggtaactcgt ttgcttactg gggccaaggg actctggtca ctgtctctgc a           351
```

<210> SEQ ID NO 26
<211> LENGTH: 117
<212> TYPE: PRT
<213> ORGANISM: Artificial Sequence
<220> FEATURE:
<223> OTHER INFORMATION: Synthetic polypeptide (hYP7 VH domain)

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Lys Asn
                20                  25                  30

Ala Met Asn Trp Val Arg Gln Ala Pro Gly Lys Gly Leu Glu Trp Val
            35                  40                  45

Gly Arg Ile Arg Asn Lys Thr Asn Asn Tyr Ala Thr Tyr Tyr Ala Asp
50                  55                  60

Ser Val Lys Ala Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Ala Gly Asn Ser Phe Ala Tyr Trp Gly Gln Gly Thr Leu
            100                 105                 110

Val Thr Val Ser Ala
            115
```

<210> SEQ ID NO 27
<211> LENGTH: 339
<212> TYPE: DNA
<213> ORGANISM: Artificial Sequence
<220> FEATURE:
<223> OTHER INFORMATION: Synthetic polynucleotide (hYP7 VL domain)

<400> SEQUENCE: 27

```
gacattgtga tgacccagtc tccagactcc ctagctgtgt cactgggaga gagggccact      60
atcaactgca agtccagtca gagccttttta tatagcagca atcaaaagaa ctacttggcc    120
tggtaccaac agaaaccagg gcagcctcct aaactgctga tttactgggc atccagtagg    180
gaatctgggg tccctgatcg cttcagtggc agtggatctg ggacagattt cactctcacc    240
atcagcagtc tgcaggctga agacgtggca gtttattact gtcagcaata ttataactat    300
ccgctcacgt tcggtcaggg gaccaagttg gagatcaaa                            339
```

<210> SEQ ID NO 28
<211> LENGTH: 113
<212> TYPE: PRT
<213> ORGANISM: Artificial Sequence
<220> FEATURE:
<223> OTHER INFORMATION: Synthetic polypeptide (hYP7 VL domain)

<400> SEQUENCE: 28

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Tyr Pro Leu Thr Phe Gly Gln Gly Thr Lys Leu Glu Ile
            100                 105                 110

Lys
```

<210> SEQ ID NO 29
<211> LENGTH: 351
<212> TYPE: DNA
<213> ORGANISM: Artificial Sequence
<220> FEATURE:
<223> OTHER INFORMATION: Synthetic polynucleotide (HN3)

<400> SEQUENCE: 29

```
caggtgcagc tggtgcagtc tgggggaggc ttggtacagc ctggagggtc cctgagactc      60
tcctgtgcag cctcttattt cgatttcgat tcttatgaaa tgagctgggt ccgccaggct    120
ccagggaagg gcctagagtg gattggagt atctatcata gtgggagcac ctactacaac    180
ccgtccctca agagtcgagt caccatctcc agagacaatt ccaagaacac gctgtatctg    240
caaatgaaca ccctgagagc cgaggacaca gccacgtatt actgtgcgag agtaaatatg    300
gaccgatttg actactgggg ccagggaacc ctggtcaccg tctcctcaag t             351
```

<210> SEQ ID NO 30
<211> LENGTH: 117
<212> TYPE: PRT
<213> ORGANISM: Artificial Sequence
<220> FEATURE:
<223> OTHER INFORMATION: Synthetic polypeptide (HN3)

<400> SEQUENCE: 30

```
Gln Val Gln Leu Val Gln Ser Gly Gly Gly Leu Val Gln Pro Gly Gly
1               5                   10                  15

Ser Leu Arg Leu Ser Cys Ala Ala Ser Tyr Phe Asp Phe Asp Ser Tyr
            20                  25                  30

Glu Met Ser Trp Val Arg Gln Ala Pro Gly Lys Gly Leu Glu Trp Ile
        35                  40                  45

Gly Ser Ile Tyr His Ser Gly Ser Thr Tyr Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Thr Tyr Tyr Cys Ala
                85                  90                  95

Arg Val Asn Met Asp Arg Phe Asp Tyr Trp Gly Gln Gly Thr Leu Val
            100                 105                 110

Thr Val Ser Ser Ser
        115
```

<210> SEQ ID NO 31
<211> LENGTH: 360
<212> TYPE: DNA
<213> ORGANISM: Artificial Sequence
<220> FEATURE:
<223> OTHER INFORMATION: Synthetic polynucleotide (LH7)

<400> SEQUENCE: 31

```
caggtgcagc tggtgcagtc tgggggaggc ttggtacagc ctggagggtc cctgagactc      60
tcctgtgcag cctctgattt ctatttctat gattatgaaa tgagctgggt ccgccaggct     120
ccagggaagg gtctggagtg gattgggact gtctcctata gtgggagcac ctactacaac     180
ccgtccctca agagtcgagt caccatctcc agagacaatt ccaagaacac gctgtatctg     240
caaatgaaca ccctaagagc cgaggacaca gccatgtatt actgtgcgag aggttacagc     300
tatgatgact cccgatattt tgactactgg ggccagggaa ccctggtcac cgtctcctca     360
```

<210> SEQ ID NO 32
<211> LENGTH: 120
<212> TYPE: PRT
<213> ORGANISM: Artificial Sequence
<220> FEATURE:
<223> OTHER INFORMATION: Synthetic polypeptide (LH7)

<400> SEQUENCE: 32

```
Gln Val Gln Leu Val Gln Ser Gly Gly Gly Leu Val Gln Pro Gly Gly
1               5                   10                  15

Ser Leu Arg Leu Ser Cys Ala Ala Ser Asp Phe Tyr Phe Tyr Asp Tyr
            20                  25                  30

Glu Met Ser Trp Val Arg Gln Ala Pro Gly Lys Gly Leu Glu Trp Ile
        35                  40                  45

Gly Thr Val Ser Tyr Ser Gly Ser Thr Tyr Tyr Asn Pro Ser Leu Lys
    50                  55                  60

Ser Arg Val Thr Ile Ser Arg Asp Asn Ser Lys Asn Thr Leu Tyr Leu
65                  70                  75                  80
```

Gln Met Asn Thr Leu Arg Ala Glu Asp Thr Ala Met Tyr Tyr Cys Ala
                85                  90                  95

Arg Gly Tyr Ser Tyr Asp Asp Ser Arg Tyr Phe Asp Tyr Trp Gly Gln
            100                 105                 110

Gly Thr Leu Val Thr Val Ser Ser
        115                 120

<210> SEQ ID NO 33
<211> LENGTH: 360
<212> TYPE: DNA
<213> ORGANISM: Artificial Sequence
<220> FEATURE:
<223> OTHER INFORMATION: Synthetic polynucleotide (LH4)

<400> SEQUENCE: 33
caggtgcagc tggtgcagtc tgggggaggc ttggtacagc ctggagggtc cctgagactc      60
tcctgtgcag cctcttcttt ctatttcgat gattatgaaa tgagctgggt ccgccaggct     120
ccagggaagg ccctggagtg gattgggcgt atctatacca gtgggagcac caactacaac     180
ccctccctca gagtcgagt caccatctcc agagacaatt ccaagaacac gctgtatctg     240
caaatgaaca ccctgagagc cgaggacaca gccacgtatt actgtgcgag gggatattgt     300
agtggtggta gctgctactt tgactactgg ggccagggaa ccctggtcac cgtctcctca     360

<210> SEQ ID NO 34
<211> LENGTH: 120
<212> TYPE: PRT
<213> ORGANISM: Artificial Sequence
<220> FEATURE:
<223> OTHER INFORMATION: Synthetic polypeptide (LH4)

<400> SEQUENCE: 34

Gln Val Gln Leu Val Gln Ser Gly Gly Gly Leu Val Gln Pro Gly Gly
1               5                   10                  15

Ser Leu Arg Leu Ser Cys Ala Ala Ser Ser Phe Tyr Phe Asp Asp Tyr
            20                  25                  30

Glu Met Ser Trp Val Arg Gln Ala Pro Gly Lys Ala Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Thr Tyr Tyr Cys Ala
                85                  90                  95

Arg Gly Tyr Cys Ser Gly Gly Ser Cys Tyr Phe Asp Tyr Trp Gly Gln
            100                 105                 110

Gly Thr Leu Val Thr Val Ser Ser
        115                 120

<210> SEQ ID NO 35
<211> LENGTH: 363
<212> TYPE: DNA
<213> ORGANISM: Artificial Sequence
<220> FEATURE:
<223> OTHER INFORMATION: Synthetic polynucleotide (LH6)

<400> SEQUENCE: 35
caggtgcagc tggtgcagtc tgggggaggc ttggtacagc ctggagggtc cctgagactc      60
tcctgtgcag cctctgattt ctatttcgat gattatgaaa tgagctgggt ccgccaggct     120

```
ccagggaagg ggctggagtg ggtctcaact attagtggta gtggtggtgg cacatactac    180
gcagactcag tgaagggccg attcaccatc tccagagaca attccaagaa cacgctgtat    240
ctgcaaatga acaccctgag agccgaggac acagccacat attactgtgc gagaggttac    300
agttatgacg actcccgata ttttgactac tggggccagg gaaccctggt caccgtctcc    360
tca                                                                  363
```

<210> SEQ ID NO 36
<211> LENGTH: 121
<212> TYPE: PRT
<213> ORGANISM: Artificial Sequence
<220> FEATURE:
<223> OTHER INFORMATION: Synthetic polypeptide (LH6)

<400> SEQUENCE: 36

```
Gln Val Gln Leu Val Gln Ser Gly Gly Gly Leu Val Gln Pro Gly Gly
1               5                   10                  15

Ser Leu Arg Leu Ser Cys Ala Ala Ser Asp Phe Tyr Phe Asp Asp Tyr
            20                  25                  30

Glu Met Ser Trp Val Arg Gln Ala Pro Gly Lys Gly Leu Glu Trp Val
        35                  40                  45

Ser Thr Ile Ser Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Thr Tyr Tyr Cys
            85                  90                  95

Ala Arg Gly Tyr Ser Tyr Asp Asp Ser Arg Tyr Phe Asp Tyr Trp Gly
            100                 105                 110

Gln Gly Thr Leu Val Thr Val Ser Ser
            115                 120
```

<210> SEQ ID NO 37
<211> LENGTH: 369
<212> TYPE: DNA
<213> ORGANISM: Artificial Sequence
<220> FEATURE:
<223> OTHER INFORMATION: Synthetic polynucleotide (YP218 VH domain)

<400> SEQUENCE: 37

```
cagcagcagc tggaggagtc cgggggaggc ctggtcaagc ctgagggatc cctgacactc    60
acctgcaaag cctctggatt cgacctcggt ttctactttt acgcctgttg ggtccgccag    120
gctccaggga agggcctgga gtggatcgca tgcatttata ctgctggtag tggtagcacg    180
tactacgcga gctgggcgaa aggccgattc accatctcca agcctcgtc gaccacggtg    240 actctgcaaa tgaccagtct ggcagccgcg gacacggcca cctatttctg tgcgagatct    300
actgctaata ctagaagtac ttattatctt aacttgtggg gcccaggcac cctggtcacc    360
gtctcctca                                                            369
```

<210> SEQ ID NO 38
<211> LENGTH: 123
<212> TYPE: PRT
<213> ORGANISM: Artificial Sequence
<220> FEATURE:
<223> OTHER INFORMATION: Synthetic polypeptide (YP218 VH domain)

<400> SEQUENCE: 38

```
Gln Gln Gln Leu Glu Glu Ser Gly Gly Gly Leu Val Lys Pro Glu Gly
1               5                   10                  15

Ser Leu Thr Leu Thr Cys Lys Ala Ser Gly Phe Asp Leu Gly Phe Tyr
            20                  25                  30

Phe Tyr Ala Cys Trp Val Arg Gln Ala Pro Gly Lys Gly Leu Glu Trp
        35                  40                  45

Ile Ala Cys Ile Tyr Thr Ala Gly Ser Gly Ser Thr Tyr Tyr Ala Ser
    50                  55                  60

Trp Ala Lys Gly Arg Phe Thr Ile Ser Lys Ala Ser Ser Thr Thr Val
65                  70                  75                  80

Thr Leu Gln Met Thr Ser Leu Ala Ala Ala Asp Thr Ala Thr Tyr Phe
                85                  90                  95

Cys Ala Arg Ser Thr Ala Asn Thr Arg Ser Tyr Tyr Leu Asn Leu
            100                 105                 110

Trp Gly Pro Gly Thr Leu Val Thr Val Ser Ser
            115                 120
```

```
<210> SEQ ID NO 39
<211> LENGTH: 330
<212> TYPE: DNA
<213> ORGANISM: Artificial Sequence
<220> FEATURE:
<223> OTHER INFORMATION: Synthetic polynucleotide (YP218 VL domain)

<400> SEQUENCE: 39
gacgtcgtga tgacccagac tccagcctcc gtgtctgaac ctgtgggagg cacagtcacc      60
atcaagtgcc aggccagtca gaggattagt agttacttat cctggtatca gcagaaacca     120
gggcagcgtc ccaagctcct gatctttggt gcatccactc tggcatctgg ggtcccctcg     180
cggttcaaag gcagtggatc tgggacagaa tacactctca ccatcagcga cctggagtgt     240
gccgatgctg ccacttacta ctgtcagagt tatgcttatt ttgatagtaa taattggcat     300
gctttcggcg agggaccgga ggtggtggtc                                      330

<210> SEQ ID NO 40
<211> LENGTH: 110
<212> TYPE: PRT
<213> ORGANISM: Artificial Sequence
<220> FEATURE:
<223> OTHER INFORMATION: Synthetic polypeptide (YP218 VL domain)

<400> SEQUENCE: 40

Asp Val Val Met Thr Gln Thr Pro Ala Ser Val Ser Glu Pro Val Gly
1               5                   10                  15

Gly Thr Val Thr Ile Lys Cys Gln Ala Ser Gln Arg Ile Ser Ser Tyr
            20                  25                  30

Leu Ser Trp Tyr Gln Gln Lys Pro Gly Gln Arg Pro Lys Leu Leu Ile
        35                  40                  45

Phe Gly Ala Ser Thr Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Ser Tyr Ala Tyr Phe Asp Ser
                85                  90                  95

Asn Asn Trp His Ala Phe Gly Gly Gly Thr Glu Val Val Val
            100                 105                 110

<210> SEQ ID NO 41
```

```
<211> LENGTH: 339
<212> TYPE: DNA
<213> ORGANISM: Artificial Sequence
<220> FEATURE:
<223> OTHER INFORMATION: Synthetic polynucleotide (SD1)

<400> SEQUENCE: 41
caggtgcagc tggtgcagtc tgggggaggc ttggtacagc ctggagggtc cctgagactc      60
tcctgtgcag cctctgattt cgatttcgct gcttatgaaa tgagctgggt ccgccaggct     120
ccaggacaag gccttgagtg ggtggcaatt atatcacatg atggaatcga taaatactac     180
acagactccg tgaagggccg attcaccatc tccagagaca attccaagaa cacgctgtat     240
ctgcaaatga acaccctgag agccgaggac acagccacgt attactgttt aaggcttggt     300
gctgtaggcc agggaaccct ggtcaccgtc tcctcaagt                            339

<210> SEQ ID NO 42
<211> LENGTH: 113
<212> TYPE: PRT
<213> ORGANISM: Artificial Sequence
<220> FEATURE:
<223> OTHER INFORMATION: Synthetic polypeptide (SD1)

<400> SEQUENCE: 42

Gln Val Gln Leu Val Gln Ser Gly Gly Gly Leu Val Gln Pro Gly Gly
1               5                   10                  15

Ser Leu Arg Leu Ser Cys Ala Ala Ser Asp Phe Asp Phe Ala Ala Tyr
            20                  25                  30

Glu Met Ser Trp Val Arg Gln Ala Pro Gly Gln Gly Leu Glu Trp Val
        35                  40                  45

Ala Ile Ile Ser His Asp Gly Ile Asp Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Thr Tyr Tyr Cys
            85                  90                  95

Leu Arg Leu Gly Ala Val Gly Gln Gly Thr Leu Val Thr Val Ser Ser
            100                 105                 110

Ser

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
gcagtctctg gaagaaggag                                                  20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
tggtgacagg tggcgtccgg                                                  20

<210> SEQ ID NO 45
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
cggttttcca aggtgagttc                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
ggtcacgtct tgctcctcgg                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
gacatcaatg agtgcctccg                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
gataataagc agatctatat                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
cgttttccgc cacagggcta                                               20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
agggtgtcgt tttccgccac                                               20

<210> SEQ ID NO 51
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 51
gaggcagagc aggtagtcag                                            20
```

CHIMERIC ANTIGEN RECEPTORS TARGETING GLYPICAN-3 OR MESOTHELIN

CROSS REFERENCE TO RELATED APPLICATIONS

This application is the U.S. National Stage of International Application No. PCT/US2018/059645, filed Nov. 7, 2018, published in English under PCT Article 21(2), which claims the benefit of U.S. Provisional Application No. 62/584,421, filed Nov. 10, 2017, which is herein incorporated by reference in its entirety.

ACKNOWLEDGMENT OF GOVERNMENT SUPPORT

This invention was made with government support under project number Z01 BC010891 awarded by the National Institutes of Health, National Cancer Institute. The government has certain rights in the invention.

FIELD

This disclosure concerns chimeric antigen receptors specific for tumor antigens, and their use for cancer immunotherapy.

BACKGROUND

Chimeric antigen receptors (CARs) are composed of an antibody fragment specific for a tumor antigen, fused to a transmembrane domain and a T-cell-signaling moiety. The receptors, when expressed on the surface of T cells, mediate binding to a target and activate the T cells, ultimately inducing target cell lysis. CARs are emerging as one of the most promising approaches to treat hematological malignancies (Kochenderfer et al., Blood 119:2709-2720, 2012; Kochenderfer and Rosenberg, Nat Rev Clin Oncol 10:267-276, 2013; Porter et al., New Engl J Med 365:725-733, 2011; Maude et al., New Engl J Med 371:1507-1517, 2014; Grupp et al., New Engl J Med 368:1509-1518, 2013). Two CD19-targeted CARs, axicabtagene ciloleucel (Yescarta™) and tisagenlecleucel (Kymriah™), have been approved in the United States for the treatment of B-cell non-Hodgkin lymphoma and B-cell acute lymphoblastic leukemia, respectively. Clinical trials are currently underway to test various CAR T cell therapies for the treatment of solid tumors (Yu et al., J Hematol Oncol 10(1):78, 2017).

SUMMARY

Disclosed herein are nucleic acid constructs that encode both a chimeric antigen receptor (CAR) and a truncated human epidermal growth factor receptor (huEGFRt). The encoded CARs include a tumor antigen-specific monoclonal antibody fragment fused to an extracellular hinge region, a transmembrane region, an intracellular co-stimulatory domain and an intracellular signaling domain. The huEGFRt includes two EGFR extracellular domains (Domain III and Domain IV) and the EGFR transmembrane domain, but lacks the two membrane distal extracellular domains and all intracellular domains. Isolated cells, such as T lymphocytes, that co-express the disclosed CARs and huEGFRt are also disclosed. T cells transduced with the CAR constructs can be used for cancer immunotherapy.

Provided herein are nucleic acid molecules encoding a CAR and a huEGFRt. In some embodiments, the nucleic acid molecule includes, in the 5' to 3' direction, a nucleic acid encoding a first signal sequence; a nucleic acid encoding an antigen-specific antibody or antigen-binding fragment thereof; a nucleic acid encoding an extracellular hinge region; a nucleic acid encoding a transmembrane domain; a nucleic acid encoding an intracellular co-stimulatory domain; a nucleic acid encoding a intracellular signaling domain; a nucleic acid encoding a self-cleaving 2A peptide; a nucleic acid encoding a second signal sequence; and a nucleic acid encoding a huEGFRt. In some examples, the first and/or second signal sequence is a granulocyte-macrophage colony stimulating factor receptor signal sequence (GMCSFRss), the extracellular hinge region is a CD8α hinge region, the transmembrane domain is a CD8α transmembrane domain, the intracellular co-stimulatory domain is a 4-1BB co-stimulatory domain and the intracellular signaling domain is a CD3ζ signaling domain. In some examples, the antibody or antigen-binding fragment specifically binds a tumor antigen, such as glypican-3 (GPC3), GPC2 or mesothelin. Also provided are vectors, such as viral vectors, that include a nucleic acid molecule disclosed herein. In particular non-limiting examples, the viral vector is a lentiviral vector. Further provided are isolated host cells that include a nucleic acid molecule disclosed herein.

Also provided are isolated host cells that co-express a CAR and a huEGFRt. In some embodiments, the CAR includes an antigen-specific antibody or antigen-binding fragment thereof, an extracellular hinge region, a transmembrane domain, an intracellular co-stimulatory domain and an intracellular signaling domain; and/or the huEGFRt comprises a Domain III, a Domain IV and a transmembrane domain from human EGFR, but lacks an epidermal growth factor (EGF)-binding domain and a cytoplasmic domain. In some examples, the extracellular hinge region comprises a CD8α hinge region, the transmembrane domain comprises a CD8α transmembrane domain, the intracellular co-stimulatory domain comprises a 4-1BB co-stimulatory domain and the intracellular signaling domain comprises a CD3ζ signaling domain. In some examples, the antibody or antigen-binding fragment specifically binds a tumor antigen, such as GPC3, GPC2 or mesothelin.

Compositions that include an isolated host cell disclosed herein and a pharmaceutically acceptable carrier are further provided. In some embodiments, the isolated host cells are T lymphocytes.

Further provided are methods of treating a GPC3-positive cancer, a GPC2-positive cancer or a mesothelin-positive cancer in a subject, by administering to the subject an isolated host cell disclosed herein. In some embodiments, the isolated host cells are T lymphocytes, such as autologous T lymphocytes.

The foregoing and other objects, features, and advantages of the invention will become more apparent from the following detailed description, which proceeds with reference to the accompanying figures.

BRIEF DESCRIPTION OF THE DRAWINGS

(FIG. 3C) Control human serum IgG.

FIGS. 7A-7C are graphs showing that CAR.hYP7 T cells have persistent anti-tumor activity against Hep3B xenograft tumors in mice. (FIG. 7A) Tumor volume of Hep3B tumor bearing mice treated with PBS, mock-treated, 10 million CAR.HN3 T cells, 10 million CAR.hYP7 T cells, 20 million CAR.hYP7 T cells or 40 million CAR.hYP7 T cells up to 3 weeks post-treatment. (FIG. 7B) Tumor volume of Hep3B tumor bearing mice treated with PBS, 10 million CAR.HN3 T cells, 10 million CAR.hYP7 T cells or 40 million CAR.hYP7 T cells up to 7 weeks post-treatment. (FIG. 7C) Survival curve of Hep3B-tumor bearing mice. Mice were injected with PBS, 10 million CAR.hYP7 T cells or 40 million CAR.hYP7 T cells 10 days after Hep3B inoculation and survival was evaluated for 70 days. Treatment with 40 million CAR.hYP7 T cells led to 100% survival.

In FIGS. 10A-10C, each line represents an individual animal. Average tumor volume for all three treatment groups is shown in FIG. 8D.

FIGS. 10A-10E show generation and expression of GPC3 CAR T cells. (FIG. 10A) Schematic structure of HN3 and hYP7 antibodies binding to the N-lobe and C-lobe, respectively, of mature GPC3. (FIG. 10B) Schematic diagram of bicistronic lentiviral constructs expressing CARs targeting GPC3 along with huEGFRt using the T2A ribosomal skipping sequence. (FIG. 10C) CAR expression on healthy donor-derived T cells transduced with lentiviral particles was analyzed using flow cytometry by detection of EGFR expression. (FIG. 10D) CD3$^+$, CD4$^+$ and CD8$^+$ T cell population analysis of mock T cells and CAR (hYP7) T cells from healthy donor as well as HCC patient-derived CAR (hYP7) T cells. (FIG. 10E) Proliferation of CAR (hYP7) T cells in 8 different healthy donors and 4 different HCC patients as assessed by trypan blue exclusion assay.

(FIG. 11A) Lysis of GPC3-positive target cells (G1), but not GPC3-negative target cells (A431 and T3M4), as measured by luciferase activity. Mock or GPC3-targeted CAR T cells were co-cultured with luciferase-expressing target cells at the indicated effector (E): target (T) ratios for 24 hours, and specific lysis was measured using a luminescent-based cytolytic assay. (FIGS. 11B-11C) Cytolytic activity of CAR (HN3) T cells and CAR (hYP7) T cells derived from healthy donors (FIG. 11B) or HCC patients (FIG. 11C) after 24 hours of co-culture with Hep3B cells. (FIG. 11D) Robust proliferation of CAR (hYP7) T cells after stimulation with anti-CD3/CD28 beads over 35 days. (FIG. 11E) Cytolytic activity of CAR (hYP7) T cells on day 14 and day 28 post-activation when co-cultured with Hep3B cells for 24 hours. (FIG. 11F) Cytolytic activity of healthy donor-derived GPC3-specific CAR T cells after 24 hours of co-culture with HepG2 and Huh-7 cells. (FIG. 11G) GPC3-targeted CAR T cell-mediated killing of HepG2 cells as determined using IncuCyte zoom. HepG2 cells were incubated with CAR T cells at an E:T ratio of 2:1 up to 140 hours.

FIGS. 13A-13F show targeting GPC3 induces HCC cell apoptosis by suppressing Wnt/β-catenin signaling. (FIG. 13A) CAR (hYP7) T cells suppressed the expression of β-catenin and increased the expression of apoptotic markers (cleaved PARP and cleaved caspase-9) in Hep3B cells after 6 hours of treatment. (FIG. 13B) CAR (hYP7) T cells inhibited the expression of β-catenin in Hep3B cells in a time-dependent manner. (FIG. 13C) GPC3 protein expression in Hep3B cells after CRISPER/Cas9-mediated knockout of GPC3. (FIG. 13D) Antitumor activity of sgRNA5-2 targeting exon 5 of GPC3. Athymic nu/nu nude mice were subcutaneously inoculated with 5×10$^6$ Hep3B cells. When tumors reached an average volume of 150 mm$^3$, mice were treated by intratumoral injections of sgRNA5-2 plasmid or empty vector, every other day for 6 injections. (FIG. 13E) Knockout of GPC3 reduced the expression of β-catenin in mice tumors. (FIG. 13F) Serum AFP levels before and after the treatment of sgRNA5-2 plasmid or empty vector control. Mean and SD are shown. *p<0.05; **p<0.01.

(FIG. 14A) Experimental schematic. Hep3B tumor-bearing NSG mice were treated with either peritoneal injection of mock T cells, 5×10⁶ CAR (HN3) T cells, 5×10⁶ CAR (hYP7) T cells, 10×10⁶ CAR (hYP7) T cells or 20×10⁶ CAR (hYP7) T cells at day 12 after tumor cell inoculation. Tumor burden was monitored by bioluminescent imaging. (FIG. 14B) CAR (hYP7) T cells regressed established Hep3B xenografts at high dose (20 million cells) and inhibited tumor growth at low dose (5 million or 10 million cells). (FIG. 14C) Tumor bioluminescence as mean photon count in mice treated in FIG. 14B. (FIG. 14D) KaplanMeier survival curve of tumor-bearing mice after treatment with 5 million or 20 million CAR (hYP7) T cells. (FIG. 14E) Alpha fetoprotein levels in serum collected from groups shown in (FIG. 14B) two weeks or six weeks after CAR T treatment. Serum of three different mice from each group were collected for ELISA analysis. (FIG. 14F) CAR T cell persistence in xenograft tumor tissues after 3 weeks of treatment as measured by droplet digital PCR (ddPCR). Values represent mean±SD. *p<0.05; p<0.01; *p<0.001.

FIGS. 15A-15D show CAR (hYP7) T cells eliminate tumor cells in the HepG2 peritoneal dissemination xenograft mouse model. (FIG. 15A) Experimental schematic. HepG2 tumor-bearing NSG mice were treated with either peritoneal injection of mock T cells or 20×10⁶ CAR (hYP7) T cells. (FIG. 15B) CAR (hYP7) T cells demonstrated potent anti-tumor activity and mediated eradication of HepG2 xenograft tumors. (FIG. 15C) Tumor bioluminescence as mean photon count in mice treated in FIG. 15B. (FIG. 15D) CAR T cell persistence in xenograft tumor tissues and mice spleens after 5 weeks of treatment as measured by ddPCR.

(FIG. 16A) Experimental schematic. NSG mice bearing Hep3B orthotopic tumor were intraperitoneally or intravenously injected with 20×10⁶ CAR (hYP7) T cells on day 21. Mice were imaged weekly. (FIG. 16B) Mice treated with CAR (hYP7) T cells via tail vein demonstrated tumor eradication, while intraperitoneal treatment resulted in tumor growth inhibition. (FIG. 16C) Tumor bioluminescence as mean photon count in mice treated in FIG. 16B. (FIG. 16D) CAR T cell persistence in tumor tissues and mouse spleen after 5 weeks of treatment as measured by ddPCR. Values represent mean±SD. **p<0.01.

(FIG. 19A) Body weight of Hep3B tumor model mice after intraperitoneal injection with PBS, mock T-cells, CAR (hYP7) T cells or CAR (HN3) T cells. (FIG. 19B) Body weight of HepG2 tumor model mice after intraperitoneal injection with 20 million mock T-cells or CAR (hYP7) T cells.

SEQUENCE LISTING

Figure 1:
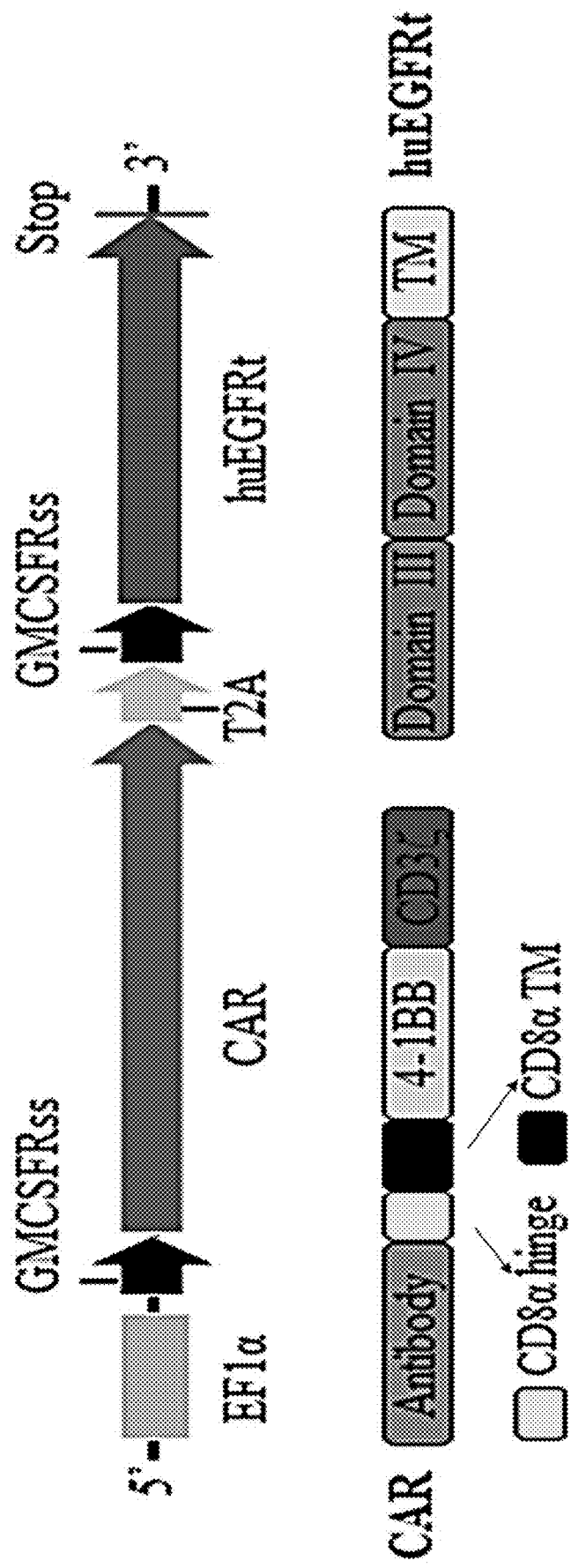
FIG. 1 is a schematic of a lentiviral construct for generating tumor-targeting chimeric antigen receptors (CARs). The lentivirus construct includes a CAR coding region and a region encoding a truncated human epidermal growth factor receptor (huEGFRt), each of which is preceded by a granulocyte-macrophage colony stimulating factor receptor signal sequence (GMCSFRss). The two regions are separated by a self-cleaving T2A sequence such that upon expression of the construct, the CAR is cleaved from huEGFRt. Expression of the construct is driven by a human elongation factor 1α (EF1α) promoter. The CAR includes an antigen-binding region, a CD8α hinge region, a CD8α transmembrane (TM) domain, a 4-1BB co-stimulatory region and a CD3ζ signaling domain. The huEGFRt includes two extracellular domains (Domain III and Domain IV) and a TM domain.

The nucleic and amino acid sequences listed in the accompanying sequence listing are shown using standard letter abbreviations for nucleotide bases, and three letter code for amino acids, as defined in 37 C.F.R. 1.822. Only one stand of each nucleic acid sequence is shown, but the complementary strand is understood as included by any reference to the displayed strand. The Sequence Listing is submitted as an ASCII text file, created May 3, 2020, 59.4 KB, which is incorporated by reference herein. In the accompanying sequence listing:

SEQ ID NO: 1 is the nucleotide sequence encoding GMCSFRss.

SEQ ID NO: 2 is the amino acid sequence of GMCSFRss.

SEQ ID NO: 3 is the nucleotide sequence encoding the CD8α hinge.

SEQ ID NO: 4 is the amino acid sequence of the CD8α hinge.

SEQ ID NO: 5 is the nucleotide sequence encoding the CD8α transmembrane domain.

SEQ ID NO: 6 is the amino acid sequence of the CD8α transmembrane domain.

SEQ ID NO: 7 is the nucleotide sequence encoding 4-1BB.

SEQ ID NO: 8 is the amino acid sequence of 4-1BB.

SEQ ID NO: 9 is the nucleotide sequence encoding CD3ζ.

SEQ ID NO: 10 is the amino acid sequence of CD3ζ.

SEQ ID NO: 11 is the nucleotide sequence encoding the self-cleaving T2A peptide.

SEQ ID NO: 12 is the amino acid sequence of the self-cleaving T2A peptide.

SEQ ID NO: 13 is the nucleotide sequence encoding huEGFRt.

SEQ ID NO: 14 is the amino acid sequence of huEGFRt.

SEQ ID NO: 15 is the nucleotide sequence encoding CAR.hYP7, with the following features:
  nucleotides 1-66=GMCSFRss coding sequence
  nucleotides 67-72=NdeI restriction site
  nucleotides 73-807=humanized YP7 scFv coding sequence
  nucleotides 808-813=SpeI restriction site
  nucleotides 814-948=CD8α hinge region coding sequence
  nucleotides 949-1011=CD8α transmembrane domain coding sequence
  nucleotides 1012-1137=4-1BB co-stimulatory domain coding sequence
  nucleotides 1138-1473=CD3ζ signaling domain coding sequence
  nucleotides 1474-1527=T2A coding sequence
  nucleotides 1528-1593=GMCSFRss coding sequence
  nucleotides 1594-2598=huEGFRt coding sequence.

SEQ ID NO: 16 is the amino acid sequence of CAR.hYP7, with the following features:
  residues 1-22=GMCSFRss
  residues 23-24=HM (encoded by the NdeI restriction site)
  residues 25-269=humanized YP7 scFv
  residues 270-271=TS (encoded by the SpeI restriction site)
  residues 272-316=CD8α hinge region
  residues 317-337=CD8α transmembrane domain
  residues 338-379=4-1BB co-stimulatory domain
  residues 380-491=CD3ζ signaling domain
  residues 492-509=self-cleaving T2A peptide
  residues 510-531=GMCSFRss
  residues 532-866=huEGFRt coding sequence.

SEQ ID NO: 17 is the nucleotide sequence encoding CAR.HN3, with the following features:
  nucleotides 1-66=GMCSFRss coding sequence
  nucleotides 67-72=NdeI restriction site
  nucleotides 73-420=HN3 coding sequence
  nucleotides 421-426=SpeI restriction site nucleotides 427-561=CD8α hinge region coding sequence
nucleotides 562-624=CD8α transmembrane domain coding sequence
nucleotides 625-750=4-1BB co-stimulatory domain coding sequence
nucleotides 751-1086=CD3ζ signaling domain coding sequence
nucleotides 1087-1140=T2A coding sequence
nucleotides 1141-1206=GMCSFRss coding sequence
nucleotides 1207-2211=huEGFRt coding sequence.

SEQ ID NO: 18 is the amino acid sequence of CAR.HN3, with the following features:
residues 1-22=GMCSFRss
residues 23-24=HM (encoded by the NdeI restriction site)
residues 25-140=HN3 single-domain antibody
residues 141-142=TS (encoded by the SpeI restriction site)
residues 143-187=CD8α hinge region
residues 188-208=CD8α transmembrane domain
residues 209-250=4-1BB co-stimulatory domain
residues 251-362=CD3ζ signaling domain
residues 363-380=self-cleaving T2A peptide
residues 381-402=GMCSFRss
residues 403-737=huEGFRt coding sequence.

SEQ ID NO: 19 is the nucleotide sequence encoding CAR.LH7, with the following features:
nucleotides 1-66=GMCSFRss coding sequence
nucleotides 67-72=NdeI restriction site
nucleotides 73-432=LH7 coding sequence
nucleotides 433-438=SpeI restriction site
nucleotides 439-573=CD8α hinge region coding sequence
nucleotides 574-636=CD8α transmembrane domain coding sequence
nucleotides 637-762=4-1BB co-stimulatory domain coding sequence
nucleotides 763-1098=CD3ζ signaling domain coding sequence
nucleotides 1099-1152=T2A coding sequence
nucleotides 1153-1218=GMCSFRss coding sequence
nucleotides 1219-2223=huEGFRt coding sequence.

SEQ ID NO: 20 is the amino acid sequence of the CAR.LH7, with the following features:
residues 1-22=GMCSFRss
residues 23-24=HM (encoded by the NdeI restriction site)
residues 25-144=LH7 single-domain antibody
residues 145-146=TS (encoded by the SpeI restriction site)
residues 147-191=CD8α hinge region
residues 192-212=CD8α transmembrane domain
residues 213-254=4-1BB co-stimulatory domain
residues 255-366=CD3ζ signaling domain
residues 367-384=self-cleaving T2A peptide
residues 385-406=GMCSFRss
residues 407-741=huEGFRt coding sequence.

SEQ ID NO: 21 is the nucleotide sequence of the YP7 VH domain.
SEQ ID NO: 22 is the amino acid sequence of the YP7 VH domain.
SEQ ID NO: 23 is the nucleotide sequence of the YP7 VL domain.
SEQ ID NO: 24 is the amino acid sequence of the YP7 VL domain.
SEQ ID NO: 25 is the nucleotide sequence of the hYP7 VH domain.
SEQ ID NO: 26 is the amino acid sequence of the hYP7 VH domain.
SEQ ID NO: 27 is the nucleotide sequence of the hYP7 VL domain.
SEQ ID NO: 28 is the amino acid sequence of the hYP7 VL domain.
SEQ ID NO: 29 is the nucleotide sequence of the HN3 single-domain antibody.
SEQ ID NO: 30 is the amino acid sequence of the HN3 single-domain antibody.
SEQ ID NO: 31 is the nucleotide sequence of the LH7 single-domain antibody.
SEQ ID NO: 32 is the amino acid sequence of the LH7 single-domain antibody.
SEQ ID NO: 33 is the nucleotide sequence of the LH4 single-domain antibody.
SEQ ID NO: 34 is the amino acid sequence of the LH4 single-domain antibody.
SEQ ID NO: 35 is the nucleotide sequence of the LH6 single-domain antibody.
SEQ ID NO: 36 is the amino acid sequence of the LH6 single-domain antibody.
SEQ ID NO: 37 is the nucleotide sequence of the YP218 VH domain.
SEQ ID NO: 38 is the amino acid sequence of the YP218 VH domain.
SEQ ID NO: 39 is the nucleotide sequence of the YP218 VL domain.
SEQ ID NO: 40 is the amino acid sequence of the YP218 VL domain.
SEQ ID NO: 41 is the nucleotide sequence of the SD1 single-domain antibody.
SEQ ID NO: 42 is the amino acid sequence of the SD1 single-domain antibody.
SEQ ID NOs: 43-51 are sgRNA sequences.

DETAILED DESCRIPTION

I. Abbreviations

ADCC antibody-dependent cell-mediated cytotoxicity
CAR chimeric antigen receptor
CDR complementarity determining region
CTL cytotoxic T lymphocyte
ddPCR droplet digital PCR
DMEM Dulbecco's modified Eagle medium
EF1α elongation factor 1 alpha
EGF epidermal growth factor
EGFR epidermal growth factor receptor
ELISA enzyme-linked immunosorbent assay
FACS fluorescence activated cells sorting
FBS fetal bovine serum
GPC2 glypican-2
GPC3 glypican-3
GMCSFRss granulocyte-macrophage colony stimulating factor receptor signal sequence
HCC hepatocellular carcinoma
HLA human leukocyte antigen
huEGFRt human truncated epidermal growth factor receptor
IFN interferon
Ig immunoglobulin
IL interleukin
i.p. intraperitoneal
ITAM immunoreceptor tyrosine-based activation motif
PBMC peripheral blood mononuclear cell
PBS phosphate-buffered saline scFv single-chain variable fragment
TM transmembrane
VH or $V_H$ variable heavy
VL or $V_L$ variable light
YST yolk sac tumor II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

4-1BB: A co-stimulatory molecule expressed by T cell receptor (TCR)-activated lymphocytes, and by other cells including natural killer cells. Ligation of 4-1BB induces a signaling cascade that results in cytokine production, expression of anti-apoptotic molecules and an enhanced immune response.

Acute lymphoblastic leukemia (ALL): An acute form of leukemia characterized by the overproduction of lymphoblasts. ALL is most common in childhood, peaking at ages 2-5.

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light ($V_L$) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE. Antibody isotypes not found in mammals include IgX, IgY, IgW and IgNAR. IgY is the primary antibody produced by birds and reptiles, and has some functionally similar to mammalian IgG and IgE. IgW and IgNAR antibodies are produced by cartilaginous fish, while IgX antibodies are found in amphibians.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (*JMB* 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online A "single-domain antibody" refers to an antibody having a single domain (a variable domain) that is capable of specifically binding an antigen, or an epitope of an antigen, in the absence of an additional antibody domain. Single-domain antibodies include, for example, $V_H$ domain antibodies, $V_{NAR}$ antibodies, camelid $V_HH$ antibodies, and $V_L$ domain antibodies. $V_{NAR}$ antibodies are produced by cartilaginous fish, such as nurse sharks, wobbegong sharks, spiny dogfish and bamboo sharks. Camelid $V_HH$ antibodies are produced by several species including camel, llama, alpaca, dromedary, and guanaco, which produce heavy chain antibodies that are naturally devoid of light chains.

A "monoclonal antibody" is an antibody produced by a single clone of lymphocytes or by a cell into which the coding sequence of a single antibody has been transfected. Monoclonal antibodies are produced by methods known to those of skill in the art. Monoclonal antibodies include humanized monoclonal antibodies.

A "chimeric antibody" has framework residues from one species, such as human, and CDRs (which generally confer antigen binding) from another species.

A "humanized" antibody is an immunoglobulin including a human framework region and one or more CDRs from a non-human (for example a mouse, rabbit, rat, shark or synthetic) immunoglobulin. The non-human immunoglobulin providing the CDRs is termed a "donor," and the human immunoglobulin providing the framework is termed an "acceptor." In one embodiment, all CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A humanized antibody binds to the same antigen as the donor antibody that provides the CDRs. Humanized or other monoclonal antibodies can have additional conservative amino acid substitutions which have substantially no effect on antigen binding or other immunoglobulin functions.

Binding affinity: Affinity of an antibody for an antigen. In one embodiment, affinity is calculated by a modification of the Scatchard method described by Frankel et al., Mol. Immunol., 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In another embodiment, antibody affinity is measured by flow cytometry. An antibody that "specifically binds" an antigen (such as GPC3) is an antibody that binds the antigen with high affinity and does not significantly bind other unrelated antigens.

Breast cancer: A type of cancer that forms in tissues of the breast, usually the ducts (tubes that carry milk to the nipple) and lobules (glands that make milk). Triple negative breast cancer refers to a type of breast cancer in which the cancer cells do not express estrogen receptors, progesterone receptors or significant levels of HER2/neu protein. Triple negative breast cancer is also called ER-negative PR-negative HER2/neu-negative breast cancer.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of a CAR T cell used in combination with a radioactive or chemical compound.

Chimeric antigen receptor (CAR): A chimeric molecule that includes an antigen-binding portion (such as a single domain antibody or scFv) and a signaling domain, such as a signaling domain from a T cell receptor (e.g. CD3ζ). Typically, CARs are comprised of an antigen-binding moiety, a transmembrane domain and an intracellular domain. The intracellular domain typically includes a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28, 4-1BB (CD137), ICOS, OX40 (CD134), CD27 and/or DAP10.

Cholangiocarcinoma: A type of cancer that develops in cells that line the bile ducts in the liver.

Complementarity determining region (CDR): A region of hypervariable amino acid sequence that defines the binding affinity and specificity of an antibody. The light and heavy chains of a mammalian immunoglobulin each have three CDRs, designated L-CDR1, L-CDR2, L-CDR3 and H-CDR1, H-CDR2, H-CDR3, respectively.

Conservative variant: "Conservative" amino acid substitutions are those substitutions that do not substantially affect or decrease the affinity of a protein, such as an antibody to GPC3. As one example, a monoclonal antibody that specifically binds GPC3 can include at most about 1, at most about 2, at most about 5, and most about 10, or at most about 15 conservative substitutions and specifically bind the GPC3 polypeptide. The term "conservative variant" also includes the use of a substituted amino acid in place of an unsubstituted parent amino acid, provided that the variant retains activity. Non-conservative substitutions are those that reduce an activity of a protein.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In some embodiments herein, provided are amino acid sequences comprising no more than 10, no more than 9, no more than 8, no more than 7, no more than 6, no more than 5, no more than 4, no more than 3, no more than 2 or no more than 1 amino acid substitutions relative to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30 or SEQ ID NO: 32.

Cytotoxic agent: Any drug or compound that kills cells.

Cytotoxicity: The toxicity of a molecule to the cells intended to be targeted, as opposed to the cells of the rest of an organism.

Degenerate variant: A polynucleotide encoding a polypeptide that includes a sequence that is degenerate as a result of the genetic code. There are 20 natural amino acids, most of which are specified by more than one codon. Therefore, all degenerate nucleotide sequences are included as long as the amino acid sequence of the polypeptide is unchanged.

Desmoplastic small round cell tumor (DRCT): A soft tissue sarcoma that predominantly occurs in childhood, particularly in boys. DRCT is an aggressive and rare type of cancer that primarily occurs as a masses in the abdomen, but can also be found in the lymph nodes, the lining of the abdomen, diaphragm, spleen, liver, chest wall, skull, spinal cord, intestine, bladder, brain, lungs, testicles, ovaries and the pelvis.

Epitope: An antigenic determinant. These are particular chemical groups or peptide sequences on a molecule that are antigenic, i.e. that elicit a specific immune response. An antibody specifically binds a particular antigenic epitope on a polypeptide.

Ewing's sarcoma: A rare type of malignant tumor found in bone or soft tissue. Ewing's sarcoma is a small, blue, round cell tumor.

Framework region: Amino acid sequences interposed between CDRs. Framework regions include variable light and variable heavy framework regions. The framework regions serve to hold the CDRs in an appropriate orientation for antigen binding.

Fusion protein: A protein comprising at least a portion of two different (heterologous) proteins.

Glypican-2 (GPC2): A member of the six-member glypican family of heparan sulfate (HS) proteoglycans that are attached to the cell surface by a GPI anchor (Filmus et al., *Genome Biol* 9:224, 2008). GPC2 is uniquely expressed in the nervous system (Stipp et al., *J Cell Biol* 124:149-160, 1994), participates in cell adhesion and is thought to regulate the growth and guidance of axons. In addition, GPC2 mRNA is highly expressed in neuroblastoma and other pediatric cancers (Orentas et al., *Front Oncol* 2:194, 2012). GPC2 is also known as cerebroglycan proteoglycan and glypican proteoglycan 2. GPC2 genomic, mRNA and protein sequences are publically available (see, for example, NCBI Gene ID 221914).

GPC2-positive cancer: A cancer that overexpresses GPC2. Examples of GPC2-positive cancers include, but are not limited to, neuroblastoma, acute lymphoblastic leukemia, embryonal rhabdomyosarcoma, alveolar rhabdomyosarcoma, Ewing's sarcoma, desmoplastic small round cell tumor or osteosarcoma.

Glypican-3 (GPC3): A member of the glypican family of heparan sulfate (HS) proteoglycans that are attached to the cell surface by a glycosylphosphatidylinositol anchor (Filmus and Selleck, *J Clin Invest* 108:497-501, 2001). The GPC3 gene codes for a core protein of approximately 70 kD, which can be cleaved by furin to produce an N-terminal 40 kD fragment and a C-terminal 30 kD fragment. Two HS chains are attached on the C-terminal portion of GPC3. GPC3 and other glypican family proteins play a role in cell division and cell growth regulation. GPC3 is highly expressed in HCC and some other human cancers including melanoma, squamous cell carcinomas of the lung, and clear cell carcinomas of the ovary (Ho and Kim, *Eur J Cancer* 47(3):333-338, 2011), but is not expressed in normal tissues. GPC3 is also known as SGB, DGSX, MXR7, SDYS, SGBS, OCI-5, SGBS1 and GTR2-2.

There are four known isoforms of human GPC3 (isoforms 1-4). Nucleic acid and amino acid sequences of the four isoforms of GPC3 are known, including GenBank Accession numbers: NM_001164617 and NP_001158089 (isoform 1); NM_004484 and NP_004475 (isoform 2); NM_001164618 and NP_001158090 (isoform 3); and NM_001164619 and NP_001158091 (isoform 4).

GPC3-positive cancer: A cancer that overexpresses GPC3. Examples of GPC3-positive cancers include, but are not limited to, HCC, melanoma, ovarian clear-cell carcinomas, yolk sac tumors (YST), neuroblastoma, hepatoblastoma, Wilms' tumors, squamous cell carcinoma of the lung, testicular nonseminomatous germ cell tumors, liposarcoma, cervical intraepithelial neoplasia, adenoma of the adrenal gland, schwannoma and embryonal tumors (Ho and Kim, *Eur J Cancer* 47(3):333-338, 2011; Baumhoer et al., *Am J Clin Pathol* 129(6):899-906, 2008; Saikali and Sinnett, *Int J Cancer* 89(5):418-422, 2000).

HAMA (human anti-murine antibody) response: An immune response in a human subject to the variable and constant regions of a murine antibody that has been administered to the patient. Repeated antibody administration may lead to an increased rate of clearance of the antibody from the patient's serum and may also elicit allergic reactions in the patient.

Hepatocellular carcinoma (HCC): A primary malignancy of the liver typically occurring in patients with inflammatory livers resulting from viral hepatitis, liver toxins or hepatic cirrhosis (often caused by alcoholism). HCC is also called malignant hepatoma.

Heterologous: Originating from a separate genetic source or species.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ nd $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Lung cancer: Cancer that forms in tissues of the lung, usually in the cells lining air passages. The two main types are small cell lung cancer and non-small cell lung cancer (NSCLC). These types are diagnosed based on how the cells look under a microscope.

Mammal: This term includes both human and non-human mammals. Similarly, the term "subject" includes both human and veterinary subjects.

Melanoma: A form of cancer that originates in melanocytes (cells that make the pigment melanin). Melanocytes are found primary in the skin, but are also present in the bowel and eye. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism) which is a marker of aggressive behavior and a tendency to local recurrence. Other melanomas include clear cell sarcoma, mucosal melanoma and uveal melanoma.

Mesothelin: A 40 kDa cell-surface glycosylphosphatidylinositol (GPI)-linked glycoprotein. The human mesothelin protein is synthesized as a 70 kD precursor which is then proteolytically processed. The 30 kD amino terminus of mesothelin is secreted and is referred to as megakaryocyte potentiating factor (Yamaguchi et al., *J. Biol. Chem.* 269:805 808, 1994). The 40 kD carboxyl terminus remains bound to the membrane as mature mesothelin (Chang et al., *Natl. Acad. Sci. USA* 93:136 140, 1996). Exemplary nucleic acid and amino acid sequences of mesothelin are as described in PCT Publication No. WO 97/25,068; U.S. Pat. No. 6,083, 502; Chang and Pastan, *Int. J. Cancer* 57:90, 1994; Chang and Pastan, *Proc. Natl. Acad. Sci USA* 93:136, 1996; Brinkmann et al., *Int. J. Cancer* 71:638, 1997; and Chowdhury et al., *Mol. Immunol.* 34:9, 1997. Mesothelin also refers to mesothelin proteins or polypeptides which remain intracellular as well as secreted and/or isolated extracellular mesothelin protein.

Mesothelin-positive cancer: A cancer that overexpresses mesothelin. Examples of mesothelin-positive cancers include, but are not limited to, mesothelioma, prostate cancer, lung cancer, stomach cancer, squamous cell carcinoma, pancreatic cancer, cholangiocarcinoma, triple negative breast cancer and ovarian cancer.

Mesothelioma: A type of neoplasm derived from the lining cells of the pleura and peritoneum which grows as a thick sheet covering the viscera, and is composed of spindle cells or fibrous tissue which may enclose gland-like spaces lined by cuboidal cells. Mesotheliomas often originate in the tissue lining the lung, heart or abdomen. In some cases, mesotheliomas are caused by exposure to asbestos.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Neuroblastoma: A solid tumor arising from embryonic neural crest cells. Neuroblastoma commonly arises in and around the adrenal glands, but can occur anywhere that sympathetic neural tissue is found, such as in the abdomen, chest, neck or nerve tissue near the spine. Neuroblastoma typically occurs in children younger than 5 years of age.

Operably linked A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Osteosarcoma: A type of cancerous tumor found in the bone. Osteosarcoma is an aggressive cancer arising from primitive transformed cells of mesenchymal origin. This type of cancer is most prevalent in children and young adults.

Ovarian cancer: Cancer that forms in tissues of the ovary (one of a pair of female reproductive glands in which the ova, or eggs, are formed). Most ovarian cancers are either ovarian epithelial carcinomas (cancer that begins in the cells on the surface of the ovary) or malignant germ cell tumors (cancer that begins in egg cells).

Ovarian clear cell carcinoma: A distinct histopathologic subtype of epithelial ovarian cancer with an incidence of less than 5% of all ovarian malignancies. When viewed under a microscope, the insides of the cells of this type of tumor appear clear.

Pancreatic cancer: A disease in which malignant (cancer) cells are found in the tissues of the pancreas. Also called exocrine cancer.

Pediatric cancer: A cancer that develops in children ages 0 to 14. The major types of pediatric cancers include, for example, neuroblastoma, acute lymphoblastic leukemia (ALL), embryonal rhabdomyosarcoma (ERMS), alveolar rhabdomyosarcoma (ARMS), Ewing's sarcoma, desmoplastic small round cell tumor (DRCT), osteosarcoma, brain and other CNS tumors, Wilm's tumor, non-Hodgkin lymphoma, and retinoblastoma.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Prostate cancer: Cancer that forms in tissues of the prostate (a gland in the male reproductive system found below the bladder and in front of the rectum). Prostate cancer usually occurs in older men.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Rhabdomyosarcoma (RMS): A soft tissue malignant tumor of skeletal muscle origin. The most common primary sites for rhabdomyosarcoma are the head and neck (e.g., parameningeal, orbit, pharyngeal, etc.), the genitourinary tract, and the extremities. Other less common primary sites include the trunk, chest wall, the abdomen (including the retroperitoneum and biliary tract), and the perineal/anal region. There are at least two types of RMS; the most common forms are alveolar RMS (ARMS) and embryonal histological RMS (ERMS). Approximately 20% of children with rhabdomyosarcoma have the ARMS subtype. An increased frequency of this subtype is noted in adolescents and in patients with primary sites involving the extremities, trunk, and perineum/perianal region. ARMS is associated with chromosomal translocations encoding a fusion gene involving FKHR on chromosome 13 and members of the PAX family. The embryonal subtype is the most frequently observed subtype in children, accounting for approximately 60-70% of rhabdomyosarcomas of childhood. Tumors with embryonal histology typically arise in the head and neck region or in the genitourinary tract, although they may occur at any primary site. ERMS is characterized by a younger age at diagnosis, loss of heterozygosity, and altered genomic imprinting.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy, such as a tumor tissue biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a GPC3 polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Squamous cell carcinoma: A type of cancer that originates in squamous cells, thin, flat cells that form the surface of the skin, eyes, various internal organs, and the lining of hollow organs and ducts of some glands. Squamous cell carcinoma is also referred to as epidermoid carcinoma. One type of squamous cell carcinoma is squamous cell carcinoma of the lung. Squamous cell carcinoma is the most common type of skin cancer.

Stomach cancer: Cancer that forms in tissues lining the stomach. Also called gastric cancer.

Subject: Living multi-cellular vertebrate organisms, a category that includes both human and veterinary subjects, including human and non-human mammals.

Synthetic: Produced by artificial means in a laboratory, for example a synthetic nucleic acid or protein (for example, an antibody) can be chemically synthesized in a laboratory.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control.

19

In addition, the materials, methods, and examples are illustrative only and not intended to be limiting.

III. Overview of Several Embodiments

Disclosed herein are nucleic acid molecules that encode both a chimeric antigen receptor (CAR) and a truncated human epidermal growth factor receptor (huEGFRt). The encoded CARs include a tumor antigen-specific monoclonal antibody fused to an extracellular hinge region, a transmembrane region, an intracellular co-stimulatory domain and an intracellular signaling domain. The huEGFRt includes two EGFR extracellular domains (Domain III and Domain IV) and the transmembrane domain, but lacks the two membrane distal extracellular domains (Domain I and Domain II) and all intracellular domains (the juxtamembrane domain, the tyrosine kinase domain and the C-terminal tail). Isolated cells, such as T lymphocytes, that co-express the disclosed CARs and huEGFRt are also provided. T cells transduced with the CAR constructs can be used for cancer immunotherapy.

Provided herein is a nucleic acid molecule encoding a CAR and a huEGFRt. In some embodiments, the nucleic acid comprises in the 5' to 3' direction a nucleic acid encoding a first signal sequence; a nucleic acid encoding an antigen-specific antibody or antigen-binding fragment thereof; a nucleic acid encoding an extracellular hinge region; a nucleic acid encoding a transmembrane domain; a nucleic acid encoding an intracellular co-stimulatory domain; a nucleic acid encoding a intracellular signaling domain; a nucleic acid encoding a self-cleaving 2A peptide; a nucleic acid encoding a second signal sequence; and a nucleic acid encoding a huEGFRt.

The first and second signal sequence can be any suitable signal sequence known in the art. The first and second signal sequences can be the same signal sequence or they can be different signal sequences. In some embodiments, the first and/or second signal sequence is a granulocyte-macrophage colony stimulating factor receptor signal sequence (GMCSFRss).

In some embodiments, the extracellular hinge region comprises a CD8α hinge region, a CD28 hinge region or a sequence from another immunoglobulin molecule such an IgG1, IgG4 or IgD (for example a CH2 and/or CH3 domain from an immunoglobulin molecule). The hinge region is sometimes referred to in the art as a "spacer region."

In some embodiments, the transmembrane domain comprises a CD8α, CD28, CD3ε, CD45, CD4, CD5, CD9, CD16, CD22, CD33, CD37, CD64, CD80, CD86, CD134, CD137 or CD154 transmembrane domain. The transmembrane domain may also be the transmembrane region of the alpha, beta or zeta chain of the T cell receptor.

In some embodiments, the intracellular co-stimulatory domain comprises a 4-1BB (CD137, TNFRSF9), CD28, ICOS, OX40 (CD134), CD27, CD30, CD40, PD-1, lymphocyte function-associated antigen 1 (LFA-1), CD2, CD7, LIGHT, NKG2C, B7-H3 or DAP10 co-stimulatory domain. In some examples, the intracellular co-stimulatory domain comprises 4-1BB and CD28.

In some embodiments, the intracellular signaling domain is a domain having an immunoreceptor tyrosine-based activation motif (ITAM), for example a CD3ζ or FcεRIγ signaling domain.

In particular embodiments, the first and second signal sequences comprise a GMCSFRss, the extracellular hinge region comprises a CD8α hinge region, the transmembrane domain comprises a CD8α transmembrane domain, the intracellular co-stimulatory domain comprises a 4-1BB co-stimulatory domain and the intracellular signaling domain comprises a CD3ζ signaling domain.

In some examples, the nucleic acid encoding the CD8α hinge comprises a nucleotide sequence at least 90%, at least 95%, at least 96%, at least 97%, at least 98% or at least 99% identical to SEQ ID NO: 3. In one non-limiting example, the nucleic acid encoding the CD8α hinge comprises the sequence of SEQ ID NO: 3.

In some examples, the nucleic acid encoding the CD8α transmembrane domain comprises a nucleotide sequence at least 90%, at least 95%, at least 96%, at least 97%, at least 98% or at least 99% identical to SEQ ID NO: 5. In one non-limiting example, the nucleic acid encoding the CD8α transmembrane domain comprises the sequence of SEQ ID NO: 5.

In some examples, the nucleic acid molecule encoding the 4-1BB co-stimulatory domain comprises a nucleotide sequence at least 90%, at least 95%, at least 96%, at least 97%, at least 98% or at least 99% identical to SEQ ID NO: 7. In one non-limiting example, the nucleic acid molecule encoding the 4-1BB co-stimulatory domain comprises the sequence of SEQ ID NO: 7.

In some examples, the nucleic acid encoding the CD3ζ signaling domain comprises a nucleotide sequence at least 90%, at least 95%, at least 96%, at least 97%, at least 98% or at least 99% identical to SEQ ID NO: 9. In one non-limiting example, the nucleic acid encoding the CD3ζ signaling domain comprises the sequence of SEQ ID NO: 9.

In some examples, the nucleic acid encoding the first GMCSFRss and the nucleic acid encoding the second GMCSFRss each comprise a nucleotide sequence at least 90%, at least 95%, at least 96%, at least 97%, at least 98% or at least 99% identical to SEQ ID NO: 1. In one non-limiting example, the nucleic acid encoding the first GMCSFRss and the nucleic acid encoding the second GMCSFRss each comprise the sequence of SEQ ID NO: 1.

In some examples, the self-cleaving 2A peptide is a *Thosea asigna* virus 2A (T2A) peptide. In other examples, the self-cleaving 2A peptide is a foot and mouth disease virus 2A (F2A) peptide, an equine rhinitis A virus 2A (E2A) peptide, or a porcine teschovirus-1 2A (P2A) peptide. In particular examples, the nucleic acid encoding the self-cleaving T2A peptide comprises a nucleotide sequence at least 90%, at least 95%, at least 96%, at least 97%, at least 98% or at least 99% identical to SEQ ID NO: 11. In one non-limiting example, the nucleic acid encoding the self-cleaving T2A peptide comprises the sequence of SEQ ID NO: 11.

In some examples, the nucleic acid encoding the huEGFRt comprises a nucleotide sequence at least 90%, at least 95%, at least 96%, at least 97%, at least 98% or at least 99% identical to SEQ ID NO: 13. In one non-limiting example, the nucleic acid encoding the huEGFRt comprises the sequence of SEQ ID NO: 13.

In some embodiments, the nucleic acid molecule further includes a human elongation factor 1α (EF1α) promoter sequence 5' of the nucleic acid encoding the first GMCSFRss. However, any suitable promoter sequence can be selected by one of skill in the art.

In some embodiments, the antigen-binding fragment is a single-chain variable fragment (scFv) or a single-domain antibody.

In some embodiments, the antibody or antigen-binding fragment specifically binds a tumor antigen. In particular examples, the tumor antigen is GPC3, GPC2 or mesothelin.

In some examples where the tumor antigen is GPC3, the nucleic acid encoding the antibody-binding fragment comprises the variable heavy (VH) domain complementarity determining region 1 (CDR1), CDR2 and CDR3 nucleic acid sequences of SEQ ID NO: 25 (the hYP7 VH domain nucleotide sequence) and the variable light (VL) domain CDR1, CDR2 and CDR3 nucleic acid sequences of SEQ ID NO: 27 (the hYP7 VL domain nucleotide sequence). The CDR sequences can be determined using any well-known numbering schemes, such as IMGT, Kabat or Chothia. In particular examples, the VH domain CDR1, CDR2 and CDR3 nucleic acid sequences respectively comprise nucleotides 91-105, 148-204 and 301-318 of SEQ ID NO: 25; and/or the VL domain CDR1, CDR2 and CDR3 nucleic acid sequences respectively comprise nucleotides 70-120, 166-186 and 283-309 of SEQ ID NO: 27. In other particular examples, the VH domain CDR1, CDR2 and CDR3 nucleic acid sequences respectively comprise nucleotides 76-99, 151-180 and 295-318 of SEQ ID NO: 25; and/or the VL domain CDR1, CDR2 and CDR3 nucleic acid sequences respectively comprise nucleotides 79-114, 166-174 and 283-309 of SEQ ID NO: 27. In one non-limiting example, the nucleic acid encoding the antibody-binding fragment comprises the sequence of nucleotides 73-807 of SEQ ID NO: 15.

In other examples where the tumor antigen is GPC3, the nucleic acid encoding the antibody-binding fragment comprises the CDR1, CDR2 and CDR3 nucleic acid sequences of SEQ ID NO: 29 (the HN3 single-domain antibody nucleotide sequence). The CDR sequences can be determined using any well-known numbering schemes, such as IMGT, Kabat or Chothia. In particular examples, the CDR1, CDR2 and CDR3 nucleic acid sequences respectively comprise nucleotides 91-105, 148-195 and 286-315 of SEQ ID NO: 29. In other particular examples, the CDR1, CDR2 and CDR3 nucleic acid sequences respectively comprise nucleotides 76-99, 151-171 and 286-315 of SEQ ID NO: 29. In one non-limiting example, the nucleic acid encoding the antibody-binding fragment comprises the sequence of nucleotides 73-420 of SEQ ID NO: 17.

In yet other examples, where the tumor antigen is GPC3, the nucleic acid encoding the antibody-binding fragment comprises the CDR nucleic acid sequences of a GPC3-specific monoclonal antibody disclosed in WO 2013/181543 or WO 2012/145469, which are incorporated herein by reference in their entirety.

In some examples where the tumor antigen is GPC2, the nucleic acid encoding the antibody-binding fragment comprises the CDR1, CDR2 and CDR3 nucleic acid sequences of SEQ ID NO: 31 (the LH7 single-domain antibody nucleotide sequence). The CDR sequences can be determined using any well-known numbering schemes, such as IMGT, Kabat or Chothia. In particular examples, the CDR1, CDR2 and CDR3 nucleic acid sequences respectively comprise nucleotides 91-105, 148-195 and 286-327 of SEQ ID NO: 31. In other particular examples, the CDR1, CDR2 and CDR3 nucleic acid sequences respectively comprise nucleotides 76-99, 151-171 and 286-327 of SEQ ID NO: 31. In one non-limiting example, the nucleic acid encoding the antibody-binding fragment comprises the sequence of nucleotides 73-432 of SEQ ID NO: 19.

In other examples where the tumor antigen is GPC2, the nucleic acid encoding the antibody-binding fragment comprises the CDR1, CDR2 and CDR3 nucleic acid sequences of SEQ ID NO: 33 (the LH4 single-domain antibody nucleotide sequence). The CDR sequences can be determined using any well-known numbering schemes, such as IMGT, Kabat or Chothia. In particular examples, the CDR1, CDR2 and CDR3 nucleic acid sequences respectively comprise nucleotides 91-105, 148-195 and 286-327 of SEQ ID NO: 33. In other particular examples, the CDR1, CDR2 and CDR3 nucleic acid sequences respectively comprise nucleotides 76-99, 151-171 and 286-327 of SEQ ID NO: 33.

In other examples where the tumor antigen is GPC2, the nucleic acid encoding the antibody-binding fragment comprises the CDR1, CDR2 and CDR3 nucleic acid sequences of SEQ ID NO: 35 (the LH6 single-domain antibody nucleotide sequence). The CDR sequences can be determined using any well-known numbering schemes, such as IMGT, Kabat or Chothia. In particular examples, the CDR1, CDR2 and CDR3 nucleic acid sequences respectively comprise nucleotides 91-105, 148-198 and 289-330 of SEQ ID NO: 35. In other particular examples, the CDR1, CDR2 and CDR3 nucleic acid sequences respectively comprise nucleotides 76-99, 151-174 and 289-330 of SEQ ID NO: 35.

In yet other examples, where the tumor antigen is GPC2, the nucleic acid encoding the antibody-binding fragment comprises the CDR nucleic acid sequences of a GPC2-specific monoclonal antibody disclosed in Li et al., *Proc Natl Acad Sci USA* 114(32):E6623-E6631, 2017.

In some examples where the tumor antigen is mesothelin, the nucleic acid encoding the antibody-binding fragment comprises the VH domain CDR1, CDR2 and CDR3 nucleic acid sequences of SEQ ID NO: 37 (the YP218 VH domain nucleotide sequence) and the VL domain CDR1, CDR2 and CDR3 nucleic acid sequences of SEQ ID NO: 39 (the YP218 VL domain nucleotide sequence). The CDR sequences can be determined using any well-known numbering schemes, such as IMGT, Kabat or Chothia. In particular examples, the VH domain CDR1, CDR2 and CDR3 nucleic acid sequences respectively comprise nucleotides 91-108, 101-204 and 298-336 of SEQ ID NO: 37; and/or the VL domain CDR1, CDR2 and CDR3 nucleic acid sequences respectively comprise nucleotides 70-102, 148-168 and 265-303 of SEQ ID NO: 39. In other particular examples, the VH domain CDR1, CDR2 and CDR3 nucleic acid sequences respectively comprise nucleotides 79-102, 154-177 and 292-336 of SEQ ID NO: 37; and/or the VL domain CDR1, CDR2 and CDR3 nucleic acid sequences respectively comprise nucleotides 79-96, 148-156 and 265-303 of SEQ ID NO: 39.

In other examples where the tumor antigen is mesothelin, the nucleic acid encoding the antibody-binding fragment comprises the CDR1, CDR2 and CDR3 nucleic acid sequences of SEQ ID NO: 41 (the SD1 single-domain antibody nucleotide sequence). The CDR sequences can be determined using any well-known numbering schemes, such as IMGT, Kabat or Chothia. In particular examples, the CDR1, CDR2 and CDR3 nucleic acid sequences respectively comprise nucleotides 91-105, 151-198 and 295-306 of SEQ ID NO: 41. In other particular examples, the CDR1, CDR2 and CDR3 nucleic acid sequences respectively comprise nucleotides 78-105, 151-174 and 289-309 of SEQ ID NO: 41. Further provided herein are vectors that include a CAR-encoding nucleic acid molecule disclosed herein. In some embodiments, the vector is a viral vector, such as, but not limited to, a lentiviral vector.

In yet other examples, where the tumor antigen is mesothelin, the nucleic acid encoding the antibody-binding fragment comprises the CDR nucleic acid sequences of a mesothelin-specific monoclonal antibody disclosed in WO 2014/031476, WO 2014/052064, U.S. Pat. No. 8,460,660, 6,809,184 or 7,081,518, each of which are incorporated herein by reference in their entirety.

Also provided are isolated host cells that include a CAR-encoding nucleic acid molecule disclosed herein. In some embodiments, the isolated host cells are T lymphocytes.

The present disclosure further provides isolated host cells that co-express a chimeric antigen receptor (CAR) and a truncated human epidermal growth factor receptor (huEGFRt). In some embodiments, the CAR includes an antigen-specific antibody or antigen-binding fragment thereof, an extracellular hinge region, a transmembrane domain, an intracellular co-stimulatory domain and an intracellular signaling domain; and/or the huEGFRt comprises a Domain III, a Domain IV and a transmembrane domain from human EGFR, but lacks an epidermal growth factor (EGF)-binding domain and a cytoplasmic domain.

In some embodiments, the extracellular hinge region comprises a CD8α hinge region, a CD28 hinge region or a sequence from another immunoglobulin molecule such an IgG1, IgG4 or IgD (for example a CH2 and/or CH3 domain from an immunoglobulin molecule).

In some embodiments, the transmembrane domain comprises a CD8α, CD28, CD3ε, CD45, CD4, CD5, CD9, CD16, CD22, CD33, CD37, CD64, CD80, CD86, CD134, CD137 or CD154 transmembrane domain. The transmembrane domain may also be the transmembrane region of the alpha, beta or zeta chain of the T cell receptor.

In some embodiments, the intracellular co-stimulatory domain comprises a 4-1BB (CD137, TNFRSF9), CD28, ICOS, OX40 (CD134), CD27, CD30, CD40, PD-1, lymphocyte function-associated antigen 1 (LFA-1), CD2, CD7, LIGHT, NKG2C, B7-H3 or DAP10 co-stimulatory domain.

In some embodiments, the intracellular signaling domain is a domain having an ITAM, for example a CD3ζ or FcεRIγ signaling domain.

In particular embodiments, the extracellular hinge region comprises a CD8α hinge region, the transmembrane domain comprises a CD8α transmembrane domain, the intracellular co-stimulatory domain comprises a 4-1BB co-stimulatory domain and the intracellular signaling domain comprises a CD3ζ signaling domain.

In some examples, the amino acid sequence of the CD8α hinge region is at least 90%, at least 95%, at least 96%, at least 97%, at least 98% or at least 99% identical to SEQ ID NO: 4. In particular examples, the amino acid sequence of the CD8α hinge region comprises SEQ ID NO: 4.

In some examples, the amino acid sequence of the CD8α transmembrane domain is at least 90%, at least 95%, at least 96%, at least 97%, at least 98% or at least 99% identical to SEQ ID NO: 6. In particular examples, the amino acid sequence of the CD8α transmembrane domain comprises SEQ ID NO: 6.

In some examples, the amino acid sequence of the 4-1BB co-stimulatory domain is at least 90%, at least 95%, at least 96%, at least 97%, at least 98% or at least 99% identical to SEQ ID NO: 8. In particular examples, the amino acid sequence of the 4-1BB co-stimulatory domain comprises SEQ ID NO: 8.

In some examples, the amino acid sequence of the CD3ζ signaling domain is at least 90%, at least 95%, at least 96%, at least 97%, at least 98% or at least 99% identical to SEQ ID NO: 10. In particular examples, the amino acid sequence of the CD3ζ signaling domain comprises SEQ ID NO: 10.

In some examples, the amino acid sequence of the huEGFRt is at least 90%, at least 95%, at least 96%, at least 97%, at least 98% or at least 99% identical to SEQ ID NO: 14. In particular examples, the amino acid sequence of the huEGFRt comprises SEQ ID NO: 14.

In some embodiments, the antigen-binding fragment is a scFv or a single-domain antibody.

In some embodiments, the antibody or antigen-binding fragment specifically binds a tumor antigen. In some examples, the tumor antigen is GPC3, GPC2 or mesothelin.

In some examples where the tumor antigen is GPC3, the amino acid sequence of the antigen-binding fragment comprises the VH domain CDR1, CDR2 and CDR3 sequences of SEQ ID NO: 26 (hYP7 VH domain) and the VL domain CDR1, CDR2 and CDR3 sequences of SEQ ID NO: 28 (hYP7 VL domain). The CDR sequences can be determined using any well-known numbering schemes, such as IMGT, Kabat or Chothia. In particular examples, the VH domain CDR1, CDR2 and CDR3 amino acid sequences respectively comprise residues 31-35, 50-68 and 101-106 of SEQ ID NO: 26 and/or the VL domain CDR1, CDR2 and CDR3 amino acid sequences respectively comprise residues 24-40, 56-62 and 95-103 of SEQ ID NO: 28. In other particular examples, the VH domain CDR1, CDR2 and CDR3 amino acid sequences respectively comprise residues 26-33, 51-60 and 99-106 of SEQ ID NO: 26 and/or the VL domain CDR1, CDR2 and CDR3 amino acid sequences respectively comprise residues 27-38, 56-58 and 95-103 of SEQ ID NO: 28. In one non-limiting example, the amino acid sequence of the antibody-binding fragment comprises residues 25-269 of SEQ ID NO: 16.

In other examples wherein the tumor antigen is GPC3, the amino acid sequence of the antigen-binding fragment comprises the CDR1, CDR2 and CDR3 sequences of SEQ ID NO: 30 (HN3 single-domain antibody sequence). The CDR sequences can be determined using any well-known numbering schemes, such as IMGT, Kabat or Chothia. In particular examples, the CDR1, CDR2 and CDR3 amino acid sequences respectively comprise residues 31-35, 50-65 and 96-105 of SEQ ID NO: 30. In other particular examples, the CDR1, CDR2 and CDR3 amino acid sequences respectively comprise residues 26-33, 51-57 and 96-105 of SEQ ID NO: 30. In one non-limiting example, the amino acid sequence of the antibody-binding fragment comprises residues 25-140 of SEQ ID NO: 18.

In yet other examples, where the tumor antigen is GPC3, the amino acid sequence of the antibody-binding fragment comprises the CDR sequences of a GPC3-specific monoclonal antibody disclosed in WO 2013/181543 or WO 2012/145469, which are incorporated herein by reference in their entirety.

In some examples wherein the tumor antigen is GPC2, the amino acid sequence of the antigen-binding fragment comprises the CDR1, CDR2 and CDR3 sequences of SEQ ID NO: 32 (LH7 single-domain antibody sequence). The CDR sequences can be determined using any well-known numbering schemes, such as IMGT, Kabat or Chothia. In particular examples, the CDR1, CDR2 and CDR3 amino acid sequences respectively comprise residues 26-33, 51-57 and 96-109 of SEQ ID NO: 32. In other particular examples, the CDR1, CDR2 and CDR3 amino acid sequences respectively comprise residues 31-35, 50-65 and 96-109 of SEQ ID NO: 32. In one non-limiting example, the amino acid sequence of the antibody-binding fragment comprises residues 25-144 of SEQ ID NO: 20.

In other examples wherein the tumor antigen is GPC2, the amino acid sequence of the antigen-binding fragment comprises the CDR1, CDR2 and CDR3 sequences of SEQ ID NO: 34 (LH4 single-domain antibody sequence). The CDR sequences can be determined using any well-known numbering schemes, such as IMGT, Kabat or Chothia. In particular examples, the CDR1, CDR2 and CDR3 amino acid sequences respectively comprise residues 31-35, 50-65 and 96-109 of SEQ ID NO: 34. In other particular examples, the CDR1, CDR2 and CDR3 amino acid sequences respectively comprise residues 26-33, 51-57 and 96-109 of SEQ ID NO: 34.

In other examples wherein the tumor antigen is GPC2, the amino acid sequence of the antigen-binding fragment comprises the CDR1, CDR2 and CDR3 sequences of SEQ ID NO: 36 (LH6 single-domain antibody sequence). The CDR sequences can be determined using any well-known numbering schemes, such as IMGT, Kabat or Chothia. In particular examples, the CDR1, CDR2 and CDR3 amino acid sequences respectively comprise residues 31-35, 50-66 and 97-110 of SEQ ID NO: 36. In other particular examples, the CDR1, CDR2 and CDR3 amino acid sequences respectively comprise residues 26-33, 51-58 and 97-110 of SEQ ID NO: 36.

In yet other examples, where the tumor antigen is GPC2, the amino acid sequence of the antibody-binding fragment comprises the CDR sequences of a GPC2-specific monoclonal antibody disclosed in Li et al., *Proc Natl Acad Sci USA* 114(32):E6623-E6631, 2017.

In some examples where the tumor antigen is mesothelin, the amino acid sequence of the antigen-binding fragment comprises the VH domain CDR1, CDR2 and CDR3 sequences of SEQ ID NO: 38 (YP218 VH domain) and the VL domain CDR1, CDR2 and CDR3 sequences of SEQ ID NO: 40 (YP218 VL domain). The CDR sequences can be determined using any well-known numbering schemes, such as IMGT, Kabat or Chothia. In particular examples, the VH domain CDR1, CDR2 and CDR3 amino acid sequences respectively comprise residues 31-36, 51-68 and 100-112 of SEQ ID NO: 38 and/or the VL domain CDR1, CDR2 and CDR3 amino acid sequences respectively comprise residues 24-34, 50-56 and 89-101 of SEQ ID NO: 40. In other particular examples, the VH domain CDR1, CDR2 and CDR3 amino acid sequences respectively comprise residues 27-34, 52-59 and 98-112 of SEQ ID NO: 38 and/or the VL domain CDR1, CDR2 and CDR3 amino acid sequences respectively comprise residues 27-32, 50-52 and 89-101 of SEQ ID NO: 40.

In other examples wherein the tumor antigen is mesothelin, the amino acid sequence of the antigen-binding fragment comprises the CDR1, CDR2 and CDR3 sequences of SEQ ID NO: 42 (SD1 single-domain antibody sequence). The CDR sequences can be determined using any well-known numbering schemes, such as IMGT, Kabat or Chothia. In particular examples, the CDR1, CDR2 and CDR3 amino acid sequences respectively comprise residues 31-35, 51-66 and 99-102 of SEQ ID NO: 42. In other particular examples, the CDR1, CDR2 and CDR3 amino acid sequences respectively comprise residues 26-35, 51-58 and 97-103 of SEQ ID NO: 42.

In yet other examples, where the tumor antigen is mesothelin, the amino acid sequence of the antibody-binding fragment comprises the CDR sequences of a mesothelin-specific monoclonal antibody disclosed in WO 2014/031476, WO 2014/052064, U.S. Pat. No. 8,460,660, 6,809,184 or 7,081,518, each of which are incorporated herein by reference in their entirety.

In some embodiments, the isolated host cell is a T lymphocyte. In some examples, the T lymphocyte is an autologous T lymphocyte. In other examples, the T lymphocyte is an allogeneic T lymphocyte.

Also provided herein is a composition that includes an isolated (CAR-expressing) host cell disclosed herein and a pharmaceutically acceptable carrier.

Further provided is a method of treating a GPC3-positive cancer in a subject. In some embodiments, the method includes administering to the subject a therapeutically effective amount of an isolated host cell comprising a nucleic acid molecule encoding a GPC3-targeted CAR as disclosed herein, or administering a therapeutically effective amount of an isolated host cell co-expressing a GPC3-targeted CAR and a huEGFRt, as disclosed herein. In some examples, the GPC3-positive cancer is a hepatocellular carcinoma, a melanoma, an ovarian clear-cell carcinoma, a yolk sac tumor, a neuroblastoma, a hepatoblastoma or a Wilms' tumor.

Also provided is a method of treating a GPC2-positive cancer in a subject. In some embodiments, the method includes administering to the subject a therapeutically effective amount of an isolated host cell comprising a nucleic acid molecule encoding a GPC2-targeted CAR as disclosed herein, or administering a therapeutically effective amount of an isolated host cell co-expressing a GPC2-targeted CAR and a huEGFRt, as disclosed herein. In some examples, the GPC2-positive cancer is a neuroblastoma, an acute lymphoblastic leukemia, an embryonal rhabdomyosarcoma, an alveolar rhabdomyosarcoma, a Ewing's sarcoma, a desmoplastic small round cell tumor or an osteosarcoma.

Further provided is a method of treating a mesothelin-positive cancer in a subject. In some embodiments, the method includes administering to the subject a therapeutically effective amount of an isolated host cell comprising a nucleic acid molecule encoding a mesothelin-targeted CAR as disclosed herein, or administering a therapeutically effective amount of an isolated host cell co-expressing a mesothelin-targeted CAR and a huEGFRt, as disclosed herein. In some examples, the mesothelin-positive cancer is a mesothelioma, prostate cancer, lung cancer, stomach cancer, squamous cell carcinoma, pancreatic cancer, cholangiocarcinoma, triple negative breast cancer or ovarian cancer.

In some embodiments of the methods of treatment, the isolated host cells are T lymphocytes. In some examples, the T lymphocytes are autologous T lymphocytes. In other examples, the T lymphocytes are allogeneic T lymphocytes.

In one embodiment herein, provided is a nucleic acid molecule encoding a CAR that comprises in the 5' to 3' direction a nucleic acid encoding a first GMCSFRss; a nucleic acid encoding an antigen-specific antibody or antigen-binding fragment thereof; a nucleic acid encoding a CD8α hinge region; a nucleic acid encoding a CD8α transmembrane domain; a nucleic acid encoding a 4-1BB co-stimulatory domain; a nucleic acid encoding a CD3ζ signaling domain; a nucleic acid encoding a self-cleaving 2A peptide; a nucleic acid encoding a second GMCSFRss; and a nucleic acid encoding a huEGFRt. In some examples, the nucleic acid encoding the antibody-binding fragment comprises the sequence of nucleotides 73-807 of SEQ ID NO: 15, nucleotides 73-420 of SEQ ID NO: 17 or nucleotides 73-432 of SEQ ID NO: 19. In particular examples, the nucleic acid molecule is at least 80%, at least 85%, at least 90%, at least 95%, at least 96%, at least 97%, at least 98% or at least 99% identical to SEQ ID NO: 15, SEQ ID NO: 17 or SEQ ID NO: 19. In specific non-limiting examples, the nucleic acid molecule comprises the nucleotide sequence of SEQ ID NO: 15, SEQ ID NO: 17 or SEQ ID NO: 19.

In one embodiment herein, provided is an isolated host cell co-expressing a CAR and a huEGFRt, wherein the CAR comprises an antigen-specific antibody or antigen-binding fragment thereof, a CD8α hinge region, a CD8α transmembrane domain, a 4-1BB co-stimulatory domain and a CD3ζ signaling domain; and the huEGFRt comprises a Domain III, a Domain IV and a transmembrane domain from human EGFR, but lacks an EGF-binding domain and a cytoplasmic domain. In some examples, the amino acid sequence of the antigen-binding fragment comprises residues 25-269 of SEQ ID NO: 16, residues 25-140 of SEQ ID NO: 18 or residues 25-144 of SEQ ID NO: 20. In particular examples, the amino acid sequence of the CAR is at least 80%, at least 85%, at least 90%, at least 95%, at least 96%, at least 97%, at least 98% or at least 99% identical to residues 25-491 of SEQ ID NO: 16, residues 25-362 of SEQ ID NO: 18 or residues 25-366 of SEQ ID NO: 20, and the amino acid sequence of the huEGFRt is at least 80%, at least 85%, at least 90%, at least 95%, at least 96%, at least 97%, at least 98% or at least 99% identical to SEQ ID NO: 14. In other particular examples, the amino acid sequence of the CAR comprises no more than 10, no more than 9, no more than 8, no more than 7, no more than 6, no more than 5, no more than 4, no more than 3, no more than 2 or no more than 1 amino acid substitutions relative to residues 25-491 of SEQ ID NO: 16, residues 25-362 of SEQ ID NO: 18 or residues 25-366 of SEQ ID NO: 20 and the amino acid sequence of the huEGFRt comprises no more than 10, no more than 9, no more than 8, no more than 7, no more than 6, no more than 5, no more than 4, no more than 3, no more than 2 or no more than 1 amino acid substitutions relative to SEQ ID NO: 14. In specific non-limiting examples, the amino acid sequence of the CAR comprises residues 25-491 of SEQ ID NO: 16, residues 25-362 of SEQ ID NO: 18 or residues 25-366 of SEQ ID NO: 20, and the amino acid sequence of the huEGFRt comprises SEQ ID NO: 14.

IV. Antibodies Specific for Tumor Antigens

The CARs disclosed herein can be targeted to tumor cells that express or overexpress a specific antigen by selecting an appropriate tumor antigen-specific monoclonal antibody or antigen-binding fragment thereof. In some embodiments, the antigen binding portion of the CAR is an antigen-binding fragment of a monoclonal antibody. In particular examples, the antigen-binding fragment is a scFv or a single-domain (VH domain) antibody. Although the CARs disclosed herein can be used with any antigen-specific antibody (or antigen-binding fragment thereof), exemplary antibodies include GPC3-specific, GPC2-specific and mesothelin-specific monoclonal antibodies.

A. GPC3-Specific Antibodies

The CAR constructs disclosed herein can be engineered to include any GPC3-specific monoclonal antibody or antigen-binding fragment thereof. Several GPC3-specific monoclonal antibodies are known in the art, including, but not limited to YP6, YP7, YP8, YP9 and YP9.1 disclosed in PCT Publication No. WO 2013/181543, and HN3 disclosed in WO 2012/145469, which are incorporated herein by reference in their entirety. In some embodiments herein, the CAR includes an antigen-binding fragment comprising the CDR sequences of the GPC3-specific monoclonal antibody YP7 (disclosed in WO 2013/181543) or a humanized version thereof. The nucleotide and amino acid sequences of YP7 and humanized YP7 (hYP7) are provided below. Tables 1A-1D indicate the locations of CDR1, CDR2 and CDR3 for both YP7 and hYP7. In other embodiments, the CAR includes a single-domain monoclonal antibody comprising the CDR sequences of the GPC3-specific antibody HN3 (disclosed in WO 2012/145469). The nucleotide and amino acid sequences of HN3 are provided below. Tables 2A-2B indicate the locations of CDR1, CDR2 and CDR3 in HN3.

YP7 VH Nucleotide Sequence
(SEQ ID NO: 21)
GAGGTGCAGCTTGTTGAGACTGGTGGAGGAATGGTGCAGCCTGAAGGGTC

ATTGAAACTCTCATGTGCAGCCTCTGGATTCACCTTCAATAAGAATGCCA

TGAATTGGGTCCGCCAGGCTCCAGGAAAGGGTTTGGAATGGGTTGCTCGC

ATAAGAAATAAAACTAATAATTATGCAACATATTATGCCGATTCAGTGAA

AGCCAGGTTTACCATCTCCAGAGATGATTCACAAAGCATGCTCTATCTGC

AAATGAACAACTTGAAAATTGAGGACACAGCCATGTACTATTGTGTGGCT

GGTAACTCGTTTGCTTACTGGGGCCAAGGGACTCTGGTCACTGTCTCTGC

A

YP7 VH Amino Acid Sequence
(SEQ ID NO: 22)
EVQLVETGGGMVQPEGSLKLSCAASGFTFNKNAMNVVVRQAPGKGLEWVA

RIRNKTNNYATYYADSVKARFTISRDDSQSMLYLQMNNLKIEDTAMYYCV

AGNSFAYWGQGTLVTVSA

YP7 VL Nucleotide Sequence
(SEQ ID NO: 23)
GACATTGTGATGTCACAGTCTCCATCCTCCCTAGTTGTGTCAATTGGAGA

GAAGGTTACTATGACCTGCAAGTCCAGTCAGAGCCTTTTATATAGCAGCA

ATCAAAAGAACTACTTGGCCTGGTACCAACAGAAACCAGGGCAGTCTCCT

AAACTGCTGATTTACTGGGCATCCAGTAGGGAATCTGGGGTCCCTGATCG

CTTCACAGGCAGTGGATCTGGGACAGATTTCACTCTCACCATCAGCAGTG

TGAAGGCTGAAGACCTGGCAGTTTATTACTGTCAGCAATATTATAACTAT

CCGCTCACGTTCGGTGCTGGGACCAAGTTGGAGCTGAAA

YP7 VL Amino Acid Sequence
(SEQ ID NO: 24)
DIVMSQSPSSLVVSIGEKVTMTCKSSQSLLYSSNQKNYLAWYQQKPGQSP

KWYWASSRESGVPDRFTGSGSGTDFTLTISSVKAEDLAVYYCQQYYNYPL

TFGAGTKLELK hYP7 VH Nucleotide Sequence
(SEQ ID NO: 25)
GAGGTGCAGCTTGTTGAGTCTGGTGGAGGATTGGTGCAGCCTGGAGGGTC

ATTGAGACTCTCATGTGCAGCCTCTGGATTCACCTTCAATAAGAATGCCA

TGAATTGGGTCCGCCAGGCTCCAGGAAAGGGTTTGGAATGGGTTGGCCGC

ATAAGAAATAAAACTAATAATTATGCAACATATTATGCCGATTCAGTGAA

AGCCAGGTTTACCATCTCCAGAGATGATTCAAAGAACTCACTCTATCTGC

AAATGAACAGCTTGAAAACCGAGGACACAGCCGTGTACTATTGTGTGGCT

GGTAACTCGTTTGCTTACTGGGGCCAAGGGACTCTGGTCACTGTCTCTGC

A hYP7 VH Amino Acid Sequence
(SEQ ID NO: 26)
EVQLVESGGGLVQPGGSLRLSCAASGFTFNKNAMNWVRQAPGKGLEWVGR

IRNKTNNYATYYADSVKARFTISRDDSKNSLYLQMNSLKTEDTAVYYCVA

GNSFAYWGQGTLVTVSA hYP7 VL Nucleotide Sequence
(SEQ ID NO: 27)
GACATTGTGATGACCCAGTCTCCAGACTCCCTAGCTGTGTCACTGGGAGA

GAGGGCCACTATCAACTGCAAGTCCAGTCAGAGCCTTTTATATAGCAGCA

-continued

ATCAAAAGAACTACTTGGCCTGGTACCAACAGAAACCAGGGCAGCCTCCT

AAACTGCTGATTTACTGGGCATCCAGTAGGGAATCTGGGGTCCCTGATCG

CTTCAGTGGCAGTGGATCTGGGACAGATTTCACTCTCACCATCAGCAGTC

TGCAGGCTGAAGACGTGGCAGTTTATTACTGTCAGCAATATTATAACTAT

CCGCTCACGTTCGGTCAGGGGACCAAGTTGGAGATCAAA hYP7 VL Amino Acid Sequence
(SEQ ID NO: 28)
DIVMTQSPDSLAVSLGERATINCKSSQSLLYSSNQKNYLAWYQQKPGQPP

KLLIYWASSRESGVPDRFSGSGSGTDFTLTISSLQAEDVAVYYCQQYYNY

PLTFGQGTKLEIK

TABLE 1A

Locations of the CDRs in the YP7/hYP7 VH Sequence (according to Kabat)

| CDR | DNA Sequence (SEQ ID NO: 21/ SEQ ID NO: 25) | Protein Sequence (SEQ ID NO: 22/ SEQ ID NO: 26) |
| --- | --- | --- |
| CDR1 | nucleotides 91-105 | amino acids 31-35 |
| CDR2 | nucleotides 148-204 | amino acids 50-68 |
| CDR3 | nucleotides 301-318 | amino acids 101-106 |

TABLE 1B

Locations of the CDRs in the YP7/hYP7 VH Sequence (according to IMGT)

| CDR | DNA Sequence (SEQ ID NO: 21/ SEQ ID NO: 25) | Protein Sequence (SEQ ID NO: 22/ SEQ ID NO: 26) |
| --- | --- | --- |
| CDR1 | nucleotides 76-99 | amino acids 26-33 |
| CDR2 | nucleotides 151-180 | amino acids 51-60 |
| CDR3 | nucleotides 295-318 | amino acids 99-106 |

TABLE 1C

Locations of the CDRs in the YP7/hYP7 VL Sequence (according to Kabat)

| CDR | DNA Sequence (SEQ ID NO: 23/ SEQ ID NO: 27) | Protein Sequence (SEQ ID NO: 24/ SEQ ID NO: 28) |
| --- | --- | --- |
| CDR1 | nucleotides 70-120 | amino acids 24-40 |
| CDR2 | nucleotides 166-186 | amino acids 56-62 |
| CDR3 | nucleotides 283-309 | amino acids 95-103 |

TABLE 1D

Locations of the CDRs in the YP7/hYP7 VL Sequence (according to IMGT)

| CDR | DNA Sequence (SEQ ID NO: 23/ SEQ ID NO: 27) | Protein Sequence (SEQ ID NO: 24/ SEQ ID NO: 28) |
| --- | --- | --- |
| CDR1 | nucleotides 79-114 | amino acids 27-38 |
| CDR2 | nucleotides 166-174 | amino acids 56-58 |
| CDR3 | nucleotides 283-309 | amino acids 95-103 |

HN3 DNA Sequence
(SEQ ID NO: 29)
CAGGTGCAGCTGGTGCAGTCTGGGGGAGGCTTGGTACAGCCTGGAGGGTC

CCTGAGACTCTCCTGTGCAGCCTCTTATTTCGATTTCGATTCTTATGAAA

TGAGCTGGGTCCGCCAGGCTCCAGGGAAGGGCCTAGAGTGGATTGGGAGT

ATCTATCATAGTGGGAGCACCTACTACAACCCGTCCCTCAAGAGTCGAGT

CACCATCTCCAGAGACAATTCCAAGAACACGCTGTATCTGCAAATGAACA

CCCTGAGAGCCGAGGACACAGCCACGTATTACTGTGCGAGAGTAAATATG

GACCGATTTGACTACTGGGGCCAGGGAACCCTGGTCACCGTCTCCTCAAG

T

HN3 Protein Sequence
(SEQ ID NO: 30)
QVQLVQSGGGLVQPGGSLRLSCAASYFDFDSYEMSWVRQAPGKGLEWIGS

IYHSGSTYYNPSLKSRVTISRDNSKNTLYLQMNTLRAEDTATYYCARVNM

DRFDYWGQGTLVTVSSS

TABLE 2A

Locations of the CDRs in the HN3 Sequence (according to Kabat)

| CDR | DNA Sequence (SEQ ID NO: 29) | Protein Sequence (SEQ ID NO: 30) |
| --- | --- | --- |
| CDR1 | nucleotides 91-105 | amino acids 31-35 |
| CDR2 | nucleotides 148-195 | amino acids 50-65 |
| CDR3 | nucleotides 286-315 | amino acids 96-105 |

TABLE 2B

Locations of the CDRs in the HN3 Sequence (according to IMGT)

| CDR | DNA Sequence (SEQ ID NO: 29) | Protein Sequence (SEQ ID NO: 30) |
| --- | --- | --- |
| CDR1 | nucleotides 76-99 | amino acids 26-33 |
| CDR2 | nucleotides 151-171 | amino acids 51-57 |
| CDR3 | nucleotides 286-315 | amino acids 96-105 |

B. GPC2-Specific Antibodies

The CAR constructs disclosed herein can also be engineered to include any GPC2-specific monoclonal antibody or antigen-binding fragment thereof. In some embodiments herein, the CAR includes an antigen-binding fragment comprising the CDR sequences of the GPC2-specific single-domain monoclonal antibody LH7, LH4, LH6, LH1, LH2 or LH3 (disclosed in Li et al., *Proc Natl Acad Sci USA* 114(32):E6623-E6631, 2017). The nucleotide and amino acid sequences of LH7, LH4 and LH6 are provided below. Tables 3A-5B indicate the locations of CDR1, CDR2 and CDR3 for LH7, LH4 and LH6.

LH7 DNA
(SEQ ID NO: 31)
CAGGTGCAGCTGGTGCAGTCTGGGGGAGGCTTGGTACAGCCTGGAGGGTC

CCTGAGACTCTCCTGTGCAGCCTCTGATTTCTATTTCTATGATTATGAAA

TGAGCTGGGTCCGCCAGGCTCCAGGGAAGGGTCTGGAGTGGATTGGGACT

GTCCCTATAGTGGGAGCACCTACTACAACCCGTCCCTCAAGAGTCGAGT

CACCATCTCCAGAGACAATTCCAAGAACACGCTGTATCTGCAAATGAACA

```
CCCTAAGAGCCGAGGACACAGCCATGTATTACTGTGCGAGAGGTTACAGC

TATGATGACTCCCGATATTTTGACTACTGGGGCCAGGGAACCCTGGTCAC

CGTCTCCTCA
```

LH7 protein (SEQ ID NO: 32)
```
QVQLVQSGGGLVQPGGSLRLSCAASDFYFYDYEMSWVRQAPGKGLEWIGT

VSYSGSTYYNPSLKSRVTISRDNSKNTLYLQMNTLRAEDTAMYYCARGYS

YDDSRYFDYWGQGTLVTVSS
```

TABLE 3A

Locations of the CDRs in the LH7 Sequence (according to Kabat)

| CDR | DNA Sequence (SEQ ID NO: 31) | Protein Sequence (SEQ ID NO: 32) |
|---|---|---|
| CDR1 | 91-105 | 31-35 |
| CDR2 | 148-195 | 50-65 |
| CDR3 | 286-327 | 96-109 |

TABLE 3B

Locations of the CDRs in the LH7 Sequence (according to IMGT)

| CDR | DNA Sequence (SEQ ID NO: 31) | Protein Sequence (SEQ ID NO: 32) |
|---|---|---|
| CDR1 | 76-99 | 26-33 |
| CDR2 | 151-171 | 51-57 |
| CDR3 | 286-327 | 96-109 |

LH4 DNA (SEQ ID NO: 33)
```
CAGGTGCAGCTGGTGCAGTCTGGGGGAGGCTTGGTACAGCCTGGAGGGTC

CCTGAGACTCTCCTGTGCAGCCTCTTCTTTCTATTTCGATGATTATGAAA

TGAGCTGGGTCCGCCAGGCTCCAGGGAAGGCCCTGGAGTGGATTGGGCGT

ATCTATACCAGTGGGAGCACCAACTACAACCCCTCCCTCAAGAGTCGAGT

CACCATCTCCAGAGACAATTCCAAGAACACGCTGTATCTGCAAATGAACA

CCCTGAGAGCCGAGGACACAGCCACGTATTACTGTGCGAGGGGATATTGT

AGTGGTGGTAGCTGCTACTTTGACTACTGGGGCCAGGGAACCCTGGTCAC

CGTCTCCTCA
```
LH4 protein (SEQ ID NO: 34)
```
QVQLVQSGGGLVQPGGSLRLSCAASSFYFDDYEMSWVRQAPGKALEWIGR

IYTSGSTNYNPSLKSRVTISRDNSKNTLYLQMNTLRAEDTATYYCARGYC

SGGSCYFDYWGQGTLVTVSS
```

TABLE 4A

Locations of the CDRs in the LH4 Sequence (according to Kabat)

| CDR | DNA Sequence (SEQ ID NO: 33) | Protein Sequence (SEQ ID NO: 34) |
|---|---|---|
| CDR1 | 91-105 | 31-35 |
| CDR2 | 148-195 | 50-65 |
| CDR3 | 286-327 | 96-109 |

TABLE 4B

Locations of the CDRs in the LH4 Sequence (according to IMGT)

| CDR | DNA Sequence (SEQ ID NO: 33) | Protein Sequence (SEQ ID NO: 34) |
|---|---|---|
| CDR1 | 76-99 | 26-33 |
| CDR2 | 151-171 | 51-57 |
| CDR3 | 286-327 | 96-109 |

LH6 DNA (SEQ ID NO: 35)
```
CAGGTGCAGCTGGTGCAGTCTGGGGGAGGCTTGGTACAGCCTGGAGGGTC

CCTGAGACTCTCCTGTGCAGCCTCTGATTTCTATTTCGATGATTATGAAA

TGAGCTGGGTCCGCCAGGCTCCAGGGAAGGGGCTGGAGTGGGTCTCAACT

ATTAGTGGTAGTGGTGGTGGCACATACTACGCAGACTCAGTGAAGGGCCG

ATTCACCATCTCCAGAGACAATTCCAAGAACACGCTGTATCTGCAAATGA

ACACCCTGAGAGCCGAGGACACAGCCACATATTACTGTGCGAGAGGTTAC

AGTTATGACGACTCCCGATATTTTGACTACTGGGGCCAGGGAACCCTGGT

CACCGTCTCCTCA
```
LH6 protein (SEQ ID NO: 36)
```
QVQLVQSGGGLVQPGGSLRLSCAASDFYFDDYEMSWVRQAPGKGLEWVST

ISGSGGGTYYADSVKGRFTISRDNSKNTLYLQMNTLRAEDTATYYCARGY

SYDDSRYFDYWGQGTLVTVSS
```

TABLE 5A

Locations of the CDRs in the LH6 Sequence (according to Kabat)

| CDR | DNA Sequence (SEQ ID NO: 35) | Protein Sequence (SEQ ID NO: 36) |
|---|---|---|
| CDR1 | 91-105 | 31-35 |
| CDR2 | 148-198 | 50-66 |
| CDR3 | 289-330 | 97-110 |

TABLE 5B

Locations of the CDRs in the LH6 Sequence (according to IMGT)

| CDR | DNA Sequence (SEQ ID NO: 35) | Protein Sequence (SEQ ID NO: 36) |
|---|---|---|
| CDR1 | 76-99 | 26-33 |
| CDR2 | 151-174 | 51-58 |
| CDR3 | 289-330 | 97-110 |

C. Mesothelin-Specific Antibodies

The CAR constructs disclosed herein can also be engineered to include any mesothelin-specific monoclonal antibody or antigen-binding fragment thereof. Several mesothelin-specific monoclonal antibodies are known in the art, including, but not limited to YP218, YP223, YP3, YP158 and YP187 disclosed in PCT Publication No. WO 2014/031476, SD1 disclosed in PCT Publication No. WO 2014/052064, HN1 disclosed in U.S. Pat. No. 8,460,660, SS disclosed in U.S. Pat. No. 6,809,184, and SS1 disclosed in U.S. Pat. No. 7,081,518, each of which are incorporated herein by reference in their entirety. The nucleotide and amino acid sequences of YP218 and SD1 are provided below. Tables 6A-7B indicate the locations of the YP218 and SD1 CDRs.

YP218 VH Nucleotide Sequence
(SEQ ID NO: 37)
CAGCAGCAGCTGGAGGAGTCCGGGGGAGGCCTGGTCAAGCCTGAGGGATC

CCTGACACTCACCTGCAAAGCCTCTGGATTCGACCTCGGTTTCTACTTTT

ACGCCTGTTGGGTCCGCCAGGCTCCAGGGAAGGGCCTGGAGTGGATCGCA

TGCATTTATACTGCTGGTAGTGGTAGCACGTACTACGCGAGCTGGGCGAA

AGGCCGATTCACCATCTCCAAAGCCTCGTCGACCACGGTGACTCTGCAAA

TGACCAGTCTGGCAGCCGCGGACACGGCCACCTATTTCTGTGCGAGATCT

ACTGCTAATACTAGAAGTACTTATTATCTTAACTTGTGGGGCCCAGGCAC

CCTGGTCACCGTCTCCTCA

YP218 VH Amino Acid Sequence
(SEQ ID NO: 38)
QQQLEESGGGLVKPEGSLTLTCKASGFDLGFYFYACWVRQAPGKGLEWIA

CIYTAGSGSTYYASWAKGRFTISKASSTTVTLQMTSLAAADTATYFCARS

TANTRSTYYLNLWGPGTLVTVSS

YP218 VL Nucleotide Sequence
(SEQ ID NO: 39)
GACGTCGTGATGACCCAGACTCCAGCCTCCGTGTCTGAACCTGTGGGAGG

CACAGTCACCATCAAGTGCCAGGCCAGTCAGAGGATTAGTAGTTACTTAT

CCTGGTATCAGCAGAAACCAGGGCAGCGTCCCAAGCTCCTGATCTTTGGT

GCATCCACTCTGGCATCTGGGGTCCCCTCGCGGTTCAAAGGCAGTGGATC

TGGGACAGAATACACTCTCACCATCAGCGACCTGGAGTGTGCCGATGCTG

CCACTTACTACTGTCAGAGTTATGCTTATTTTGATAGTAATAATTGGCAT

GCTTTCGGCGGAGGGACCGAGGTGGTGGTC

YP218 VL Amino Acid Sequence
(SEQ ID NO: 40)
DVVMTQTPASVSEPVGGTVTIKCQASQRISSYLSWYQQKPGQRPKLLIFG

ASTLASGVPSRFKGSGSGTEYTLTISDLECADAATYYCQSYAYFDSNNVV

HAFGGGTEVVV

TABLE 6A

Locations of the CDRs in the YP218
VH Sequence (according to Kabat)

| CDR | DNA Sequence (SEQ ID NO: 37) | Protein Sequence (SEQ ID NO: 38) |
|---|---|---|
| CDR1 | nucleotides 91-108 | amino acids 31-36 |
| CDR2 | nucleotides 101-204 | amino acids 51-68 |
| CDR3 | nucleotides 298-336 | amino acids 100-112 |

TABLE 6B

Locations of the CDRs in the YP218
VH Sequence (according to IMGT)

| CDR | DNA Sequence (SEQ ID NO: 37) | Protein Sequence (SEQ ID NO: 38) |
|---|---|---|
| CDR1 | nucleotides 79-102 | amino acids 27-34 |
| CDR2 | nucleotides 154-177 | amino acids 52-59 |
| CDR3 | nucleotides 292-336 | amino acids 98-112 |

TABLE 6C

Locations of the CDRs in the YP218
VL Sequence (according to Kabat)

| CDR | DNA Sequence (SEQ ID NO: 39) | Protein Sequence (SEQ ID NO: 40) |
|---|---|---|
| CDR1 | nucleotides 70-102 | amino acids 24-34 |
| CDR2 | nucleotides 148-168 | amino acids 50-56 |
| CDR3 | nucleotides 265-303 | amino acids 89-101 |

TABLE 6D

Locations of the CDRs in the YP218
VL Sequence (according to IMGT)

| CDR | DNA Sequence (SEQ ID NO: 39) | Protein Sequence (SEQ ID NO: 40) |
|---|---|---|
| CDR1 | nucleotides 79-96 | amino acids 27-32 |
| CDR2 | nucleotides 148-156 | amino acids 50-52 |
| CDR3 | nucleotides 265-303 | amino acids 89-101 |

SD1 nucleotide sequence (SEQ ID NO: 41):
CAGGTGCAGCTGGTGCAGTCTGGGGGAGGCTTGGTACAGCCTGGAGGGTC

CCTGAGACTCTCCTGTGCAGCCTCTGATTTCGATTTCGCTGCTTATGAAA

TGAGCTGGGTCCGCCAGGCTCCAGGACAAGGCCTTGAGTGGGTGGCAATT

ATATCACATGATGGAATCGATAAATACTACACAGACTCCGTGAAGGGCCG

ATTCACCATCTCCAGAGACAATTCCAAGAACACGCTGTATCTGCAAATGA

ACACCCTGAGAGCCGAGGACACAGCCACGTATTACTGTTTAAGGCTTGGT

GCTGTAGGCCAGGGAACCCTGGTCACCGTCTCCTCAAGT

SD1 amino acid sequence (SEQ ID NO: 42):
QVQLVQSGGGLVQPGGSLRLSCAASDFDFAAYEMSWVRQAPGQGLEWVAI

ISHDGIDKYYTDSVKGRFTISRDNSKNTLYLQMNTLRAEDTATYYCLRLG

AVGQGTLVTVSSS

TABLE 7A

Locations of the CDRs in the SD1 Sequence (according to Kabat)

| CDR | DNA Sequence (SEQ ID NO: 41) | Protein Sequence (SEQ ID NO: 42) |
|---|---|---|
| CDR1 | 91-105 | 31-35 |
| CDR2 | 151-198 | 51-66 |
| CDR3 | 295-306 | 99-102 |

TABLE 7B

Locations of the CDRs in the SD1 Sequence (according to IMGT)

| CDR | DNA Sequence (SEQ ID NO: 41) | Protein Sequence (SEQ ID NO: 42) |
|---|---|---|
| CDR1 | 78-105 | 26-35 |
| CDR2 | 151-174 | 51-58 |
| CDR3 | 289-309 | 97-103 |

V. Chimeric Antigen Receptors (CARs)

Disclosed herein are CARs (also known as chimeric T cell receptors, artificial T cell receptors or chimeric immunoreceptors) and T cells engineered to express CARs. Generally, CARs include a binding moiety, an extracellular hinge/spacer element, a transmembrane region and an intracellular domain that performs signaling functions (Cartellieri et al., J Biomed Biotechnol 2010:956304, 2010; Dai et al., J Natl Cancer Inst 108(7):djv439, 2016). In many instances, the binding moiety is an antigen binding fragment of a monoclonal antibody, such as a scFv or single-domain antibody. The spacer/hinge region typically includes sequences from IgG subclasses, such as IgG1, IgG4, IgD and CD8 domains. The transmembrane domain can be derived from a variety of different T cell proteins, such as CD3ζ, CD4, CD8 or CD28.

While an entire intracellular T cell signaling domain can be employed in a CAR, in many cases it is not necessary to use the entire chain. To the extent that a truncated portion of the intracellular T cell signaling domain is used, such truncated portion may be used in place of the intact chain as long as it transduces the relevant T cell effector function signal. Examples of intracellular T cell signaling domains for use in the CAR include the cytoplasmic sequences of the T cell receptor (TCR) and co-stimulatory molecules that act in concert to initiate signal transduction following antigen receptor engagement, as well as any derivative or variant of these sequences and any synthetic sequence that has the same functional capability. Several different intracellular domains have been used to generate CARs. For example, the intracellular domain can consist of a signaling chain having an ITAM, such as CD3ζ or FcεRIγ. In some instances, the intracellular domain further includes the intracellular portion of at least one additional co-stimulatory domain. The co-stimulatory domain refers to a portion of the CAR comprising the intracellular domain of a costimulatory molecule. A costimulatory molecule is a cell surface molecule other than an antigen receptor or their ligands that is required for an efficient response of lymphocytes to an antigen. Co-stimulatory molecules include, for example, CD28, 4-1BB (CD137, TNFRSF9), OX-40 (CD134), ICOS, CD27 and/or DAP10.

The CAR can also include a signal peptide sequence, e.g., N-terminal to the antigen binding domain. The signal peptide sequence can be any suitable signal peptide sequence, such as a signal sequence from granulocyte-macrophage colony-stimulating factor receptor (GMCSFR), immunoglobulin light chain kappa, or IL-2. While the signal peptide sequence may facilitate expression of the CAR on the surface of the cell, the presence of the signal peptide sequence in an expressed CAR is not necessary in order for the CAR to function. Upon expression of the CAR on the cell surface, the signal peptide sequence may be cleaved off of the CAR. Accordingly, in some embodiments, the CAR lacks a signal peptide sequence.

The CARs disclosed herein are expressed from a construct (such as from a lentivirus vector) that also expresses a truncated version of human EGFR (huEGFRt; discussed in more detail in section VI below). The CAR and huEGFRt are separated by a self-cleaving peptide sequence (such as T2A) such that upon expression in a transduced cell, the CAR is cleaved from huEGFRt (see FIG. 1).

In some embodiments disclosed herein, the CAR constructs encode the following amino acid sequences, in the N-terminal to C-terminal direction:

GMCSFRss:
(SEQ ID NO: 2)
MLLLVTSLLLCELPHPAFLLIP

NdeI:
HM

Antigen-binding:
scFv or single-domain antibody sequence

SpeI:
TS

CD8α hinge:
(SEQ ID NO: 4)
TTTPAPRPPTPAPTIASQPLSLRPEACRPAAGGAVHTRGLDFACD

CD8α TM:
(SEQ ID NO: 6)
IYIVVAPLAGTCGVLLLSLVIT 4-1BB:
(SEQ ID NO: 8)
KRGRKKLLYIFKQPFMRPVQTTQEEDGCSCRFPEEEEGGCEL

CD3ζ:
(SEQ ID NO: 10)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

T2A:
(SEQ ID NO: 12)
EGRGSLLTCGDVEENPGP

GMCSFRss:
(SEQ ID NO: 2)
MLLLVTSLLLCELPHPAFLLIP huEGFRt:
(SEQ ID NO: 14)
RKVCNGIGIGEFKDSLSINATNIKHFKNCTSISGDLHILPVAFRGDSFTH

TPPLDPQELDILKTVKEITGFLLIQAWPENRTDLHAFENLEIIRGRTKQH

GQFSLAVVSLNITSLGLRSLKEISDGDVIISGNKNLCYANTINVVKKLFG

TSGQKTKIISNRGENSCKATGQVCHALCSPEGCWGPEPRDCVSCRNVSRG

RECVDKCNLLEGEPREFVENSECIQCHPECLPQAMNITCTGRGPDNCIQC

AHYIDGPHCVKTCPAGVMGENNTLVWKYADAGHVCHLCHPNCTYGCTGPG

LEGCPTNGPKIPSIATGMVGALLLLLVVALGIGLFM

T cells expressing the CARs disclosed herein can be used to target a specific cell type, such as a tumor cell, for example a GPC3-positive, a GPC2-positive or a mesothelin-positive tumor cell. The use of T cells expressing CARs is more universal than standard CTL-based immunotherapy because CTLs expressing CARs are HLA unrestricted and can therefore be used for any patient having a tumor that expresses the target antigen.

Accordingly, provided herein are CARs that include a tumor-specific antibody (or binding fragment thereof), such as a GPC3-specific antibody, a GPC2-specific antibody or a mesothelin-specific antibody. Also provided are isolated nucleic acid molecules and vectors encoding the CARs, and host cells, such as T lymphocytes, expressing the CARs. T cells expressing CARs comprised of a GPC3-specific, a GPC2-specific or a mesothelin-specific monoclonal antibody can be used for the treatment of cancers that express GPC3, GPC2 and mesothelin, respectively.

VI. Truncated Human EGFR (huEGFRt)

The human epidermal growth factor receptor is comprised of four extracellular domains, a transmembrane domain and three intracellular domains. The EGFR domains are found in the following N-terminal to C-terminal order: Domain I Domain II Domain III Domain IV transmembrane (TM) domain juxtamembrane domain tyrosine kinase domain C-terminal tail. Domain I and Domain III are leucine-rich domains that participate in ligand binding. Domain II and Domain IV are cysteine-rich domains and do not make contact with EGFR ligands. Domain II mediates formation of homo- or hetero-dimers with analogous domains from other EGFR family members, and Domain IV can form disulfide bonds with Domain II. The EGFR™ domain makes a single pass through the cell membrane and may play a role in protein dimerization. The intracellular domain includes the juxtamembrane domain, tyrosine kinase domain and C-terminal tail, which mediate EGFR signal transduction (Wee and Wang, *Cancers* 9(52), doi:10.3390/cancers9050052; Ferguson, *Annu Rev Biophys* 37:353-373, 2008; Wang et al., *Blood* 118(5):1255-1263, 2011).

A truncated version of human EGFR, referred to herein as "huEGFRt" includes only Domain III, Domain IV and the TM domain. Thus, huEGFRt lacks Domain I, Domain II, and all three intracellular domains. huEGFRt is not capable of binding EGF and lacks signaling activity. However, this molecule retains the capacity to bind particular EGFR-specific monoclonal antibodies, such as FDA-approved cetuximab (PCT Publication No. WO 2011/056894, which is herein incorporated by reference).

Transduction of T cells with a construct (such as a lentivirus vector) encoding both huEGFRt and a tumor antigen-specific CAR disclosed herein allows for selection of transduced T cells using labelled EGFR monoclonal antibody cetuximab (ERBITUX™). For example, cetuximab can be labeled with biotin and transduced T cells can be selected using anti-biotin magnetic beads, which are commercially available (such as from Miltenyi Biotec). Co-expression of huEGFRt also allows for in vivo tracking of adoptively transferred CAR-expressing T cells. Furthermore, binding of cetuximab to T cells expressing huEGFRt induces cytotoxicity of ADCC effector cells, thereby providing a mechanism to eliminate transduced T cells in vivo (Wang et al., *Blood* 118(5):1255-1263, 2011), such as at the conclusion of therapy.

In some embodiments herein, a nucleic acid molecule encoding huEGFRt is at least 80%, at least 85%, at least 90%, at least 95%, at least 96%, at least 97%, at least 98% or at least 99% identical to SEQ ID NO: 13. In some examples, the nucleic acid molecule encoding huEGFRt comprises or consists of the nucleotide sequence of SEQ ID NO: 13. In some embodiments, the amino acid sequence of huEGFRt is at least 80%, at least 85%, at least 90%, at least 95%, at least 96%, at least 97%, at least 98% or at least 99% identical to SEQ ID NO: 14. In some examples, the amino acid sequence of huEGFRt comprises or consists of SEQ ID NO: 14. In other embodiments, the amino acid sequence of huEGFRt comprises no more than 10, no more than 9, no more than 8, no more than 7, no more than 6, no more than 5, no more than 4, no more than 3, no more than 2 or no more than 1 amino acid substitutions relative to SEQ ID NO: 14. In some examples, the amino acid substitutions are conservative substitutions.

VII. CAR-Expressing Cell Compositions

Compositions are provided that include CAR-expressing cells in combination with one or more pharmaceutically or physiologically acceptable carriers, diluents or excipients. The CAR-expressing cells can be T cells, such as CD3$^+$ T cells, such as CD4$^+$ and/or CD8$^+$ T cells, and/or NK cells. Such compositions may include buffers such as neutral buffered saline, phosphate buffered saline and the like; carbohydrates such as glucose, mannose, sucrose, dextrans, or mannitol; proteins; polypeptides or amino acids such as glycine; antioxidants; chelating agents such as EDTA or glutathione; adjuvants (e.g., aluminum hydroxide); and preservatives. The cells can be autologous to the recipient. However, the cells can also be heterologous (allogeneic).

With regard to the cells, a variety of aqueous carriers can be used, for example, buffered saline and the like, for introducing the cells. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration in these formulations can vary widely, and will be selected primarily based on fluid volumes, viscosities, body weight and the like in accordance with the particular mode of administration selected and the subject's needs.

The precise amount of the composition to be administered can be determined by a physician with consideration of individual differences in age, weight, tumor size, extent of metastasis, and condition of the patient (subject). It can generally be stated that a pharmaceutical composition comprising the CAR-expressing T cells (and/or NK cells) described herein may be administered at a dosage of $10^4$ to $10^9$ cells/kg body weight, such as $10^5$ to $10^6$ cells/kg body weight, including all integer values within those ranges. Exemplary doses are $10^6$ cells/kg to about $10^8$ cells/kg, such as from about $5 \times 10^6$ cells/kg to about $7.5 \times 10^7$ cells/kg, such as at about $2.5 \times 10^7$ cells/kg, or at about $5.0 \times 10^7$ cells/kg.

A composition can be administered once or multiple times, such as 2, 3, 4, 5, 6, 7, 8, 9 or 10 times at these dosages. The composition can be administered by using infusion techniques that are commonly known in immunotherapy (see, e.g., Rosenberg et al., *New Eng. J. of Med.* 319:1676, 1988). The compositions can be administered daily, weekly, bimonthly or monthly. In some non-limiting examples, the composition is formulated for intravenous administration and is administered multiple times. The quantity and frequency of administration will be determined by such factors as the condition of the subject, and the type and severity of the subject's disease, although appropriate dosages may be determined by clinical trials.

In some embodiments, the CAR-encoding nucleic acid molecule is introduced into cells, such T cells or NK cells, and the subject receives an initial administration of cells, and one or more subsequent administrations of the cells, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR-expressing cells are administered to the subject (e.g., human) per week, e.g., 2, 3, or 4 administrations of the CAR-expressing cells of the disclosure are administered per week. In one embodiment, the subject receives more than one administration of the CAR-expressing T cells per week (e.g., 2, 3 or 4 administrations per week) (also referred to as a cycle), followed by a week of no CAR-expressing cell administrations, and then one or more additional administration of the CAR-expressing cells (e.g., more than one administration of the CAR T cells per week) is administered to the subject. In another embodiment, the subject (e.g., human subject) receives more than one cycle of CAR-expressing cells, and the time between each cycle is less than 10, 9, 8, 7, 6, 5, 4, or 3 days. In one embodiment, the CAR-expressing cells are administered every other day for 3 administrations per week. In another embodiment, the CAR-expressing cells are administered for at least two, three, four, five, six, seven, eight or more weeks. The dosage of the above treatments to be administered to a patient will vary with the precise nature of the condition being treated and the recipient of the treatment. The scaling of dosages for human administration can be performed according to art-accepted practices.

In some embodiments, CAR-expressing T cells are able to replicate in vivo resulting in long-term persistence that can lead to sustained tumor control. In various aspects, the T cells administered to the subject, or the progeny of these cells, persist in the subject for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, or for years after administration of the T cell to the subject. In other embodiments, the cells and their progeny are present for less than six months, five month, four months, three months two months, or one month, e.g., three weeks, two weeks, one week, after administration of the CAR-expressing T cells to the subject.

The administration of the subject compositions may be carried out in any convenient manner, including by injection, ingestion, transfusion, implantation or transplantation. The disclosed compositions can be administered to a patient trans-arterially, subcutaneously, intradermally, intratumorally, intranodally, intramedullary, intramuscularly, by intravenous (i.v.) injection, or intraperitoneally. In some embodiments, the compositions are administered to a patient by intradermal or subcutaneous injection. In other embodiments, the compositions of the present invention are administered by i.v. injection. The compositions can also be injected directly into a tumor or lymph node.

In some embodiments, subjects can undergo leukapheresis, wherein leukocytes are collected, enriched, or depleted ex vivo to select and/or isolate the cells of interest, e.g., T cells and or NK cells. These cell isolates may be expanded by methods known in the art and treated such that one or more CAR constructs can be introduced, thereby creating an autologous cell that express the CAR. In some embodiments herein, CAR-expressing cells are generated using lentiviral vectors expressing the CAR and a truncated form of the human EGFR (huEGFRt). Co-expression of huEGFRt allows for selection and purification of CAR-expressing T cells using an antibody that recognizes huEGFRt (e.g. cetuximab, see PCT Publication No. WO 2011/056894, which is herein incorporated by reference), which described above in section VI.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, T cells can be isolated by incubation with anti-CD3/anti-CD28 (e.g., 3×28)-conjugated beads, such as DYNABEADS® M-450 CD3/CD28 T, for a time period sufficient for positive selection of the desired T cells, see U.S. Published Application No. US20140271635 A1. In a non-limiting example the time period is about 30 minutes. In other non-limiting examples, the time period ranges from 30 minutes to 36 hours or longer and all integer values there between. In further non-limiting examples, the time period is at least 1, 2, 3, 4, 5, 6 hours, 10 to 24 hours, 24 hours or longer. Longer incubation times can be used to isolate T cells in any situation where there are few T cells as compared to other cell types, such in isolation from immunocompromised individuals. Further, use of longer incubation times can increase the efficiency of capture of CD8+ T cells. Thus. by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. Multiple rounds of selection can also be used.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. A T cell population can be selected that expresses one or more cytokines. Methods for screening for cell expression are disclosed in PCT Publication No. WO 2013/126712.

For isolation of a desired population of cells by positive or negative selection, the concentration of cells and surface (e.g., particles such as beads) can be varied to ensure maximum contact of cells and beads. In some embodiments, a concentration of 1 billion cells/ml is used. In further embodiments, greater than 100 million cells/ml is used. In other embodiments, a concentration of cells of 10, 15, 20, 25, 30, 35, 40, 45, 50, 65, 70, 75, 80, 85, 90, 95, or 100 million cells/ml is used. Without being bound by theory, using high concentrations can result in increased cell yield, cell activation, and cell expansion. Lower concentrations of cells can also be used. Without being bound by theory, significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells

VIII. Methods of Treatment

Provided herein are methods of treating cancer in a subject by administering to the subject a therapeutically effective amount of a tumor-targeting CAR T cell disclosed herein. Also provided herein is a method of inhibiting tumor growth or metastasis in a subject by administering to the subject a therapeutically effective amount of a tumor-targeting CAR T cell disclosed herein.

Specifically provided is a method of treating a GPC3-positive cancer in a subject. In some embodiments, the method includes administering to the subject a therapeutically effective amount of an isolated host cell that comprises a nucleic acid molecule encoding a GPC3-targeted CAR and a huEGFRt, or administering a therapeutically effective amount of an isolated host cell co-expressing a GPC3-targeted CAR and a huEGFRt. In some embodiments, the GPC3-positive cancer is a HCC, a melanoma, an ovarian clear-cell carcinoma, a YST, a neuroblastoma, a hepatoblastoma or a Wilms' tumor.

Also provided is a method of treating a GPC2-positive cancer in a subject. In some embodiments, the method includes administering to the subject a therapeutically effective amount of an isolated host cell that comprises a nucleic acid molecule encoding a GPC2-targeted CAR and a huEGFRt, or administering a therapeutically effective amount of an isolated host cell co-expressing a GPC2-targeted CAR and a huEGFRt. In some embodiments, the GPC2-positive cancer is a neuroblastoma, an acute lymphoblastic leukemia, an embryonal rhabdomyosarcoma, an alveolar rhabdomyosarcoma, a Ewing's sarcoma, a desmoplastic small round cell tumor or an osteosarcoma.

Further provided is a method of treating a mesothelin-positive cancer in a subject. In some embodiments, the method includes administering to the subject a therapeutically effective amount of an isolated host cell that comprises a nucleic acid molecule encoding a mesothelin-targeted CAR and a huEGFRt, or administering a therapeutically effective amount of an isolated host cell co-expressing a mesothelin-targeted CAR and a huEGFRt. In some embodiments, the mesothelin-positive cancer is a mesothelioma, a prostate cancer, a lung cancer, a stomach cancer, a squamous cell carcinoma, a pancreatic cancer, a cholangiocarcinoma, a triple negative breast cancer or an ovarian cancer.

In some embodiments of the methods disclosed herein, the isolated host cells are T lymphocytes. In some examples, the T lymphocytes are autologous T lymphocytes.

A therapeutically effective amount of a CAR-expressing T cell will depend upon the severity of the disease, the type of disease, and the general state of the patient's health. A therapeutically effective amount of CAR-expressing T cells and compositions thereof is that which provides either subjective relief of a symptom(s) or an objectively identifiable improvement as noted by the clinician or other qualified observer (such as a decrease in tumor volume or metastasis).

Administration of the CAR-expressing T cells and compositions disclosed herein can also be accompanied by administration of other anti-cancer agents or therapeutic treatments (such as surgical resection of a tumor). Any suitable anti-cancer agent can be administered in combination with the compositions disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include *vinca* alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocortical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

The following examples are provided to illustrate certain particular features and/or embodiments. These examples should not be construed to limit the disclosure to the particular features or embodiments described.

EXAMPLES

Example 1: CAR-Expressing Lentivirus Constructs

This example describes the generation of three lentivirus vectors that encode a tumor-targeting chimeric antigen receptor (CAR) and a truncated human EGFR (huEGFRt). The pWPT backbone lentiviral vector (Addgene) was used to generate three CAR constructs that target either GPC3 or GPC2. The vectors also encode huEGFRt, which can be recognized by the FDA-approved anti-EGFR antibody cetuximab, enabling CAR T cell labeling and clearance. FIG. 1 provides a schematic of the lentiviral construct for generating the tumor-targeting CARs. The lentivirus construct includes a CAR coding region and a region encoding huEGFRt, each of which is preceded by a granulocyte-macrophage colony stimulating factor receptor signal sequence (GMCSFRss). The two regions are separated by a self-cleaving T2A sequence such that upon expression of the construct, the CAR is cleaved from huEGFRt. Expression of the construct is driven by a human elongation factor 1α (EF1α) promoter. The CAR includes an antigen-binding region, a CD8α hinge region, a CD8α transmembrane (TM) domain, a 4-1BB co-stimulatory region and a CD3ζ signaling domain. The huEGFRt includes two extracellular domains (Domain III and Domain IV) and a TM domain.

Figure 2B:
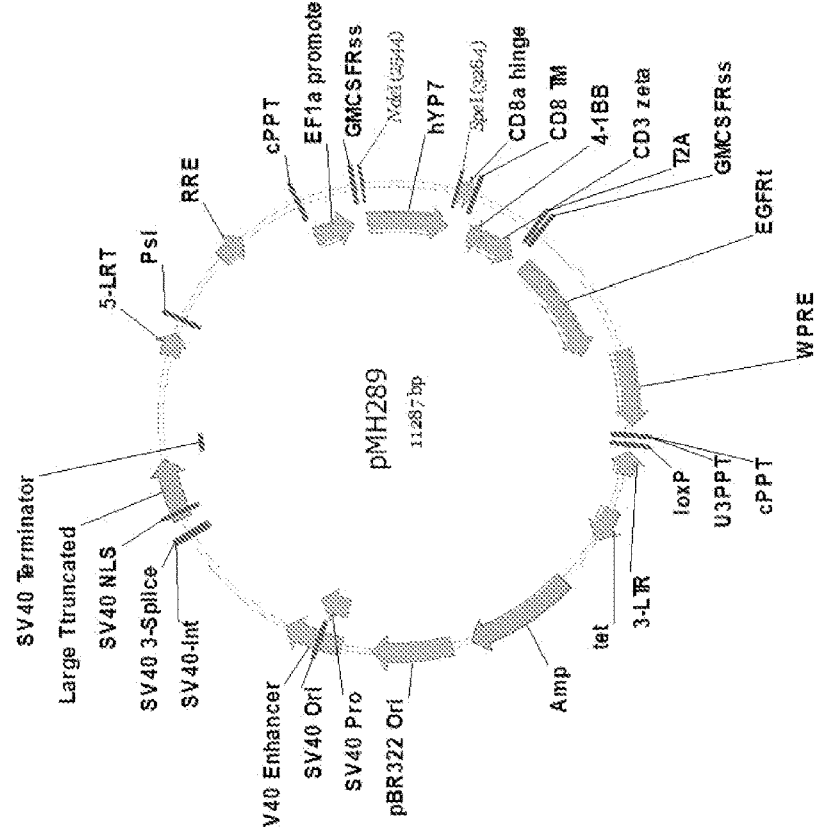
FIGS. 2A-2C are vector maps of constructs pMH288 encoding CAR.HN3 (FIG. 2A), pMH289 encoding CAR.hYP7 (FIG. 2B) and pMH290 encoding CAR.LH7 (FIG. 2C).
Figure 2A:
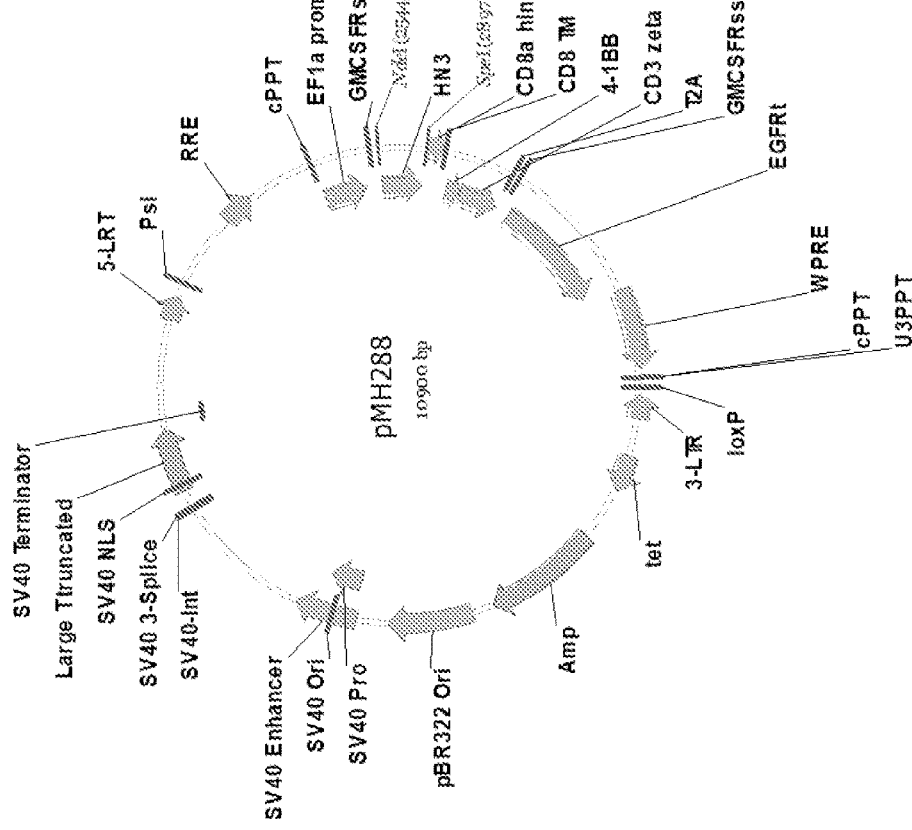
Figure 2C:
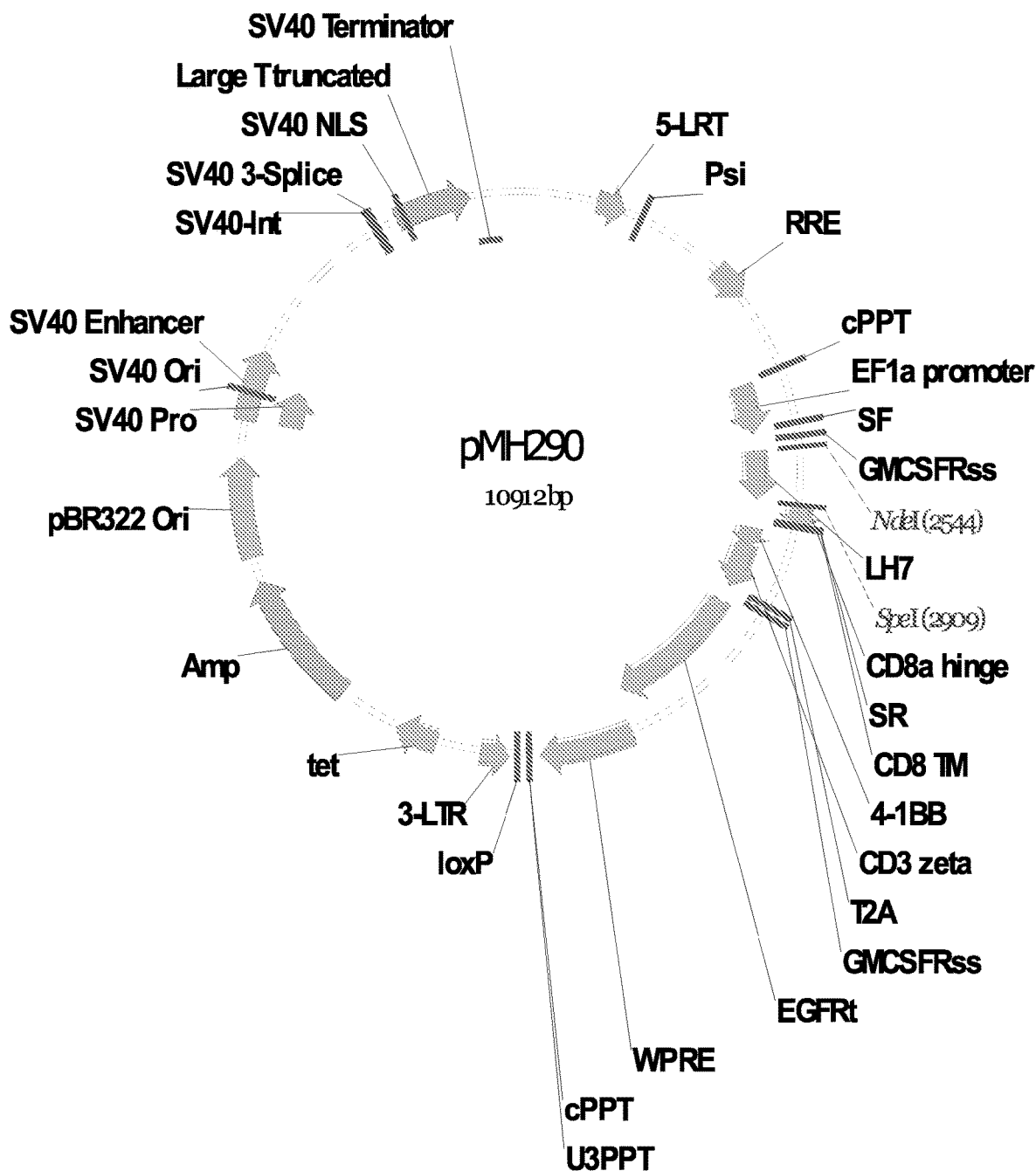

Two of the CAR constructs target GPC3. Lentivirus vector pMH228 encodes GPC3-specific single-domain monoclonal antibody HN3 (disclosed in WO 2012/145469, which is herein incorporated by reference). A vector map of pMH288 is shown in FIG. 2A; the nucleotide and amino acid sequences of CAR.HN3 are set forth herein as SEQ ID NOs: 17 and 18. The second GPC3-specific CAR is expressed from lentivirus vector pMH289, which encodes a humanized scFv of mouse GPC3-specific antibody YP7. Mouse antibody YP7 is disclosed in WO 2013/18154, which is herein incorporated by reference. A vector map of pMH289 is shown in FIG. 2B; the nucleotide and amino acid sequences of CAR.hYP7 are set forth herein as SEQ ID NOs: 15 and 16. The third CAR construct targets GPC2 and is encoded by lentivirus vector pMH290, which encodes GPC2-specific single-domain monoclonal antibody LH7 (disclosed in Li et al., *Proc Natl Acad Sci USA* 114(32): E6623-E6631, 2017). A vector map of pMH290 is shown in FIG. 2C; the nucleotide and amino acid sequences of CAR.LH7 are set forth herein as SEQ ID NOs: 19 and 20. The nucleotide and amino acid sequences of HN3, humanized YP7 (hYP7) and LH7 are provided above in section IV, and are set forth as SEQ ID NOs: 25-32.

Example 2: Materials and Methods

This example describes lentivirus production and titration methods, T cell activation and transduction methods, and functional assays related to the studies described in Example 3.

Lentivirus Production, Concentration and Titration 293T cells were seeded into 10 cm dishes (7.0×10$^6$ cells/dish) 18-24 hours before transfection so that the monolayer cell density reached an optimal 90% confluency at the time of transfection. Approximately 30-60 minutes prior to transfection, cell supernatant was removed and replaced with 5 ml of complete medium (Dulbecco's modified Eagle medium; DMEM) plus serum and antibiotics.

For each dish, a total of 16 µg of DNA (8 µg lentivector plasmid, 2 µg enveloping plasmid MD2G and 6 µg packaging plasmid PAX2) was diluted into 500 µl of serum-free DMEM medium and vortexed gently to mix. Separately, 48 µl CalFectin™ (SignaGen Laboratories; DNA: CalFectin™=1:3) was added to 500 µl of serum free DMEM and mixed gently. The diluted CalFectin™ reagent was then immediately mixed with the diluted DNA solution and vortexed to allow CalFectin™-DNA complexes to form. The mixture was incubated for 10 minutes at room temperature. Next, the CalFectin™-DNA complexes were added dropwise into the medium in each dish and homogenized by gently swirling the plate.

Virus was collected from cell supernatants 48-72 hours post-transfection. Supernatants were centrifuged at 500×g for 5 minutes and then filtered through a 0.45 µm filter. To concentrate the lentivirus, clarified supernatant was transferred to a sterile container and 3 volumes clarified supernatant was combined with 1 volume of Lenti-X Concentrator (Clontech). The mixture was incubated at 4° C. for 30 minutes to overnight. Samples were then centrifuged at 1,500×g for 45 minutes at 4° C., forming an off-white pellet. The supernatant was removed and the pellet was resuspended in 1/10 to 1/100th of the original volume using complete DMEM.

Lentivirus Titration 293T cells were seeded at a density of 1 to 5×10$^5$ cells/well in a 12-well plate with 1 ml growth medium (DMEM supplemented with 10% FBS) per well. One well was used to count cells and another well was used as a non-transduced control (NI). The other wells were transduced with 500 µL, 100 µl, 50 µl, 20 µl or 10 µl of crude (non-concentrated) supernatant in duplicate. The volume of each well was brought up to 500 µl with growth medium. For concentrated virus samples, cells were transduced with 1 µl, 0.1 µl, 0.01 µl, 0.001 µl or 0.0001 µl of vector in 500 µl of fresh growth medium.

After three days, the cells were washed with 1 ml PBS and detached by adding 200 µl of trypsin/EDTA per well and incubation for 1 minute at 37° C. Growth medium (800 µl) was added to each well to resuspend the cells. This step inactivates the trypsin and EDTA. Cells were then transferred into a 5-ml FACS tube, centrifuged for 5 minutes at 500×g and 4° C., and the supernatant was removed. Cells were stained with 1 µg/ml cetuximab in FACS buffer (5% BSA in PBS, 0.01% sodium azide) on ice for 1 hour. Cells were washed with PBS 1×, centrifuged for 5 minutes at 500×g and 4° C. and the pellet was resuspended in secondary antibody with the appropriate fluorochrome. The secondary antibody was also diluted in FACS buffer.

Cells were stained on ice for 1 hour and then washed 1× in PBS, following by centrifugation for 5 minutes at 500×g and 4° C. The pellet was resuspended in 500 µl of 1% formaldehyde in PBS and incubated 5 minutes at room temperature. This step fixes the cells and inactivates the vector particles.

Fixed cells were washed in PBS 1× and centrifuged for 5 minutes at 500×g and 4° C. The pellet was resuspended in 1 ml PBS. Cells were analyzed for CAR expression using a flow cytometer.

T Cell Activation and Transduction Protocol

DYNABEADS™ Human T-Activator CD3/CD28 (Life Technologies) were resuspended in the vial and the desired volume was transferred to a tube. One ml of PBS or growth medium was added and mixed by vortexing for 5 seconds. The vial was centrifuged and the supernatant was discarded. The washed DYNABEADS™ were resuspended in the same volume of culture medium (RPMI1640+10% FBS) as the initial volume of beads taken from the vial.

Frozen peripheral blood mononuclear cells (PBMCs) were thawed and resuspended in growth medium (RPMI1640+10% FBS). Cells were counted using trypan blue reagent. Cells ($1 \times 10^6$) were seeded in 1 ml of culture medium in a 24-well plate. DYNABEADS™ Human T-activator CD3/CD28 were added at a bead-to-cell ratio of 2:1 and 50 U/ml IL-2 was added.

After a 24-hour incubation, PBMCs were spinoculated at 1000 g for 60 minutes with lentivirus (MOI of 5) in the presence of 10 μg/mL protamine sulfate. Cells were then resuspended in the viral supernatant and incubated overnight, maintaining 50 U/ml IL-2.

The following day, cells were centrifuged and resuspended in fresh RPMI1640+10% FBS media with 100 IU/mL of IL-2 added.

For the next 10 days, cultures were examined daily, noting cell size and shape. Cell shrinking and reduced proliferation rate are typically observed in exhausted cell cultures. Cells were counted every other day after thorough re-suspension. When the cell density exceeded $2.0 \times 10^6$ cells/ml or when the medium turned yellow, cultures were split back to a density of $0.5$-$1 \times 10^6$ cells/ml in culture medium containing 100 U/ml IL-2. When cell growth kinetics and volume suggested that cells had rested down from activation, they were used either for functional assays or cryopreserved.

Functional Assay

Luciferase expressing target cells ($2 \times 10^3$) were seeded in 50 μl culture medium in each well of a 96-well plate. CAR T cells (effector cells) were prepared at different Effector (E)/Target (T) ratios. Fifty μl of CAR T cells were added to each well and incubated overnight at 37° C. Each effector:target (E:T) ratio was performed in triplicate. The following day, supernatant was collected for measuring cytokine levels by ELISA and stored in –20° C. Steady Glo luciferase reagent (Promega) was added to each well to lyse tumor cells and the plate was incubated protected from light at room temperature for at least 5 minutes. Luminescence was read on Victor (PerkinElmer). Results are analyzed as percent killing based on luciferase activity in wells with tumor cells alone: [% killing=100–((RLU from well with effector and target cells)/(RLU from wells with target cells)×100)].

Example 3: GPC3-Targeted CARs Induce Cytotoxicity of GPC3-Expressing Cell Lines and Reduce Tumor Volume of GPC3-Positive Tumors in Animal Models This example describes the in vitro and in vivo cytotoxicity of T cells expressing CAR.HN3 and CAR.hYP7.

Figure 3B:
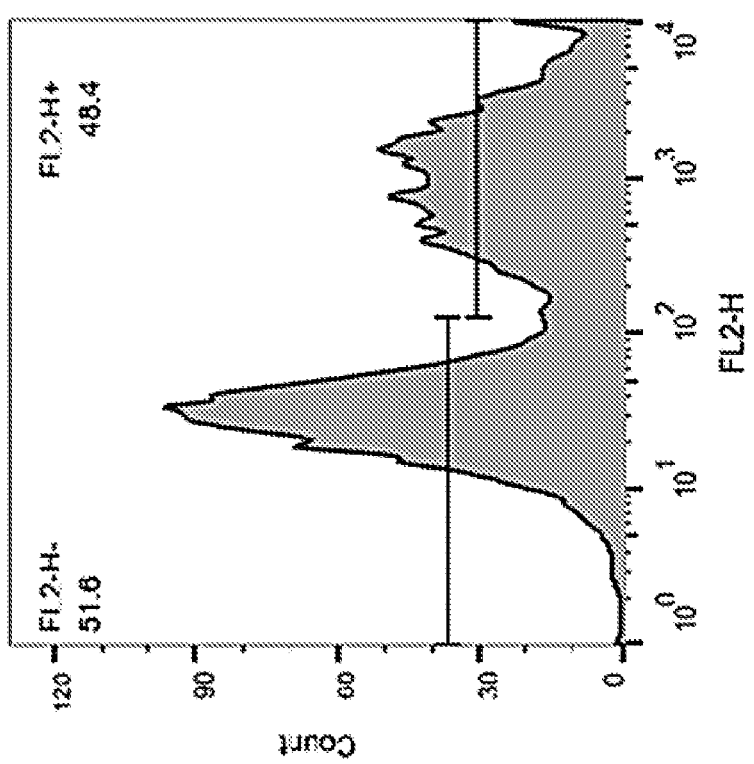
FIGS. 3A-3C are flow cytometry plots showing the transduction efficiency of GPC3-targeted CAR T cells. Transduction efficiency was determined using the anti-huEGFRt antibody cetuximab. Lentivirus vectors encoding CAR.HN3 (FIG. 3A) and CAR.hYP7 (FIG. 3B) transduced 65% and 45.4% of T cells, respectively.
Figure 3A:
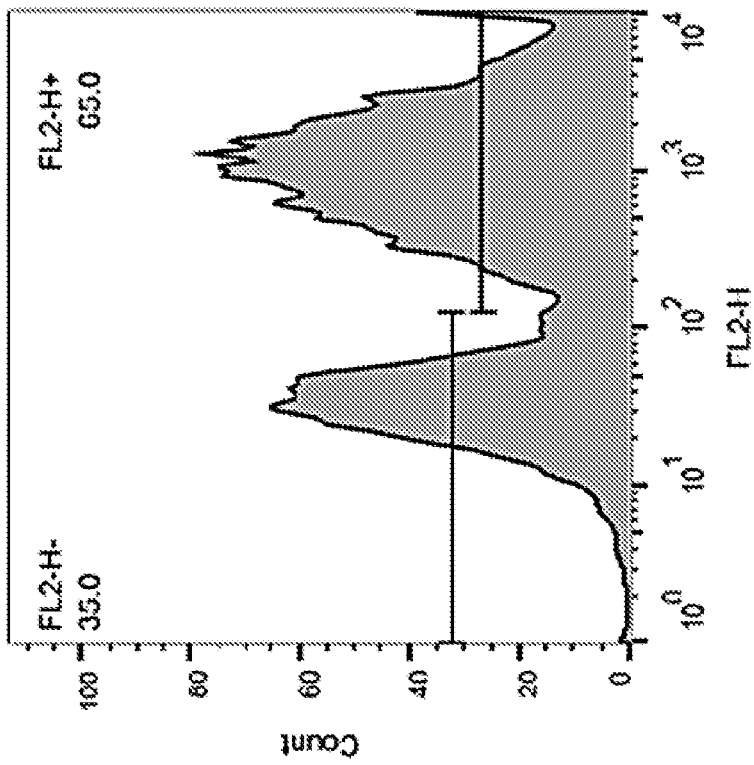
Figure 3C:
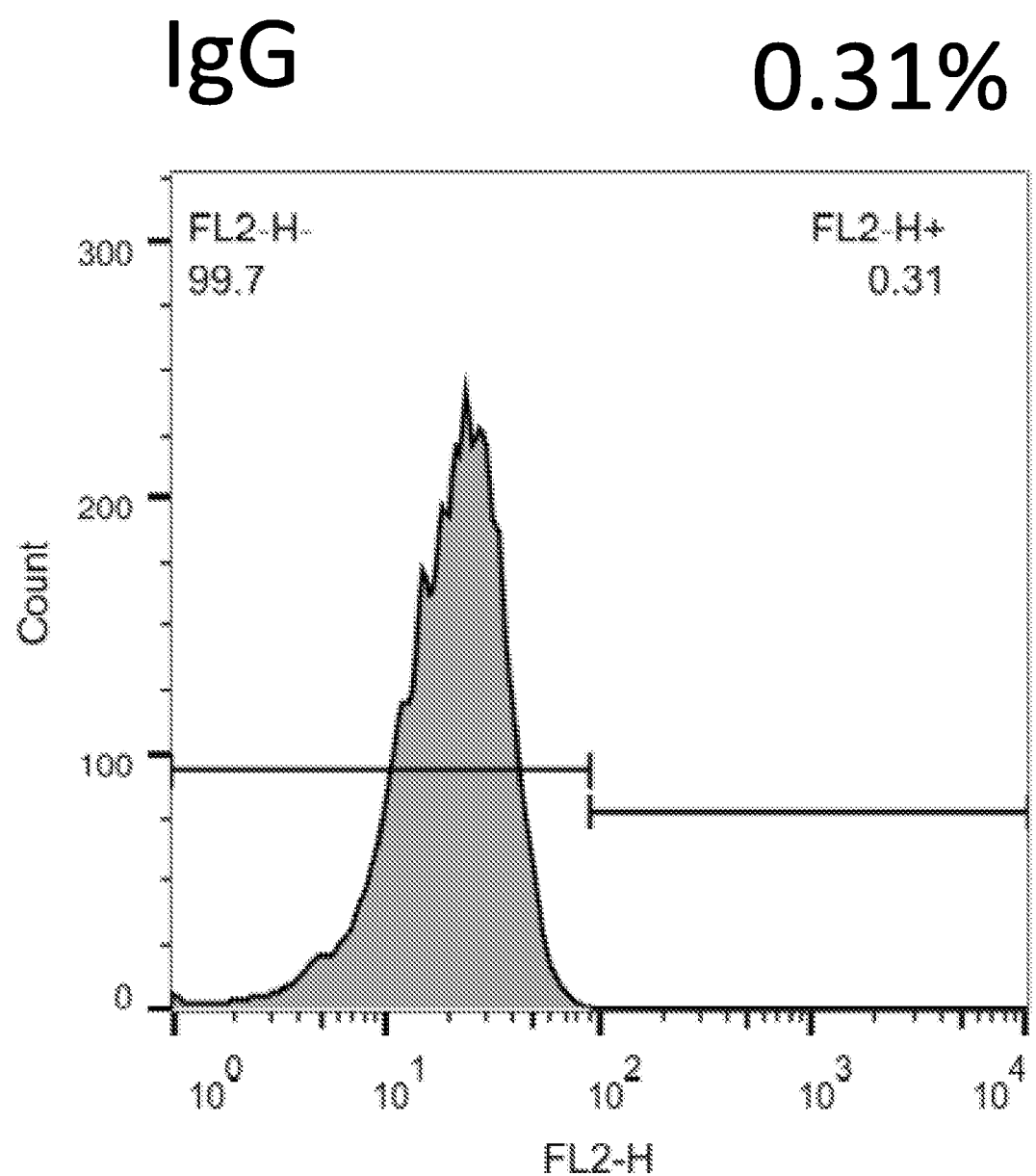

T cell transduction efficiency of the lentiviral vectors pMH288 (expressing CAR.HN3) and pMH289 (expressing CAR.hYP7) was evaluated by flow cytometry using the anti-huEGFRt antibody cetuximab. Lentivirus vectors encoding CAR.HN3 (FIG. 3A) and CAR.hYP7 (FIG. 3B) transduced 65% and 45.4% of T cells, respectively. Human serum IgG was used as a control (FIG. 3C).

Figure 4A:
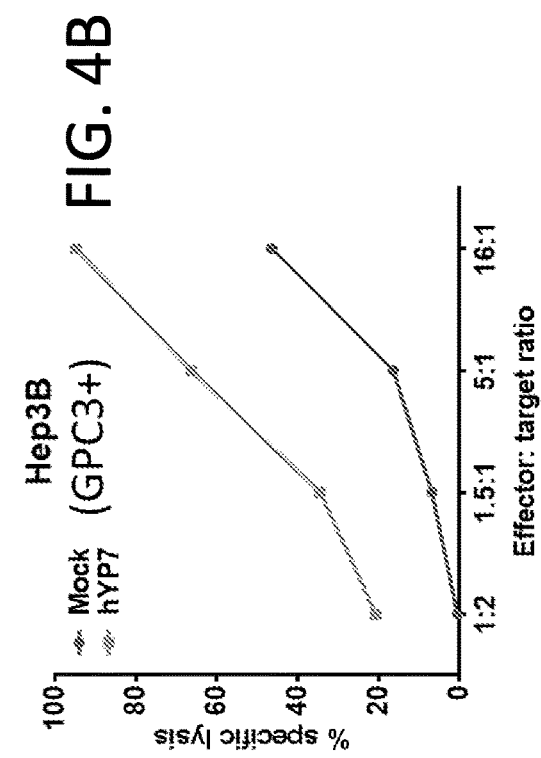
FIGS. 4A-4G are graphs showing cytotoxicity of GPC3-targeting CAR T cells on human cell lines. CAR.hYP7 was tested on GPC3$^+$ G1 cells (FIG. 4A), GPC3$^+$ Hep3B cells (FIG. 4B), GPC3$^+$ HepG2 cells (FIG. 4C), GPC3$^+$ Huh7 cells (FIG. 4D), GPC3$^-$ A431 cells (FIG. 4E), GPC3$^-$ T3M4 cells (FIG. 4F) and GPC3$^-$ IMR32 cells (FIG. 4G) using effector:target ratios of 1:2, 1.5:1, 5:1 and 16:1. CAR.hYP7 was cytotoxic to GPC3-positive cell lines, but not GPC3-negative cell lines.
Figure 4B:
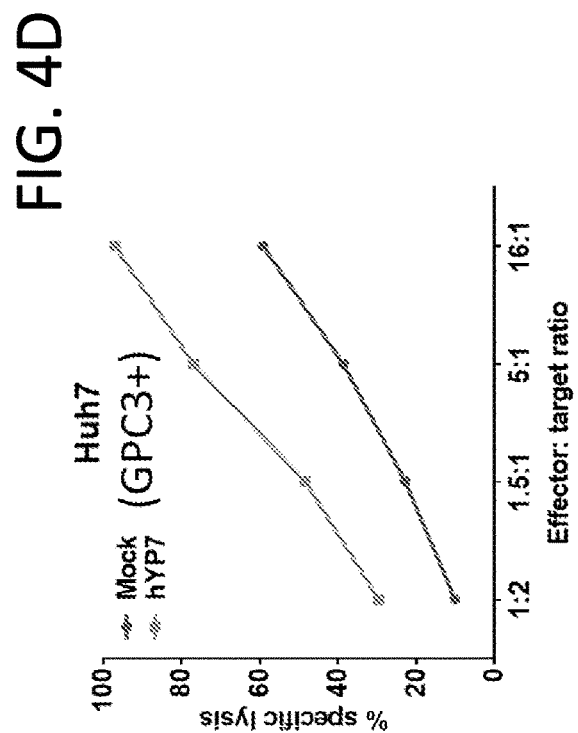
Figure 4C:
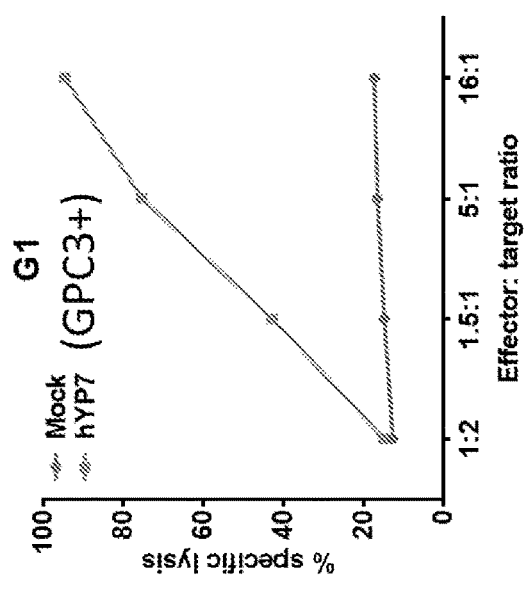
Figure 4D:
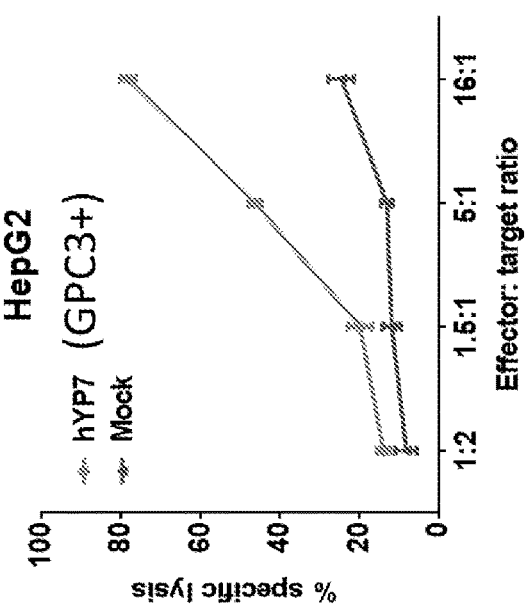
Figure 4E:
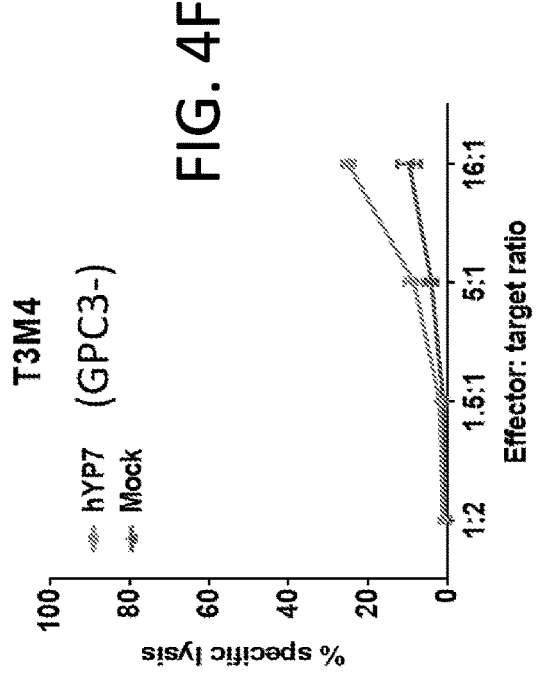
Figure 4F:
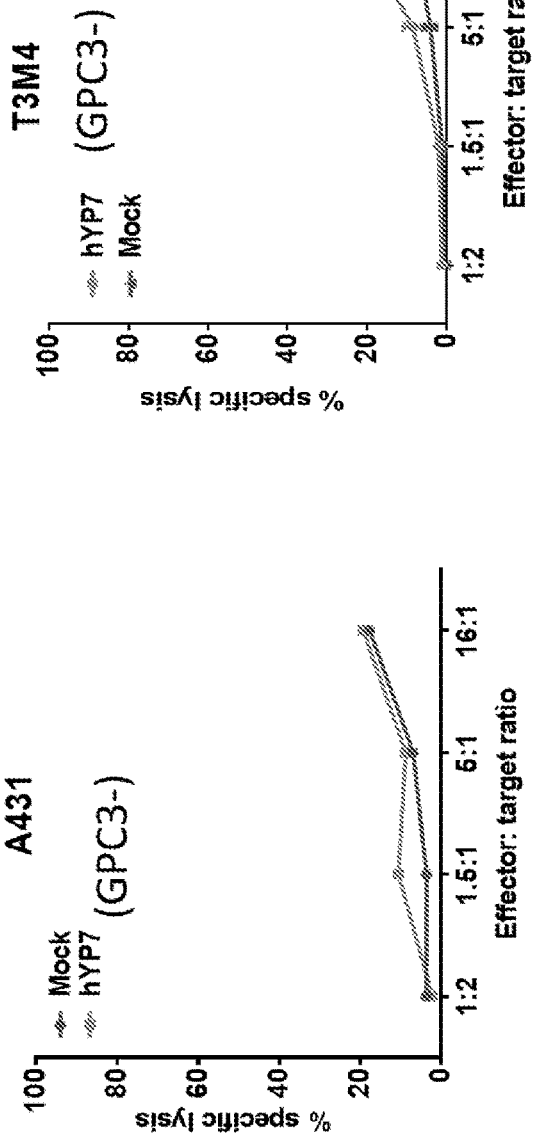
Figure 4G:
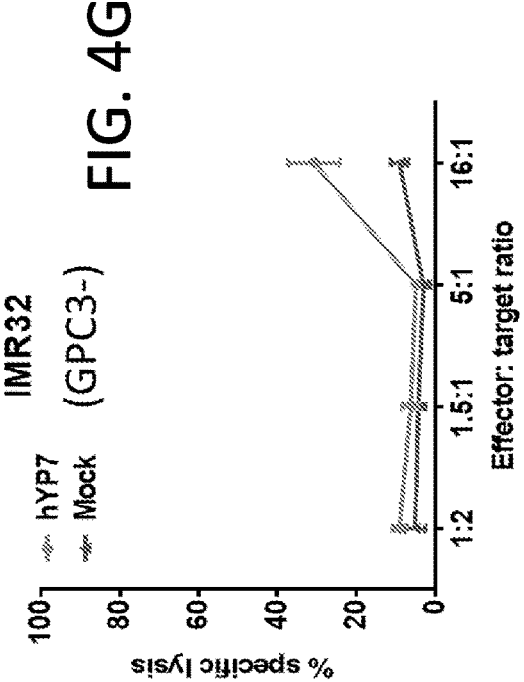

Cytotoxicity of CAR.hYP7 T cells on several human cell lines was tested, including GPC3$^+$ G1 cells, Hep3B cells HepG2 cells and Huh7 cells, and GPC3$^-$ A431 cells, T3M4 cells and IMR32 cells. For each cell line, effector:target ratios of 1:2, 1.5:1, 5:1 and 16:1 were used. CAR.hYP7 T cells were cytotoxic to all GPC3-positive cell lines (FIGS. 4A-4D), but not GPC3-negative cell lines (FIGS. 4E-4G).

Figure 5:
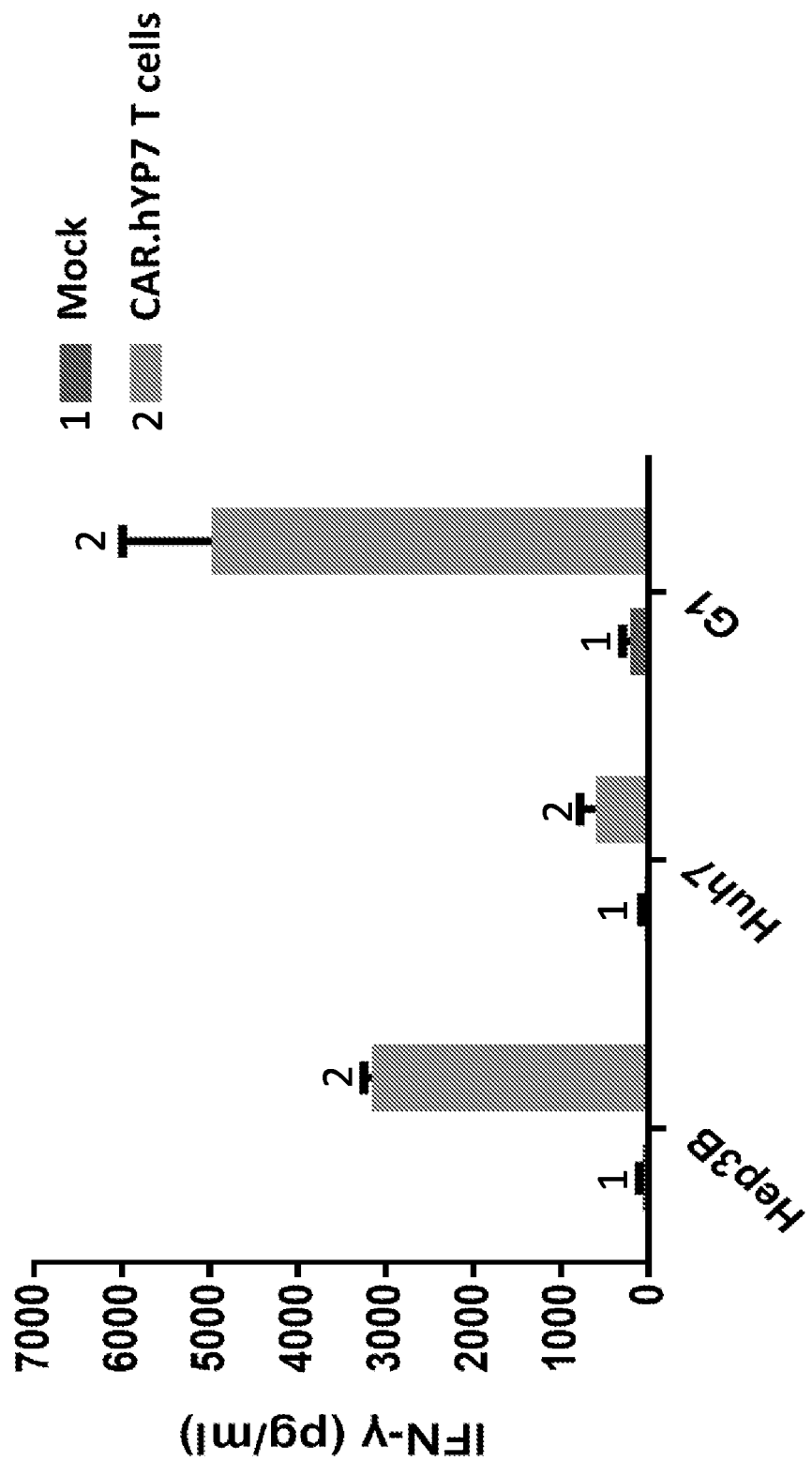
FIG. 5 is a graph showing CAR.hYP7 T cells induce interferon (IFN)-γ secretion of target GPC-positive Hep3B, Huh7 and G1 tumor cells.

Another study was performed to determine whether treatment with CAR.hYP7 T cells induces IFN-γ production of GPC3-positive cells in culture. Hep3B, Huh7 and G1 cells were mock-treated or treated with CAR.hYP7 T cells. As shown in FIG. 5, CAR.hYP7 T cells induce IFN-γ secretion of all three target GPC-positive tumor cells.

Figure 6:
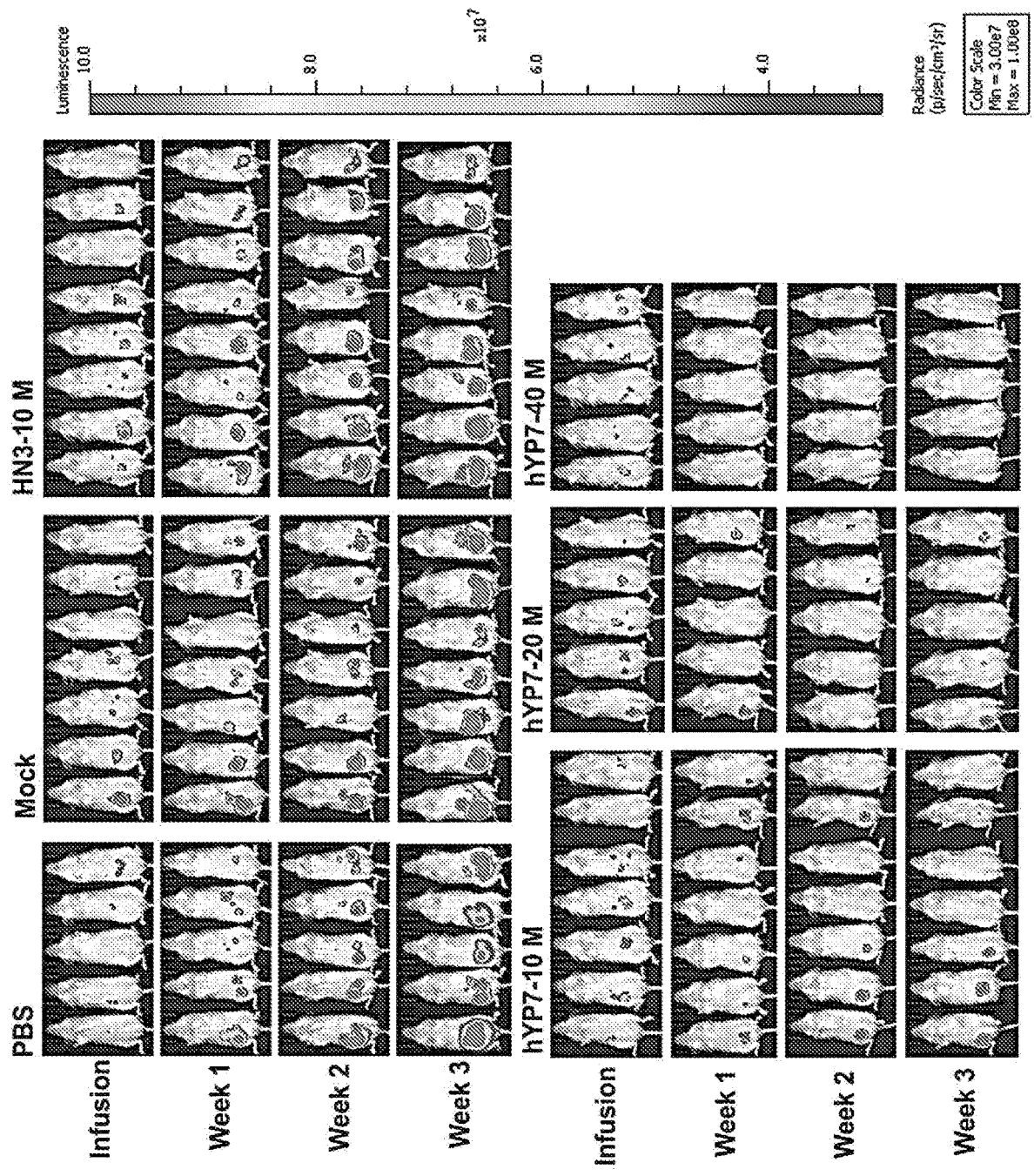
FIG. 6 shows bioluminescence images of Hep3B tumor inhibition in mice treated with GPC3-targeted T cells. Mice were i.p. injected with 4 million Hep3B cells on Day 0. On Day 10, mice were mock-injected or injected with PBS, 10 million CAR.HN3 T cells (HN3-10 M), 10 million CAR.hYP7 T cells (hYP7-10 M), 20 million CAR.hYP7 T cells (hYP7-20 M) or 40 million CAR.hYP7 T cells (hYP7-40 M). Tumor size was measured by bioluminescence imaging.
Figure 8C:
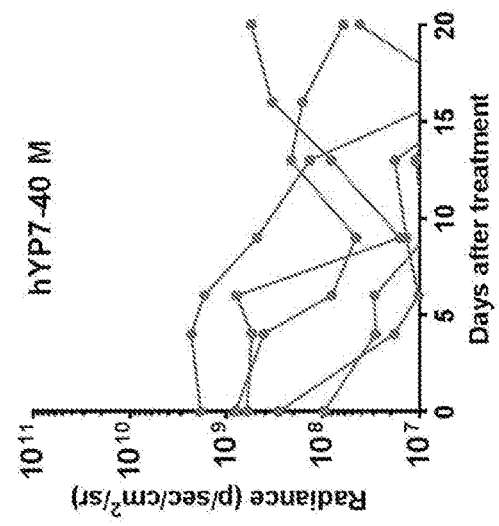
FIGS. 8A-8D are graphs showing tumor volume of HepG2 xenograft NSG mice mock-treated (FIG. 8A) or treated with 10 million CAR.hYP7 T cells (FIG. 8B) or 40 million CAR.hYP7 T cells (FIG. 8C).
Figure 8B:
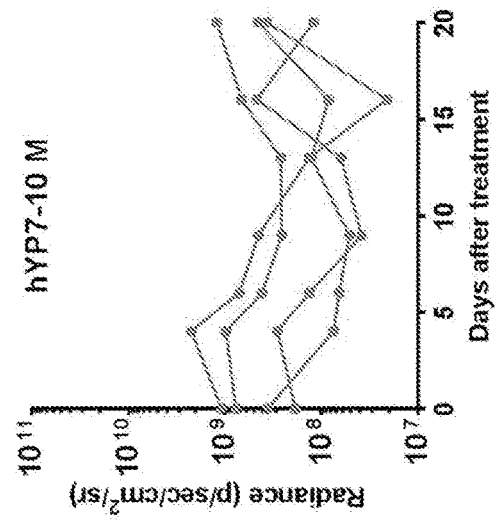
Figure 8A:
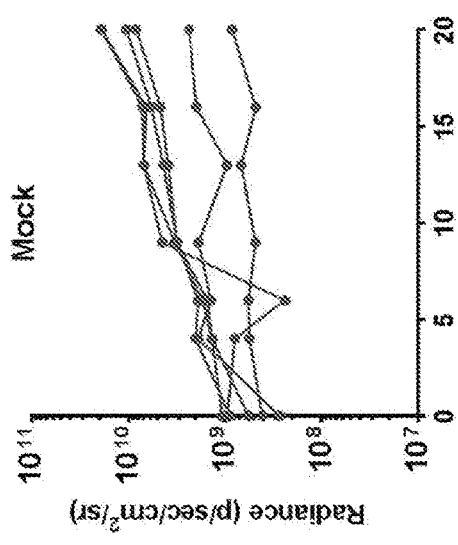
Figure 8D:
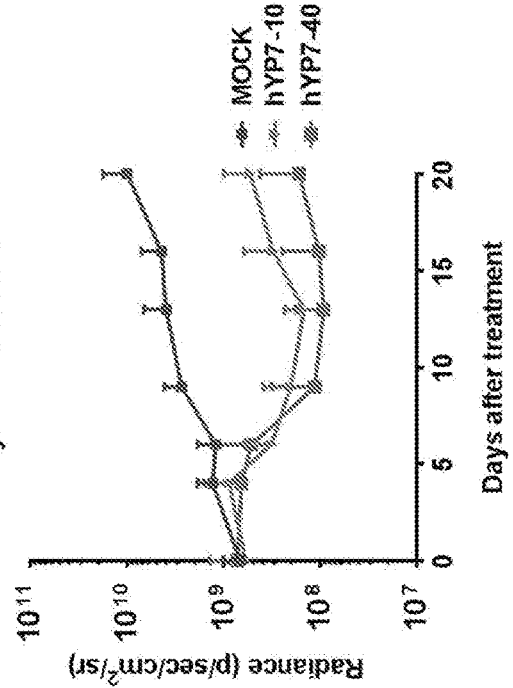

A study was performed to test the ability of GPC3-targeted CAR T cells to inhibit GPC3-positive tumor growth in mice. Mice were i.p. injected with 4 million Hep3B cells on Day 0. On Day 10, mice were mock-injected or injected with PBS, 10 million CAR.HN3 T cells (HN3-10 M), 10 million CAR.hYP7 T cells (hYP7-10 M), 20 million CAR.hYP7 T cells (hYP7-20 M) or 40 million CAR.hYP7 T cells (hYP7-40 M). Tumor size was measured by bioluminescence imaging. Treatment with CAR.hYP7 T cells (at all doses tested) resulted in a significant reduction in tumor volume compared with PBS-treated and mock-treated animals (FIG. 6).

Persistence of the anti-tumor effect of CAR.hYP7 T cells against Hep3B xenograft tumors in mice was also evaluated. Mice were i.p. injected with 4 million Hep3B cells on Day 0. On Day 10, mice were mock-injected or injected with PBS, 10 million CAR.HN3 T cells (HN3-10 M), 10 million CAR.hYP7 T cells (hYP7-10 M), 20 million CAR.hYP7 T cells (hYP7-20 M) or 40 million CAR.hYP7 T cells (hYP7-40 M). First, tumor volume was measured up to 3 weeks post-treatment. Tumors in PBS-treated, mock-treated and CAR.HN3-treated mice steadily increased over time. In contrast, at doses of 10 million and 20 million CAR.hYP7 T cells, tumor volume remained nearly constant over the three weeks, and at a dose of 40 million CAR.hYP7 T cells, tumor volume significantly decreased (FIG. 7A). A second study evaluated anti-tumor activity in Hep3B tumor-bearing mice over the course of seven weeks. This study evaluated mice were treated with PBS, 10 million CAR.HN3 T cells, 10 million CAR.hYP7 T cells or 40 million CAR.hYP7 T cells. The results demonstrated that a dose of 40 million CAR.hYP7 T cells resulted in reducing tumor volume and maintenance of the reduced tumor volume over the seven week study (FIG. 7B). Survival of Hep3B-tumor bearing mice was also evaluated up to 70 days post-Hep3B cell inoculation. This study followed mice that were injected with PBS, 10 million CAR.hYP7 T cells or 40 million CAR.hYP7 T cells. Treatment with 10 million and 40 million CAR.hYP7 T cells led to 50% and 100% survival, respectively. None of the PBS-treated mice survived (FIG. 7C).

Next, CAR.hYP7 T cells were tested in another GPC3-positive tumor model. HepG2 xenograft NSG mice were mock-treated or treated with 10 million CAR.hYP7 T cells or 40 million CAR.hYP7 T cells. As shown in FIGS. 8A-8D, treatment with either dose of CAR.hYP7 T cells resulted in a reduction in tumor volume over the 20-day study period.

Example 4: Materials and Methods for GPC3-Targeted CAR Studies

This example provides the experimental procedures for the studies described in Example 5.

Cell Culture

Human HCC cell line Hep3B was obtained from the National Cancer Institute (NCI), Bethesda, Md. The HepG2 (hepatoblastoma), A431 (epidermal carcinoma), and HEK-293T cell lines were purchased from American Type Culture Collection (ATCC). G1 is a transfected A431 cell line stably expressing human GPC3. Hep3B and HepG2 were transduced with lentiviruses expressing firefly luciferase obtained from NCI Frederick (Day et al., *Pigment Cell Melanoma Res* 22: 283-295, 2009). The luciferase-expressing Huh-7 cell line, an HCC cell line, was obtained from Baylor College of Medicine. The aforementioned cell lines were cultured in DMEM supplemented with 10% FBS, 1% L-glutamine, and 1% penicillinstreptomycin at 37° C. in a humidified atmosphere with 5% $CO_2$. T3M4 (human pancreatic cancer cell line) cells were obtained from the NCI and were engineered to express luciferase. Peripheral blood mononuclear cells (PBMCs) were isolated from the blood of healthy donors by Ficoll (GE Healthcare) according to the manufacturer's instructions. The PBMCs derived from patients with HCC were obtained from the NCI. Jurkat cells were also purchased from ATCC. These cells were grown in RPMI-1640 medium supplemented with 10% FBS, 1% L-glutamine, and 1% penicillinstreptomycin at 37° C. in a humidified atmosphere with 5% $CO_2$. All cell lines were authenticated by morphology and growth rate and were *mycoplasma* free.

Generation of GPC3-Targeted CARs

Figure 10A:
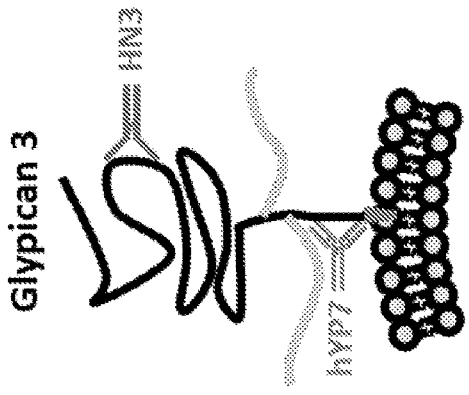
Figure 10B:
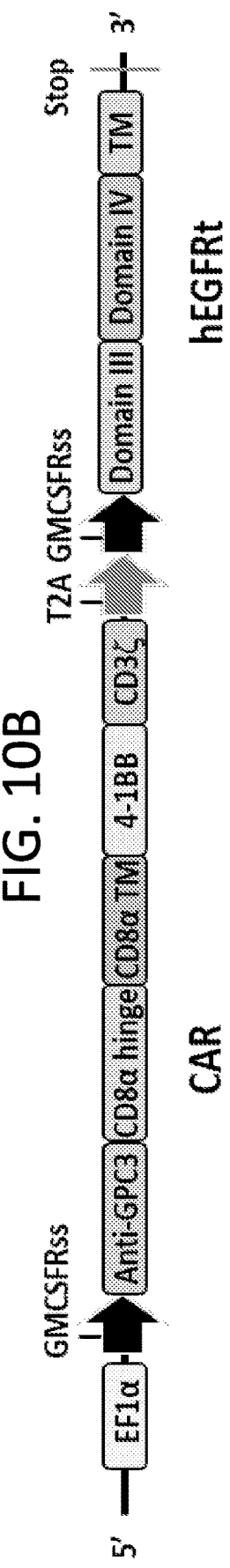

The GPC3-specific scFv from hYP7 and single domain antibody fragment HN3 were subcloned in frame into EF-1α promoter-based lentiviral expressing vector pWPT (Addgene), respectively. The constructs contain expressing cassettes encoding the CD8α hinge and transmembrane regions, a 4-1BB costimulatory domain, intracellular CD3ζ, the self-cleaving T2A sequence, and the huEGFRt as indicated in FIG. 10B (see also Example 1). The final construct was confirmed by sequence analysis.

Lentivirus Production, T-Cell Transduction and Expansion

Recombinant GPC3-CAR lentiviral vectors were produced by co-transfecting with packaging plasmid psPAX2 and enveloping plasmid pMD2.G that were obtained from Addgene into HEK-293T cells using Calfectin (SignaGen). Lentiviral particles were collected from supernatant after 72 hours post-transfection and concentrated 100-fold by Lenti-X concentrator (Clontech) in accordance with manufacturer's instructions. PBMCs were purchased from Oklahoma Blood Institute and stimulated for 24 hours using anti-CD3/anti-CD28 antibody-coated beads (Invitrogen) at a bead to cell ratio of 2:1 according to the manufacturer's instructions in the presence of IL-2. CAR T cells were produced as described previously (Li et al., *Proc Natl Acad Sci USA* 114: E6623-E6631, 2017). To track T cell numbers overtime, viable cells were counted using trypan blue.

Flow Cytometry

The transduction efficiencies of GPC3 CARs on T cells were detected by anti-EGFR human monoclonal antibody cetuximab (Erbitux) and goat-anti-human IgG-phycoerythrin (PE) or allophycocyanin (APC)-conjugated antibody (Jackson ImmunoResearch). CAR expression on Jurkat T cells was measured using GPC3-hFc fusion protein and goat-anti-human IgG-PE-conjugated antibody. The PE-conjugated anti-CD3, anti-CD4, and anti-CD8 antibodies were obtained from eBioscience. Data acquisition was performed using FACSCanto II (BD Biosciences) and analyzed using FlowJo software (Tree Star).

Cytotoxicity Assay

The cytotoxicity of T cells transduced with GPC3-specific CARs was determined by a luciferase-based assay as described previously (Li et al., *Proc Natl Acad Sci USA* 114: E6623-E6631, 2017). Briefly, CAR T cells and luciferase-expressing GPC3-positive (G1, Hep3B, HepG2, Huh-7) and GPC3-negative (A431, T3M4) tumor cells were incubated for 24 hours at different effector to target (E:T) ratios. Luciferase activity was measured using the luciferase assay system (Promega) on Victor (PerkinElmer). Cytotoxicity of the CAR-expressing T cells was also tested by using the IncuCyte-FLR-Platform (Essen BioScience). Briefly, T cells were added into GFP-expressing HepG2 tumor cells at an E:T ratio of 2:1. Images were taken every 2 minutes up to 140 hours. The number of live cells was quantified based on GFP expression. The cell killing activity was analyzed using the IncuCyte Zoom liver cell imaging system.

Cytokine Assay

Cytokine levels in supernatant collected after 24 hours of co-culture of T cells and tumor cells were analyzed using the human cytokine 22-plex panel (granzyme B, GM-CSF, IFN-γ, TNF-α, IL-1β, IL-2, IL-4, IL-5, IL-6, IL-7, IL-10, IL-12, IL-13, IL-15, IL-21, CCL-3, CCL-4, CCL-19, CCL-20, CX3CL1, CXCL-11, CXCL-8) on the Luminex system (Thermo Fisher Scientific).

T Cell Polyfunctionality Evaluation by Single-Cell Cytokine Profiling

Cryopreserved CAR T cell products were thawed and cultured in complete RPMI 1640 media with IL-2 (10 ng/ml). After overnight recovery, viable CAR T cells were enriched using Ficoll. $CD4^+/CD8^+$ T cell subsets were separated using anti-CD4 or anti-CD8 microbeads (Miltenyi Biotec) and stimulated with Hep3B or G1 cells at a ratio of 1:1 for 20 hours. Next, a single cell functional profile was determined using the methods described previously (Ma et al., *Cancer Discov* 3: 418-429, 2013; Rossi et al., *Blood* 132: 804-814, 2018; Xue et al., *J Immunother Cancer* 5: 85, 2017). Profiles were categorized into effector (granzyme B, IFN-γ, CCL-3, Perforin, TNF-α, TNF-β), stimulatory (GM-CSF, IL-2, IL-5, IL-7, IL-8, IL-9, IL-12, IL-15, IL-21), regulatory (IL-4, IL-10, IL-13, IL-22, TGF-β1, sCD137, sCD40L), chemoattractive (CCL-11, IP-10, CCL-4, RANTES), and inflammatory (IL-1β, IL-6, IL-17A, IL-17F, MCP-1, MCP-4) groups. Polyfunctional CAR product T cells were defined as cells co-secreting at least 2 proteins from the prespecified panel per cell coupled with the amount of each protein produced. Furthermore, the PSI of each sample was computed using a prespecified formula (Ma et al., *Cancer Discov* 3: 418-429, 2013), defined as the percentage of polyfunctional cells, multiplied by mean fluorescence intensity (MFI) of the proteins secreted by those cells.

Immunohistochemistry

The human HCC tissue and normal tissue microarrays were purchased from US Biomax, and immunostained with the anti-GPC3 antibody YP7. All tissue samples were sent to Histosery Inc. (Germantown, Md.) for staining Human Normal Tissue cDNA Array The human normal tissue array was purchased from Origene. The panel containing 48 samples covering all major human normal tissues at different locations. The GPC3 primer and RT2 SYBR Green qPCR Mastermix were purchased from Qiagen. Real-time quantification was performed on an Applied Biosystems 7900HT real-time PCR system. The results were analyzed using the 2-ΔΔCt method.

Western Blotting

Cells were lysed with ice-cold lysis buffer (Cell Signaling Technology), and clarified by centrifugation at 10,000 g for 10 minutes at 4° C. Protein concentration was measured using a Bicinchoninic acid assay (Pierce) following the manufacturer's specifications. Twenty μg of cell lysates were loaded onto a 4-20% SDS-PAGE gel for electrophoresis. The anti-GPC3 antibody YP7 is described in PCT Publication No. WO 2013/181543 and Phung et al. (*MAbs* 4(5):592-599, 2012). The anti-active-β-catenin antibody was obtained from Millipore. All other antibodies were obtained from Cell Signaling Technology.

CRISPR/Cas9-Mediated Editing of GPC3

The sgRNAs targeting different exons of GPC3 are listed in the following table. The lentiCRISPRv2 expression vector is a product of Addgene (plasmid #52961). Briefly, the vector was digested with BsmBI and gel purified using a Gel Extraction Kit (Qiagen). A pair of oligonucleotides for each targeting site were annealed and ligated into linearized lentiCRISPRv2 vector for generating a gRNA-expressing plasmid, following the protocol as described previously (Sanjana et al., Nat Methods 11: 783-784, 2014; Shalem et al., Science 343: 84-87, 2014). A sgRNA targeting GPC2 was used as control.

Hep3B were transfected with gRNA-expressing plasmids using LIPOFECTAMINE 2000 (Thermo Fisher Scientific) according to the manufacturer's specifications. Cells were then incubated at 37° C. for 72 hours post-transfection. The effect of different gRNA-expressing plasmid on cell proliferation was determined using crystal violet assay.

| sgRNA | SEQ ID NO: | Sequence | GPC3 exon |
|---|---|---|---|
| sgRNA 1-1 | 43 | GCAGTCTCTGGAAGAAGGAG | 1 |
| sgRNA 1-2 | 44 | TGGTGACAGGTGGCGTCCGG | 1 |
| sgRNA 2 | 45 | CGGTTTTCCAAGGTGAGTTC | 2 |
| sgRNA 3-1 | 46 | GGTCACGTCTTGCTCCTCGG | 3 |
| sgRNA 3-2 | 47 | GACATCAATGAGTGCCTCCG | 3 |
| sgRNA 4 | 48 | GATAATAAGCAGATCTATAT | 4 |
| sgRNA 5-1 | 49 | CGTTTTCCGCCACAGGGCTA | 5 |
| sgRNA 5-2 | 50 | AGGGTGTCGTTTTCCGCCAC | 5 |
| Control sgRNA | 51 | GAGGCAGAGCAGGTAGTCAG | GPC2 |

AFP Assay

Serum AFP levels were determined using an enzyme-linked immunosorbent assay (GenWay Biotech) according to the manufacturer's instructions.

Droplet Digital PCR

Genomic DNA from T cells was isolated using the FlexiGene DNA kit (QIAGEN). Droplet digital PCR was performed on a QX200 droplet digital PCR system (Bio-Rad) according to the manufacturer's instructions.

Animal Studies

Five-week-old female NOD/SCID (NSG) mice (NCI Frederick) were housed and treated under an approved protocol. For the established intraperitoneal (i.p.) Hep3B and HepG2 models, 3 million luciferase-expressing Hep3B or 2 million luciferase-expressing HepG2 tumor cells were injected intraperitoneally (i.p.) into mice. To deplete host lymphocyte compartments, all mice were injected i.p. with 200 mg/kg cyclophosphamide 24 hours before CAR T cell infusion. For the Hep3B model, mice were randomly allocated into six groups and separately injected via i.p. with varying CAR T cells only once as follows: (a) saline only without T cells (PBS); (b) 5 million non-transduced T cells (Mock); (c) 5 million CAR (HN3) T cells; (d) 5 million CAR (hYP7) T cells; (e) 10 million CAR (hYP7) T cells; or (f) 20 million CAR (hYP7) T cells. For the HepG2 model, mice were randomly allocated into two groups including mock and CAR (hYP7). For the established orthotopic Hep3B model, mice were inoculated with 0.5 million luciferase-expressing Hep3B cells in the liver. After 3 weeks of tumor establishment, mice were infused with CAR (hYP7) T cells intraperitoneally or intravenously once. To detect the tumor growth and survival of mice bearing HCC xenografts, all mice were injected i.p. with 3 mg D-luciferin (PerkinElmer) and imaged 10 minutes later every week using Xenogen IVIS Lumina (PerkinElmer). Living Image software was used to analyze the bioluminescence signal flux for each mouse as photons per second per square centimeter per steradian (photons/s/cm$^2$/sr). Mice were euthanized when bioluminescence signal reached $5 \times 10^{10}$.

To measure the effect of GPC3 knockout on HCC tumor cell growth, 2 million Hep3B cells were injected subcutaneously into nude mice. After a tumor formed and reached a size of 100 mm$^3$, the treatment was started by intratumoral injection of sgRNA5-2-expressing plasmid or empty vector every other day for a total of 5 injections. Tumor dimensions were determined twice a week with a caliper. Tumor volume in cubic millimeters was calculated by the formula: (a)×(b$^2$)×0.5, where "a" is tumor length and "b" is tumor width in millimeters.

Toxicological Analysis

Three NSG mice from each group were chosen for toxicology studies. Samples were processed for completed blood counts (CBC), comprehensive serum chemistry (VetScan, Abaxis Veterinary Diagnostics, Union City, Calif.) and internal organ weights. These analyses were performed by the Pathology/Histotechnology Laboratory in NCI-Frederick, Md.

Statistics

All experiments were repeated a minimum of three times to determine the reproducibility of the results. Data were analyzed using Prism (GraphPad Software) software and are presented as mean±SEM. Results were analyzed using unpaired Student's t test (2-tailed). A P value of <0.05 was considered statistically significant. All statistical analyses were performed with Prism software.

Example 5: Glypican 3-Targeted Chimeric Antigen Receptor T Cells for Treatment of Hepatocellular Carcinoma This example describes the finding that T cells expressing huEGFRt and a binding fragment of anti-GPC3 antibody hYP7 exhibit significant anti-cancer activity and robust T cell activation and expansion in mouse models of hepatocellular carcinoma.

GPC3 Expression in HCC and Normal Tissues

Figure 9:
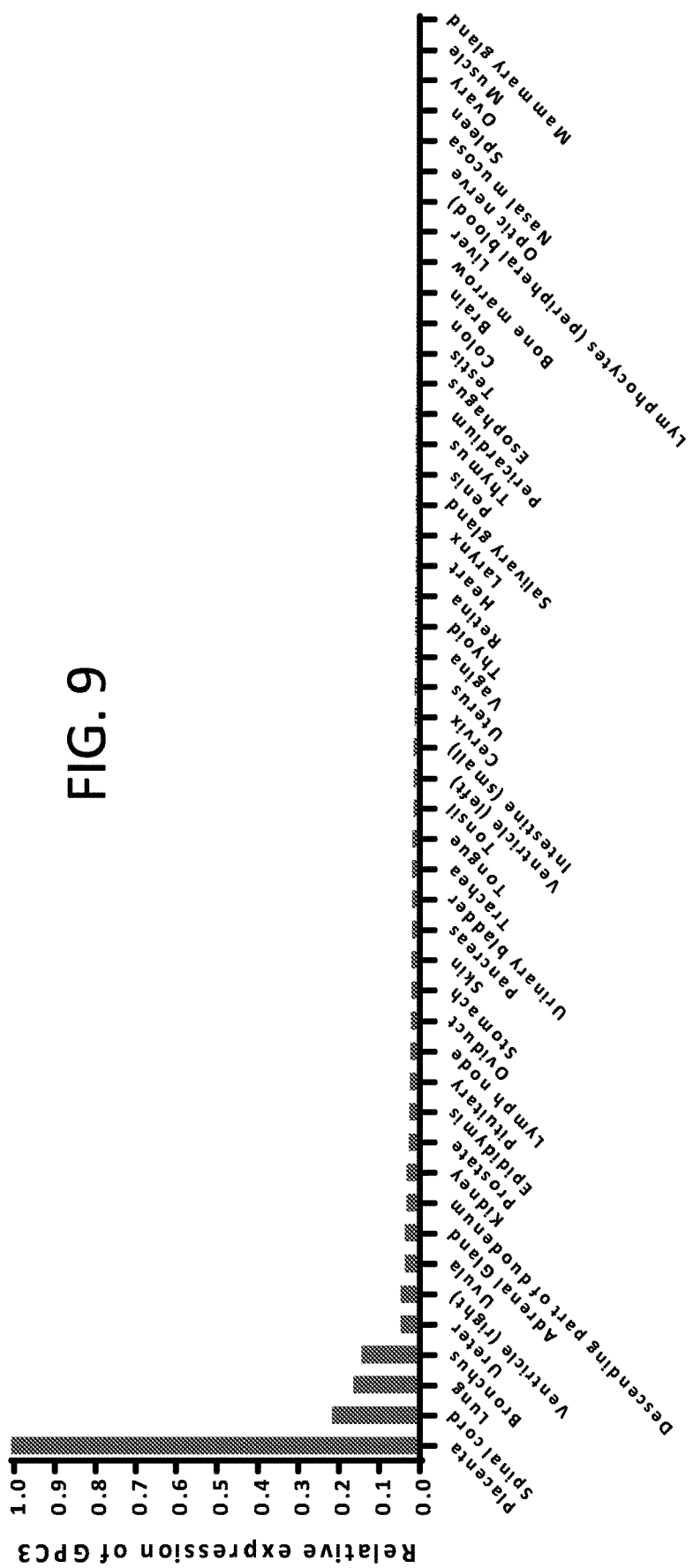
FIG. 9 shows GPC3 mRNA levels in human normal tissues as measured by quantitative real-time PCR. The relative GPC3 levels in different normal tissues were compared to GPC3 expression in placenta.

To analyze the GPC3 expression in tumors and normal tissues, the YP7 antibody was used to examine 46 pairs of tumor and adjacent non-tumor tissues (hepatic cirrhosis or hepatitis) from patients with HCC by immunohistochemistry. The GPC3 protein was highly expressed in 50% (23/46) of primary HCCs compared with only 2% (1/46) of matched tumor-adjacent tissues. Strong GPC3 staining was found in 24 of 40 additional cases of HCC tissues (60%), but not in any normal liver tissues. A concern for CAR T-cell therapy is the potential for on-target, off-tumor toxicities due to expression of antigen on normal tissues. Here, GPC3 expression was analyzed in 30 types of human normal tissues. Notably, GPC3 protein was absent in all the essential normal tissues including brain, heart, lung, stomach, small intestine, colon, kidney, pancreas, spleen, nerve and skin. Among all the normal tissues, a low level of GPC3 protein expression was detected only in testis. GPC3 mRNA levels were also measured in a human normal tissue array by quantitative real-time PCR. Consistent with protein profiles, GPC3 mRNA expression was not found in a majority of normal tissues except placenta (FIG. 9), which was consistent with a previous report of GPC3 expression in human placenta (Khan et al., Histol Histopathol 16: 71-78, 2001). Cell surface expression of GPC3 was then examined on a panel of cancer cell lines by flow cytometry. YP7 showed strong binding to HCC cell lines (Hep3B, HepG2 and Huh-7) as well as a GPC3 overexpressing-A431 cell line (G1). By contrast, YP7 exhibited no binding to A431 and T3M4 cells, revealing that GPC3 expression detected by the YP7 antibody is highly tumor specific.

Generation of GPC3-specific CAR T cells

Figure 10E:
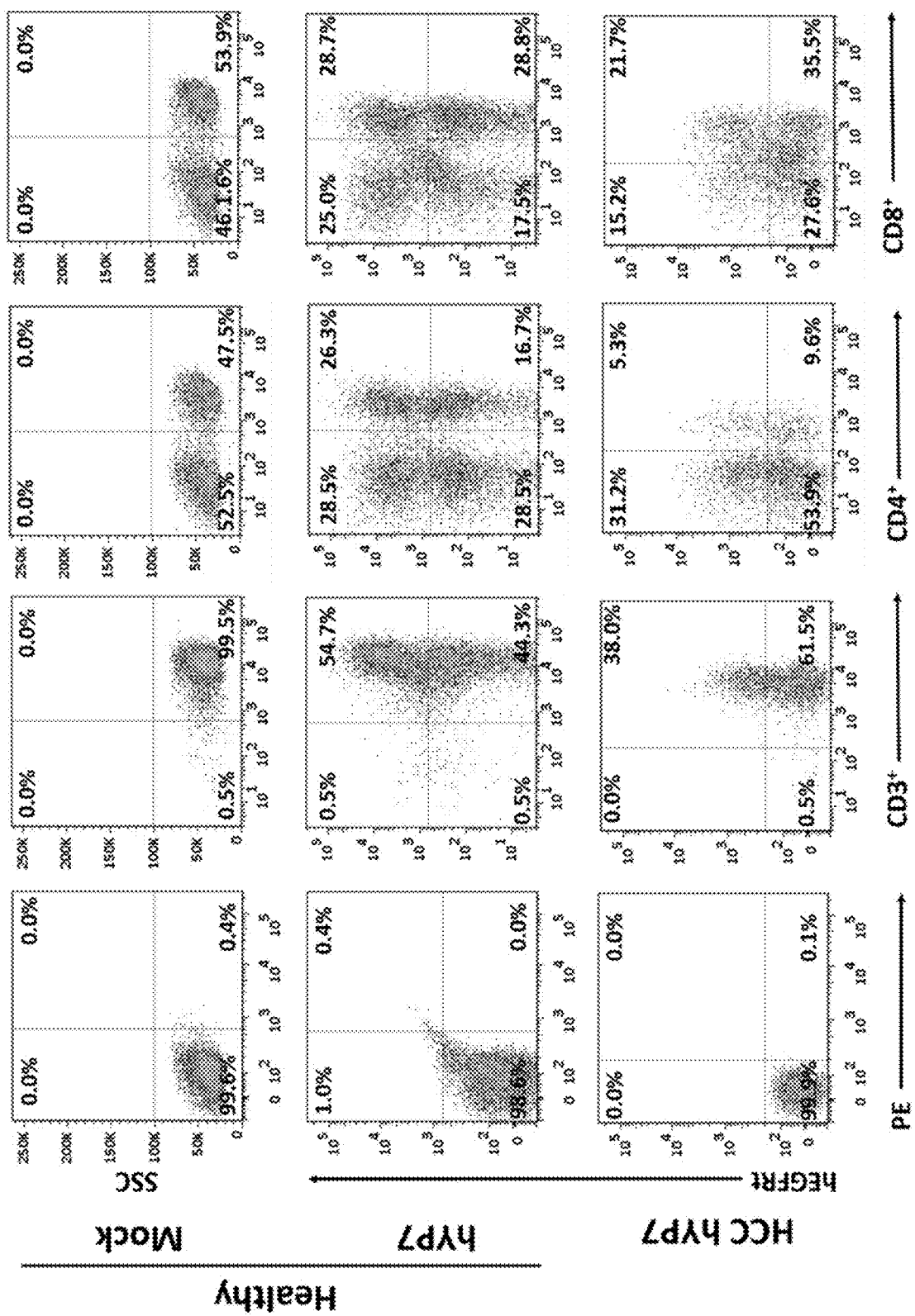

Human single domain antibody HN3 recognizes the N-lobe of GPC3 (FIG. 10A) (Feng et al., *Proc Natl Acad Sci USA* 110: E1083-1091, 2013). The YP7 antibody (hYP7) that targets the C-lobe of GPC3 was also humanized to reduce the risk of immunogenicity (Zhang and Ho, *Sci Reports* 6: 33878, 2016). The variable region of the HN3 or the hYP7 antibody was cloned in frame into a lentiviral vector containing CAR expression cassettes with 4-1BB and CD3ζ endodomains (FIG. 10B) (see also Example 1). To facilitate cell tracking and ablation, the truncated human epidermal growth factor receptor (huEGFRt) was incorporated into the construct and separated from the CAR by a T2A ribosomal skip sequence. The huEGFRt lacks the domains essential for ligand binding and tyrosine kinase activity but retains the binding epitope of anti-EGFR monoclonal antibody cetuximab (Wang et al., *Blood* 118: 1255-1263, 2011). As shown in FIG. 2B, the CAR plasmids are transduced into the primary T cells from either heathy donors or HCC patients, expanded in vitro for 10-12 days, and then tested in HCC cell and animal models. The expression of GPC3-targeted CARs was determined by flow cytometry. Both CARs were efficiently expressed on the surface of human Jurkat T cells as detected by recombinant GPC3-human Fc (hFc) fusion protein. In addition, the expression of CARs on human primary T cells was demonstrated through cell surface huEGFRt expression. As shown in FIG. 10C, the transduction efficiencies of CAR (HN3) and CAR (hYP7) were 76% and 58%, respectively. After expansion for 11 days in vitro, more than 99% of CAR (hYP7) T cells derived from healthy donor became CD3-positive, which were comprised of similar frequency of $CD4^+$ (43%) and $CD8^+$ (56%) T cell subsets (FIG. 10D). Notably, the proportion of $CD4^+$ T cells (14.9%) was significantly lower than $CD8^+$ T cells (57.2%) in a HCC patient-derived CAR (hYP7) T cells. Strikingly, 27.9% of $CD3^+CD4^-CD8^-$ T cells, known as 'double negative' (DN) T cells, were detected in HCC patient-derived CAR (hYP7) T cells. As seen in FIG. 10E, CAR (hYP7) T cells from 8 different healthy donors displayed 15- to 60-fold expansion after initial priming with anti-CD3/CD28 beads over 11 days. By comparison, CAR (hYP7) T cells from 4 patients with HCC only expanded 5- to 25-fold at Day 11 following activation. Taken together, the CAR T cells based on the HN3 and hYP7 antibodies have similar values in their expression levels, binding avidity for GPC3, transduction efficiencies and $CD4^+/CD8^+$ T cell ratios. The primary T cells derived from HCC patients were able to express CARs and expand in culture.

In Vitro Antitumor Activity of GPC3-Targeted CAR T Cells

Figure 11A:
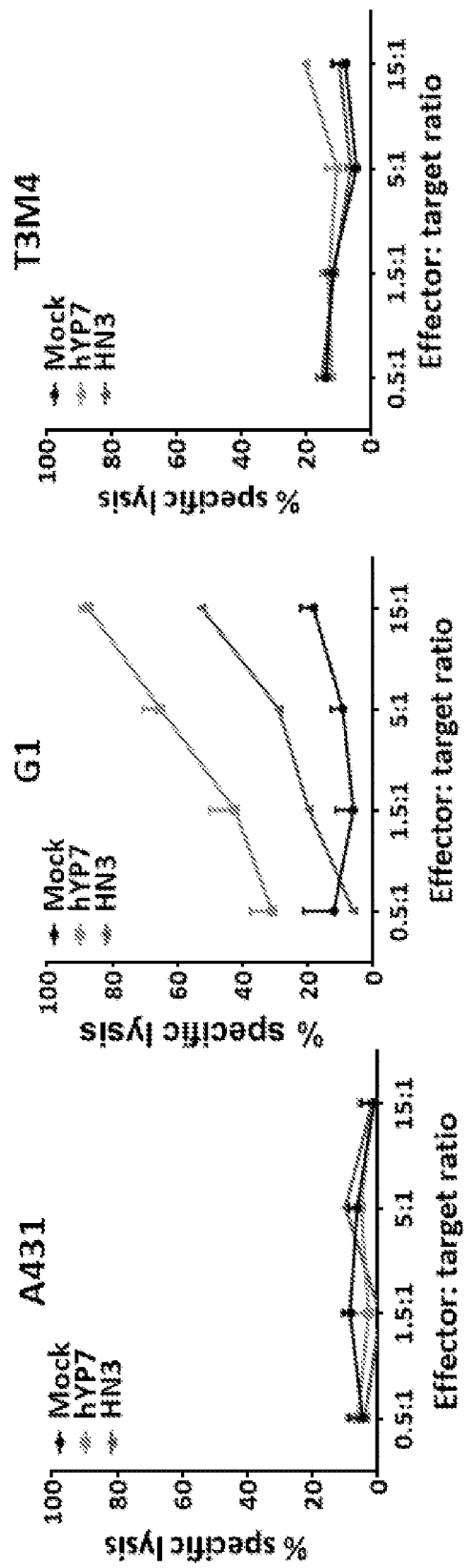
FIGS. 11A-11G are graphs showing that the GPC3-targeted CAR T cells kill GPC3-positive HCC cells in vitro.
Figure 11B:
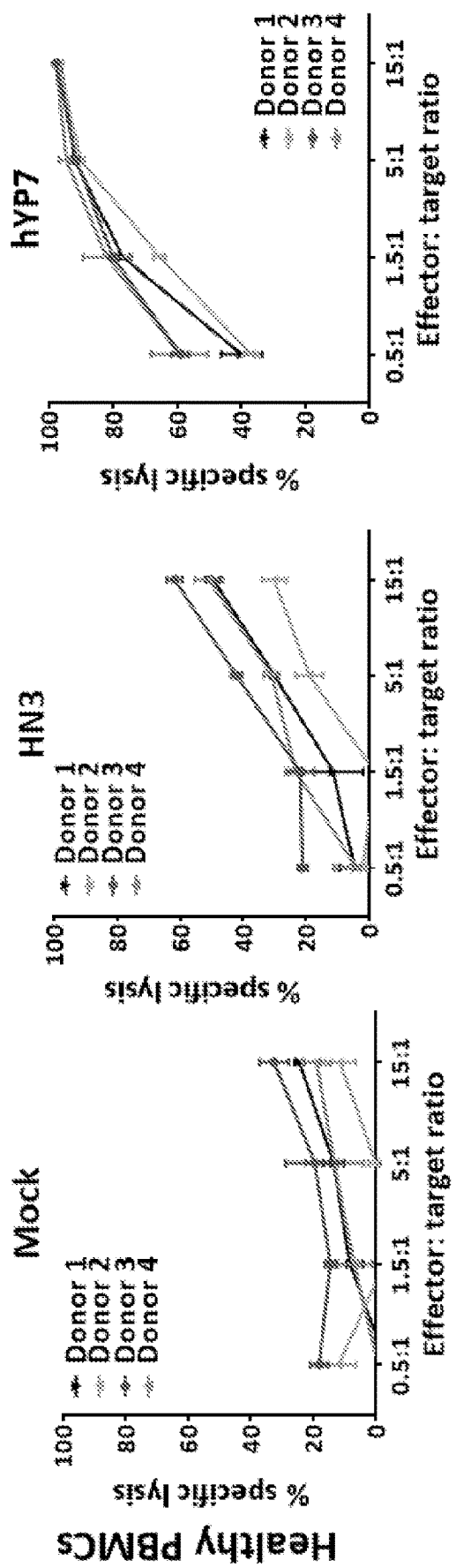
Figure 11C:
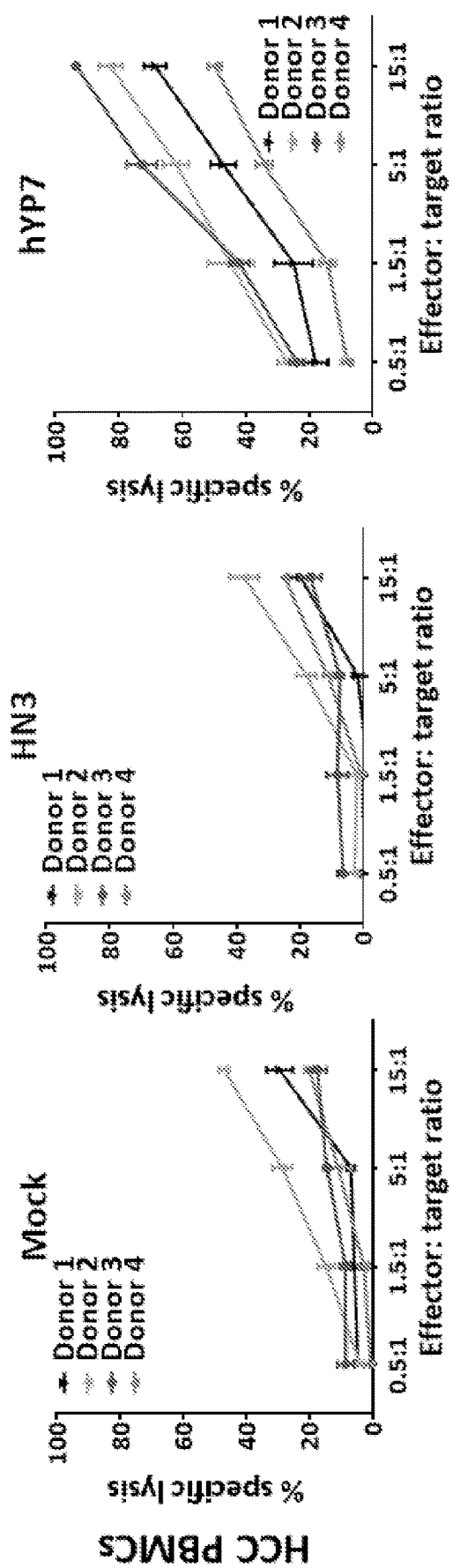
Figures 11D, 11E:
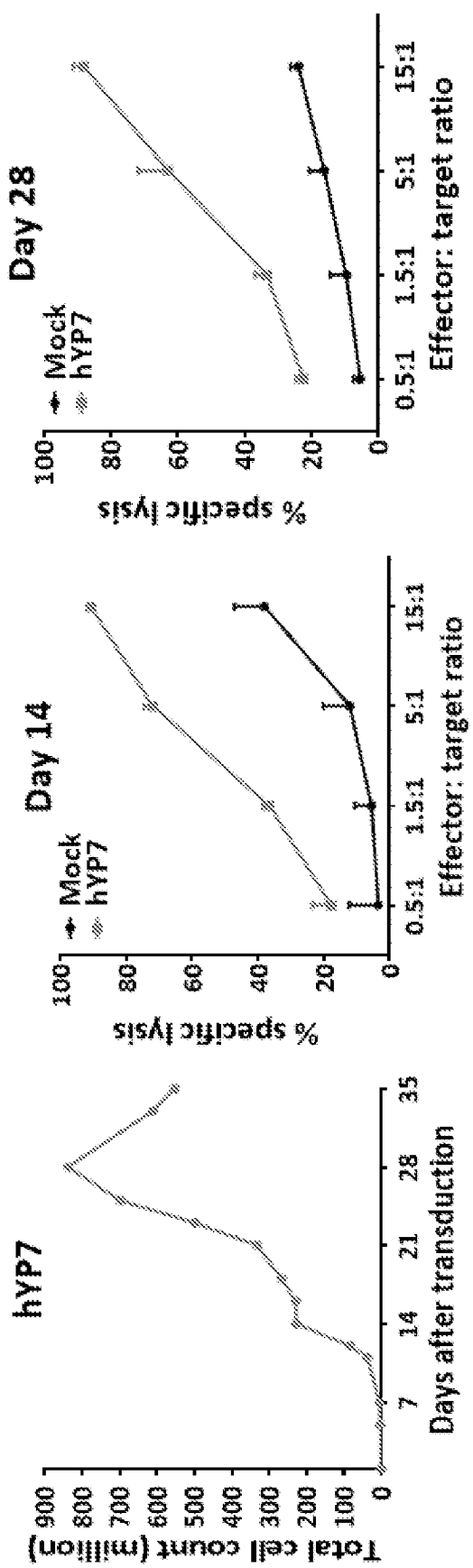
Figures 11F, 11G:
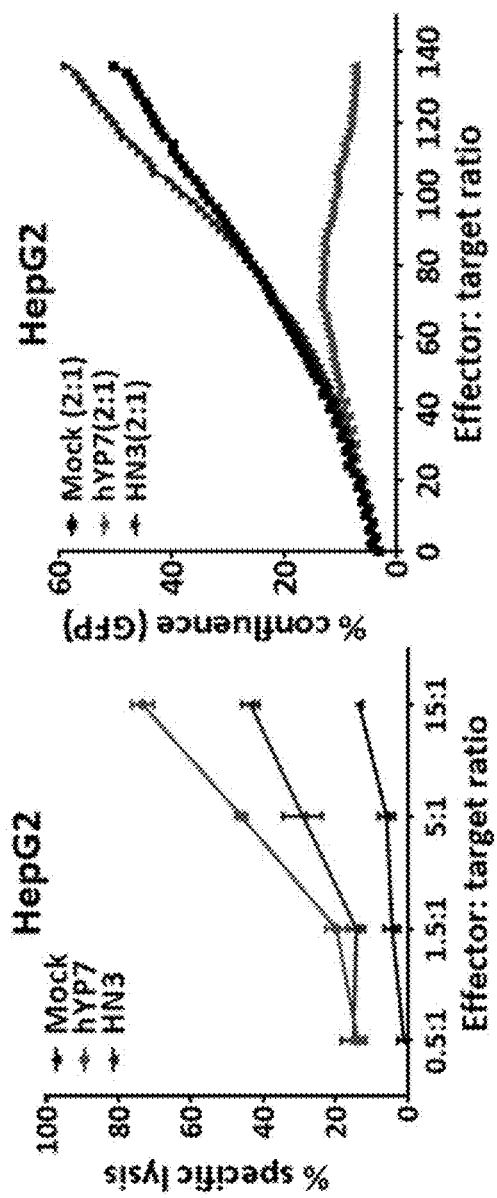

To determine whether T cells targeting GPC3 could specifically recognize and kill GPC3-positive tumor cells, a cytolytic assay was established using luciferase-expressing tumor cells. As shown in FIG. 11A, GPC3-overexpressing A431 (G1) cells were efficiently lysed by both CAR (HN3) and CAR (hYP7) T cells in a dose-dependent manner. By contrast, both CAR T cells showed minimal cytolytic activity against GPC3-negative cells including A431 and T3M4, indicating specificity of the CART cells. Cytolytic capability of GPC3-targeted CAR T cells derived from healthy donors and HCC patients was also compared. The CAR (hYP7) T cells appeared to have higher lytic activity than CAR (HN3) T cells at various E:T ratios on Hep3B cells (FIG. 11B and FIG. 11C). At the E:T ratio of 5, the lytic activity of HCC patient-derived CAR (hYP7) T cells against Hep3B cells ranged from 30% to 70%, with an average of 50% (FIG. 11C), which was lower than the averaged activity (90%) of healthy donor-derived CAR (hYP7) T cells (FIG. 11B). In comparison, minimal cell lysis was observed in Hep3B cells treated with any source of mock T cells. Interestingly, CAR (hYP7) T cells were able to undergo long-term expansion through initial activation with anti-CD3/CD28 beads (FIG. 11D). The CAR (hYP7) T cells induced similar levels of cell death in Hep3B cells at Day 14 or Day 28 (FIG. 11E). In addition to Hep3B cells, GPC3 CAR T cells were tested in other HCC cell lines including HepG2 and Huh-7. As shown in FIG. 11F, HepG2 and Huh-7 cells were lysed by CAR (HN3) and CAR (hYP7) T cells to a lesser extent than Hep3B cells that express a high level of GPC3. To determine whether GPC3-targeted CAR T cells can result in increased tumor cell lysis during extended periods of co-culture, CAR (HN3) or CAR (hYP7) CAR T cells were incubated with HepG2 cells at an E:T ratio of 2:1 over 140 hours. Initially, neither CAR T cells killed HepG2 cells compared with mock T cells. At and beyond 40 hours, CAR (hYP7) T cells were significantly more potent in eliminating HepG2 cells compared with CAR (HN3) T cells (FIG. 11G). Collectively, CAR (hYP7) T cells exhibit better cytolytic ability than CAR (HN3) T cells when co-cultured with GPC3-positive tumor cells.

In Vitro Multiplex Cytokine and Chemokine Profiles of GPC3-Targeted CAR T Cells

Figure 12A:
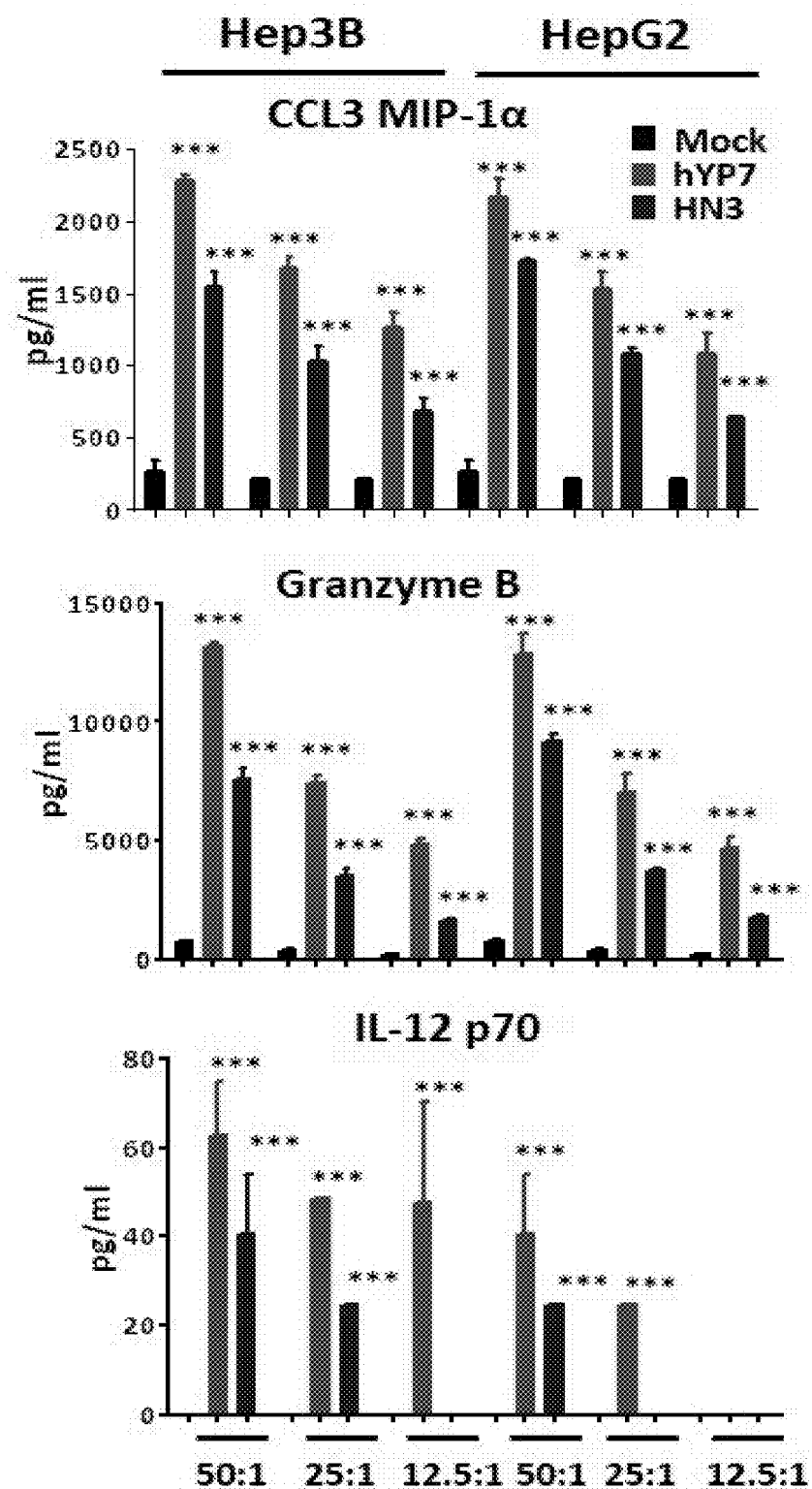
FIGS. 12A-12C shows cytokine/chemokine profiles and polyfunctionality of T cells redirected with GPC3-CARs. Hep3B and HepG2 cells were co-cultured with GPC3-targeted CAR T cells for 24 hours at various E:T ratios and the indicated cytokine/chemokine levels in supernatants were measured using Luminex. Bars are from left to right: Mock, hYP7 and HN3. Mean and SD are shown. *p<0.05; p<0.01; *p<0.001.
Figure 12B:
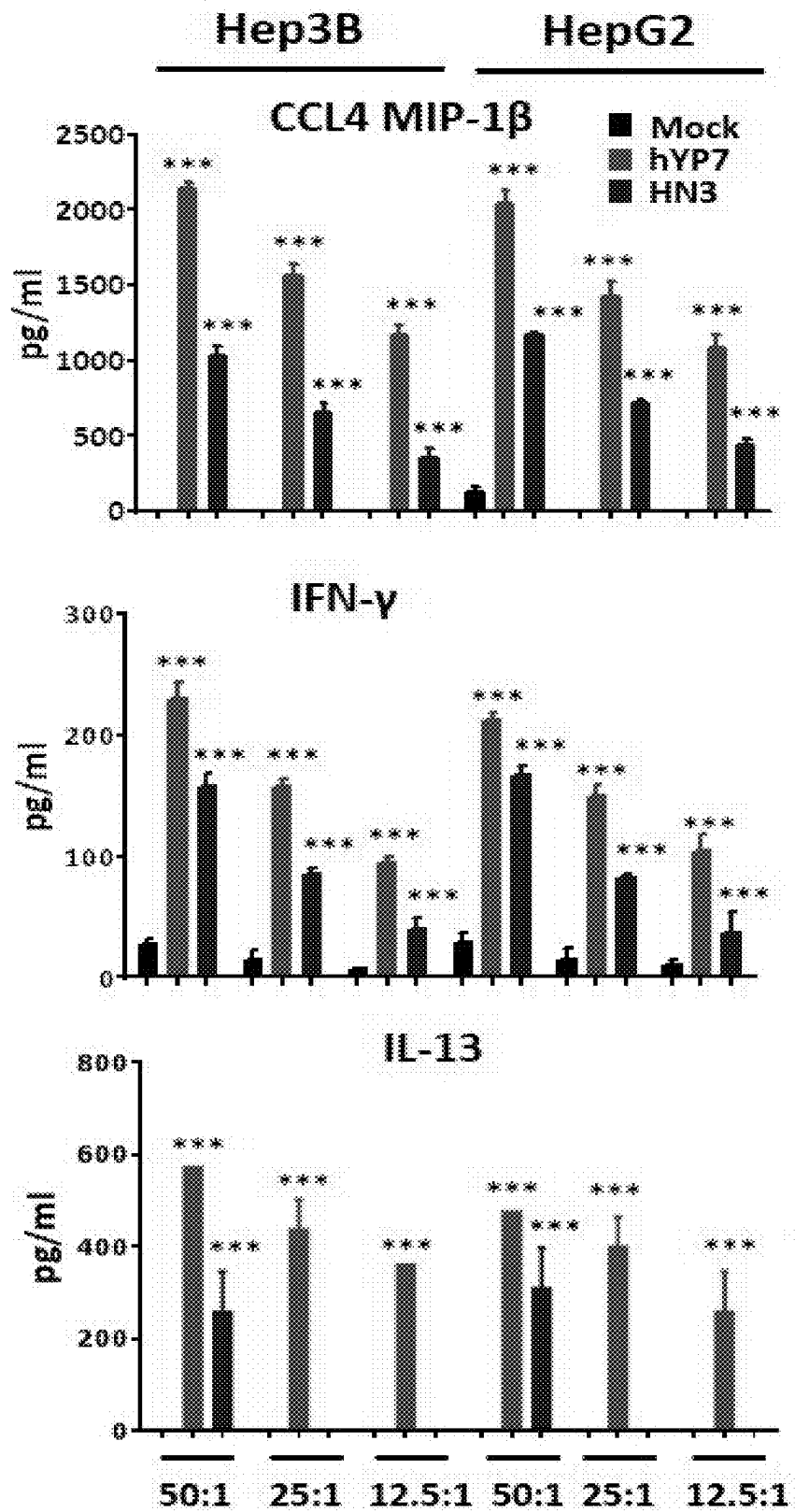
Figure 12C:
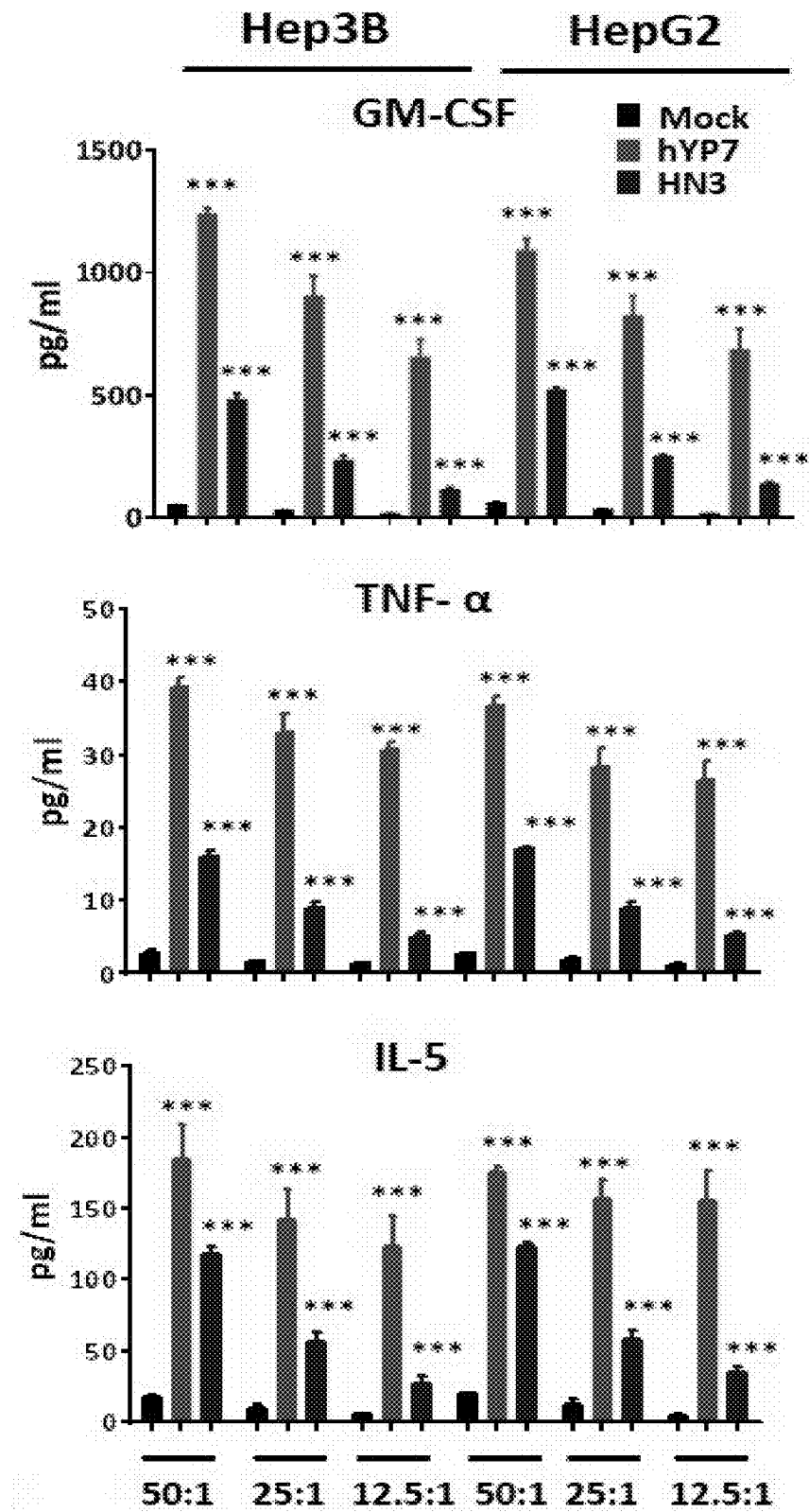
Figure 18:
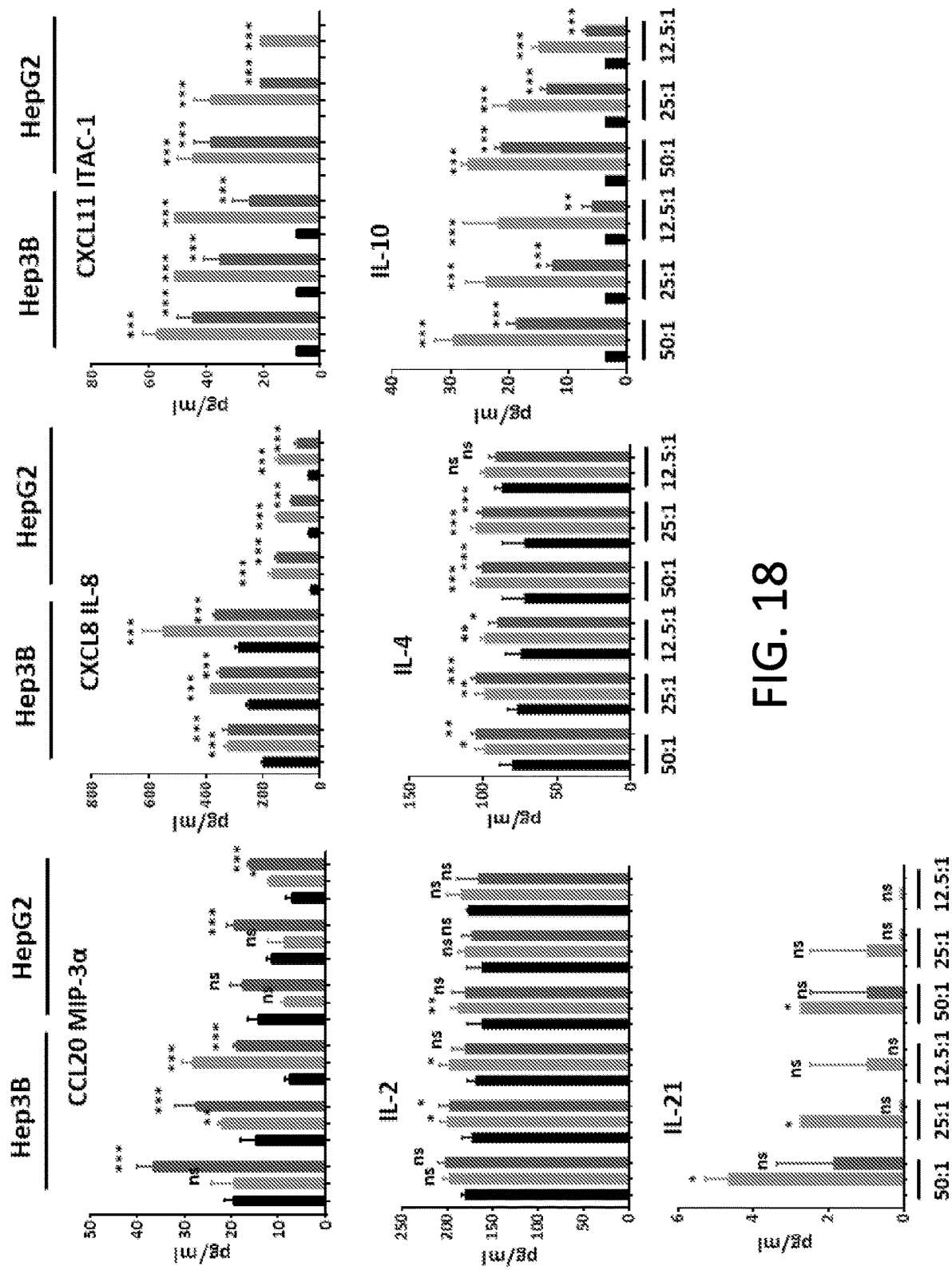
FIG. 18 is a series of graphs showing differential cytokine and chemokine secretion measured by Luminex after incubation of GPC3-targeted CAR T-cell with both Hep3B and HepG2 tumor cells for 24 hours. Bars are from left to right: Mock, hYP7 and HN3. * P<0.05,  P<0.01, * P<0.001.

Having established that GPC3-targeted CAR T cells could recognize GPC3-positive tumor cells in an antigen-specific manner, studies were conducted to determine the effects of 4-1BB on cytokine and chemokine profiles from CAR (HN3) or CAR (hYP7) T cells following exposure to Hep3B or HepG2 cells. As shown in FIGS. 12A-12C, in the presence of GPC3-positive tumor cells, greater amounts of all cytokines were produced by GPC3-specific CAR T cells than mock-transduced T cells. Both CAR T cells secreted significantly high levels of granzyme B (2500-13000 pg/mL) when co-cultured with Hep3B or HepG2 cells for 24 hours (FIG. 12A). It was also determined that 4-1BB co-stimulation induced high levels of Th1 cytokines (GM-CSF, IFN-γ, TNF-α and IL-12), and Th2 cytokines (IL-5 and IL-13), which was consistent with a Th1/Th2 phenotype. However, GPC3-specific CART cells only expressed very low levels of IL-21 (<10 pg/mL), which is produced by Th17 cells (FIG. 18). In addition to cytokines, CAR (HN3) and CAR (hYP7) T cells secreted very high levels of CCL-3 and CCL-4 chemokines (400-2225 pg/mL) that may promote infiltration of lymphocytes into tumors (FIGS. 12A-12B). A complete panel of cytokines and chemokines analyzed in this study is shown in FIG. 18. Overall, CAR (hYP7) T cells produced significantly more cytokines and chemokines than CAR (HN3) T cells, which is consistent with the differences in antitumor activities between the two CARs.

Single Cell Based Polyfunctionality Analysis of GPC3-Targeted CAR T Cells

Recent studies demonstrate that T cells capable of co-producing multiple cytokines/chemokines at the single cell level, termed "polyfunctional" T cells, are the key effector cells contributing to the development of potent and durable cellular immunity against cancer (Ahmadzadeh et al., *Blood* 114: 1537-1544, 2009; Baitsch et al., *J Clin Invest* 121: 2350-2360, 2011). To determine the polyfunctionality of our CAR T cell product, a high-content single-cell multiplex cytokine analysis was applied (Lu et al., *Proc Natl Acad Sci USA* 112: E607-615, 2015; Ma et al., *Cancer Discov* 3: 418-429, 2013), which allows for the identification of a subset of polyfunctional T cells that produce 2 or more cytokines upon stimulation with GPC3 antigen in vitro. The 32-plex panel includes the key immune elements of T cells. Hep3B cell-stimulated CAR T cells showed an increase in the percentage of polyfunctional cells compared with mock T cells. CAR (hYP7) T cells had much higher polyfunctionality than CAR (HN3) T cells when stimulated with Hep3B cells. Similarly, enhanced polyfunctionality was observed in both $CD4^+$ and $CD8^+$ CAR T cells when stimulated by G1 cells compared to A431 cell stimulation. It was also noted that $CD8^+$ T cells were more polyfunctional than $CD4^+$ T cells. Moreover, the polyfunctional strength index (PSI) described previously was used to quantify the collective impact of polyfunctional T cells (Ma et al., *Cancer Discov* 3: 418-429, 2013). The PSI of a sample is defined as the percentage of polyfunctional cells multiplied by the average signal intensity of the cytokines secreted by these cells. PSI was broken down by cytokine function—effector, stimulatory, regulatory, and inflammatory—to highlight the contributions of each group to the overall polyfunctionality of the sample. While effector cytokines contributed to all polyfunctionality of $CD4^+$ CAR (hYP7) T cells and the majority of $CD8^+$ CAR (hYP7) T cells, a small percentage of regulatory cytokine sCD137 was observed in $CD8^+$ CAR (hYP7) T cells stimulated by Hep3B cells. Furthermore, more effector and chemoattractive molecules (such as CCL-3 and CCL-4) were produced by $CD8^+$ CAR (hYP7) T cells when co-cultured with G1 cells, which is consistent with the measurement of cytokine release using Luminex assays. To distinguish all polyfunctional subsets within a sample, a polyfunctional heat map visualization was used. CAR (hYP7) T cells had greater frequencies of the most expressed functional groups compared to CAR (HN3) T cells upon stimulation with Hep3B or G1 cells. The 4-plex group containing granzyme B, INF-γ, perforin and sCD137 was expressed by the $CD8^+$ CAR (hYP7) T cells upon Hep3B stimulation. The G1-stimulated $CD8^+$ CAR (hYP7) T cells were more polyfunctional and secreted the 7-plex group containing granzyme B, INF-γ, CCL-3, CCL-4, perforin, TNF-α and sCD137. Taken together, CAR (hYP7) stimulated more robust activation and expansion of polyfunctional T cells, in particular $CD8^+$ cytotoxic T cells.

The Effect of Wnt Signaling on GPC3-Targeted CAR T-Cell Treatment

Figure 13B:
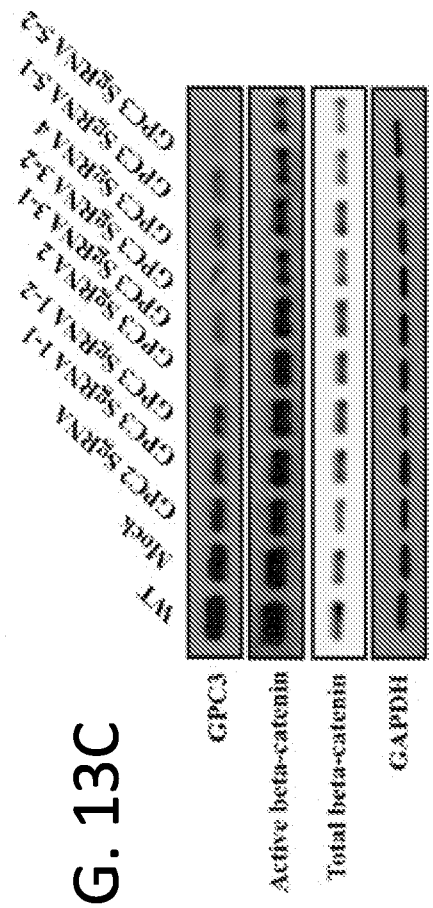
Figure 13C:
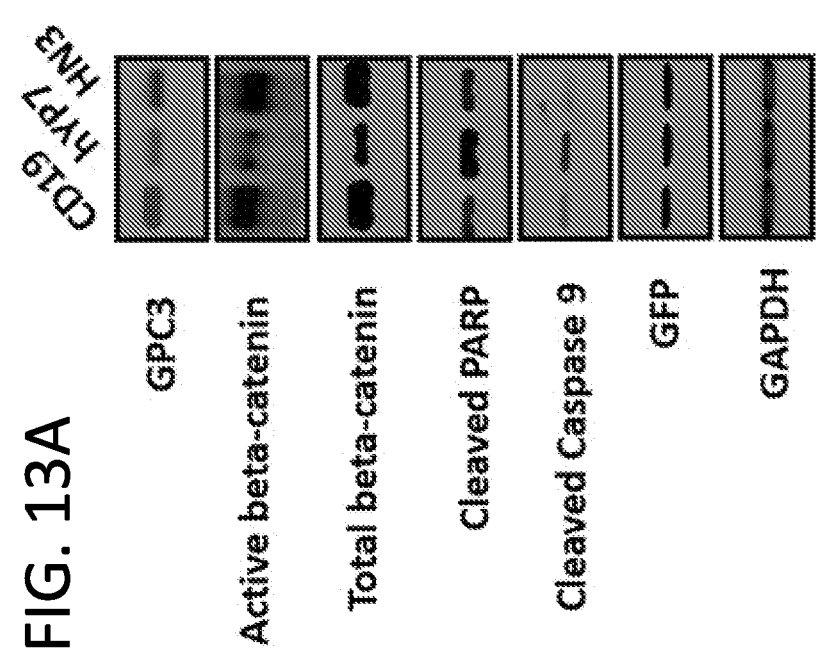
Figure 13A:
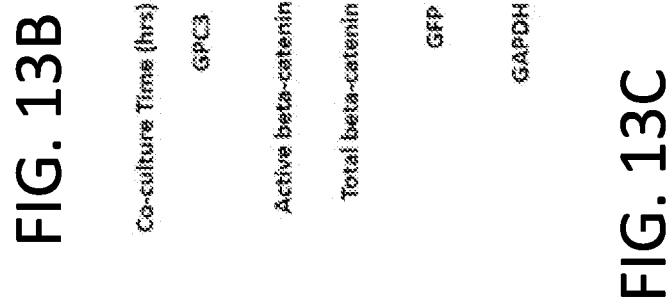

Previous studies have shown that GPC3 interacts with Wnt ligand and promotes HCC cell proliferation by facilitating Wnt/Frizzled binding (Capurro et al., *Cancer Res* 65: 6245-6254, 2005; Gao et al., *Hepatology* 60: 576-587, 2014; Gao et al., *Nat Comm* 6: 6536, 2015). To determine if GPC3-targeted CAR T cells could affect Wnt signaling, active- and total β-catenin levels were measured. As shown in FIG. 13A, CAR (hYP7) T cells significantly reduced the expression of active-β-catenin and total β-catenin compared with mock T cells after 6 hours of co-culture with Hep3B cells at an E:T ratio of 10:1. The reduction in active-β-catenin expression even began at 2 hours of CAR (hYP7) T cell treatment in Hep3B cells (FIG. 13B). In addition, CAR (hYP7) T cells induced apoptosis of Hep3B cells as evidenced by elevated expression of cleaved-Poly (ADP ribose) polymerase (PARP) and cleaved caspase-9. However, CAR (HN3) T cells neither inhibited β-catenin expression nor induced Hep3B cell apoptosis after 6 hours of incubation.

To further investigate if targeting GPC3 downregulates HCC tumor growth via inhibition of Wnt signaling, the CRISPR/Cas9 technique was used to genetically edit the GPC3 gene in Hep3B cells. Transfecting cells with constructs encoding small guiding RNA (sgRNA) targeting different exons of GPC3 led to a substantial decrease of GPC3 protein, particularly exon 5-targeted sgRNA (5-2) reduced over 95% of GPC3 expression (FIG. 13C). The 5-2 sgRNA treatment downregulated the expression of active-β-catenin and total β-catenin (FIG. 13C), and resulted in dramatic cell death. Thus, both CAR (hYP7) T cells and CRISPR/Cas9-mediated gene editing of GPC3 suppress the Wnt/β-catenin signaling in HCC cells. Following in vitro experiments, it was tested whether targeting of GPC3 with the CRISPR/Cas9 platform would impede HCC tumor growth in mice. Hep3B cells were subcutaneously inoculated into nude mice. Four weeks after tumor inoculation, mice were intravenously injected with either empty plasmid or the plasmid encoding 5-2 sgRNA. As shown in FIG. 13D, tumor growth was appreciably suppressed in mice treated with 5-2 sgRNA plasmid compared with mice treated with empty plasmid. Importantly, 5-2 sgRNA treatment also resulted in the decrease of active-β-catenin and total β-catenin protein levels in tumors (FIG. 13E). Alpha fetoprotein (AFP) has been the most widely used biomarker for HCC during the past several decades (IuS, *Vopr Med Khim* 10: 90-91, 1964). The serum concentration of 20 ng/mL is the commonly used cut-off value to differentiate HCC patients from healthy adults (Trevisani et al., *J Hepatol* 34: 570-575, 2001). HCC patients with a high AFP concentration (≥400 ng/mL) tend to have greater tumor size, massive or diffuse types, and a lower median survival rate (Fujioka et al., *Hepatology* 34: 1128-1134, 2001; Tangkijvanich et al., *J Clin Gastroenterol* 31: 302-308, 2000). Serum AFP was measured before and after CRISPR/Cas9-mediated editing of GPC3. As shown in FIG. 13F, AFP serum levels were significantly lower in mice injected with 5-2 sgRNA than those injected with empty plasmid, demonstrating the positive correlation between AFP level and tumor size. Overall, the data indicates that targeting GPC3 may suppress HCC tumor growth by inhibiting Wnt/β-catenin signaling.

CAR (hYP7) T Cells Enable HCC Tumor Regression in Xenograft Mouse Models

Figures 14A, 14B:
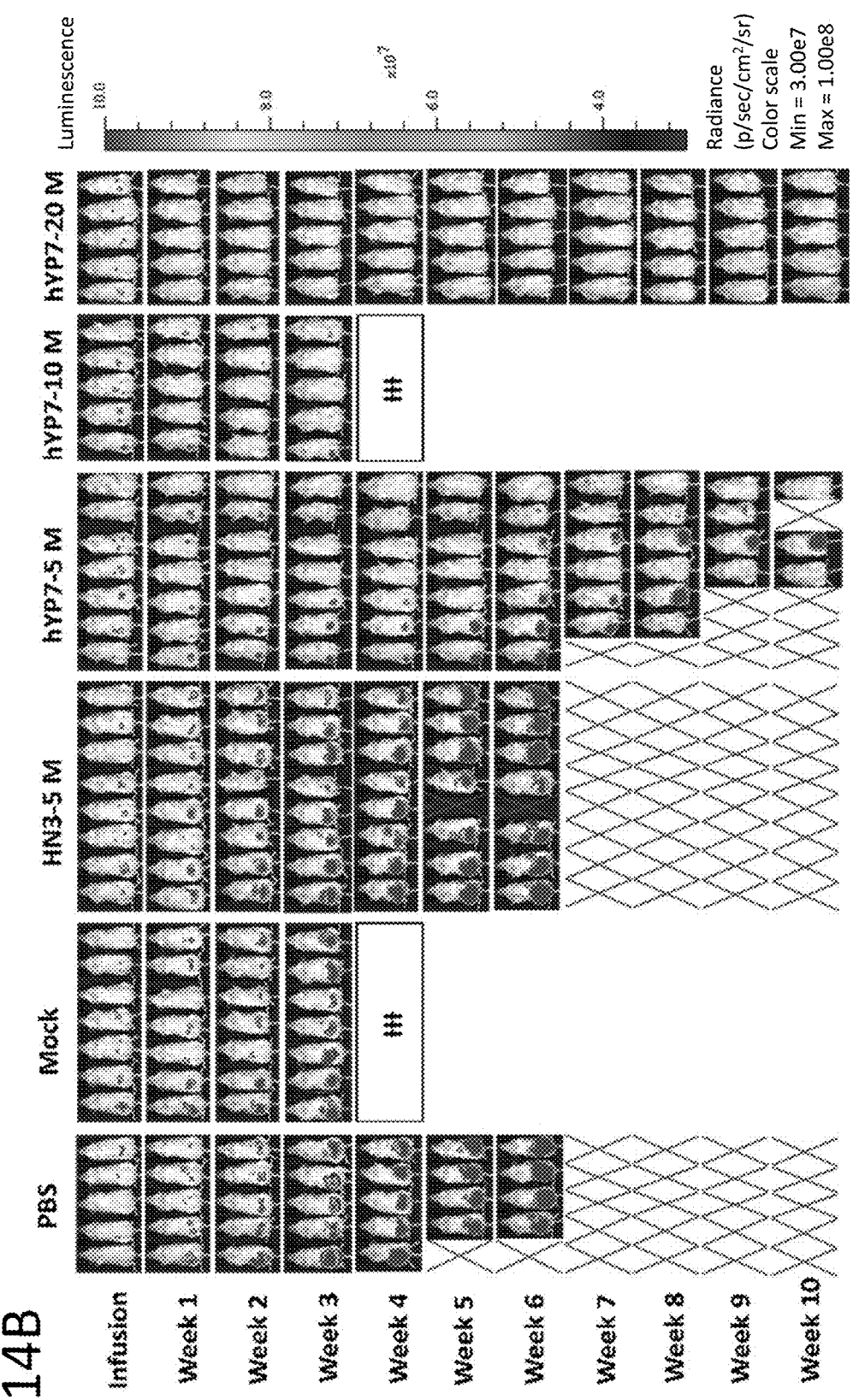
FIGS. 14A-14F show that CAR (hYP7) T cells eradicate tumors in the Hep3B peritoneal dissemination xenograft mouse model.
Figure 14D:
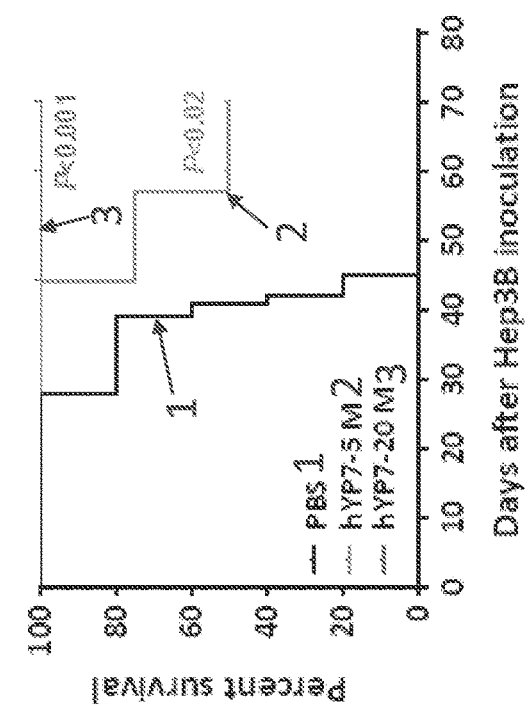
Figure 14C:
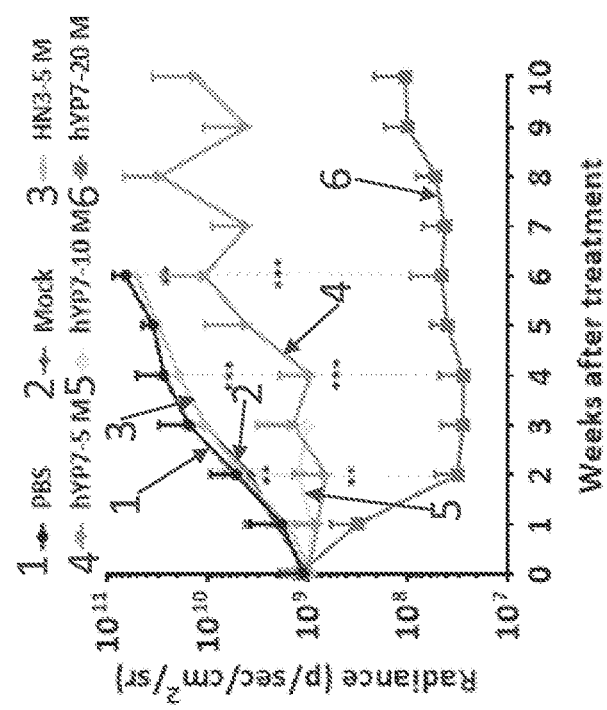
Figure 14E:
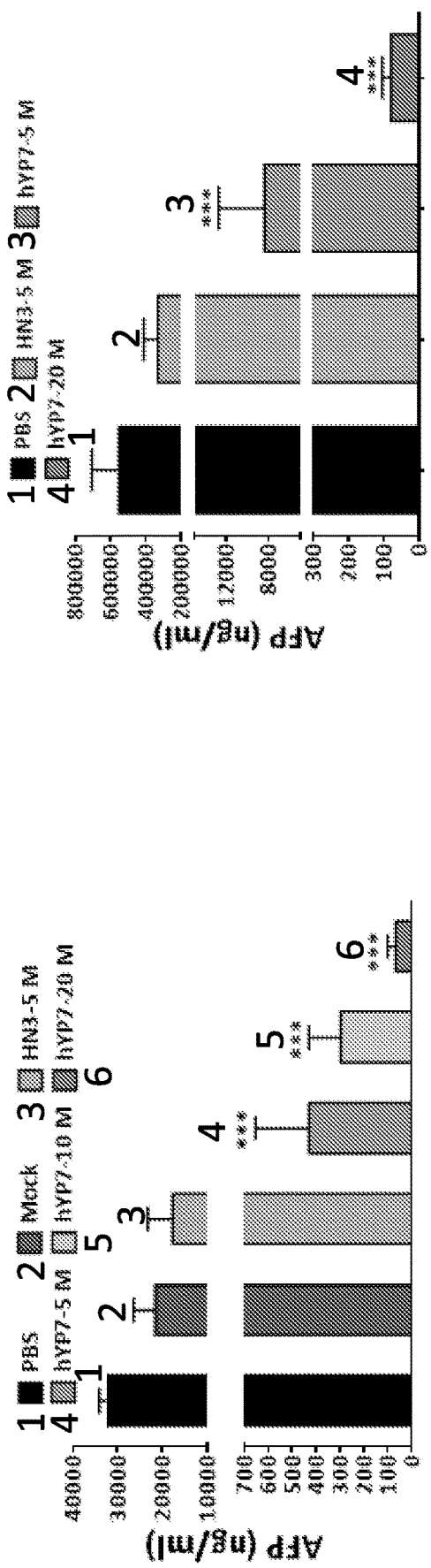
Figure 19A:
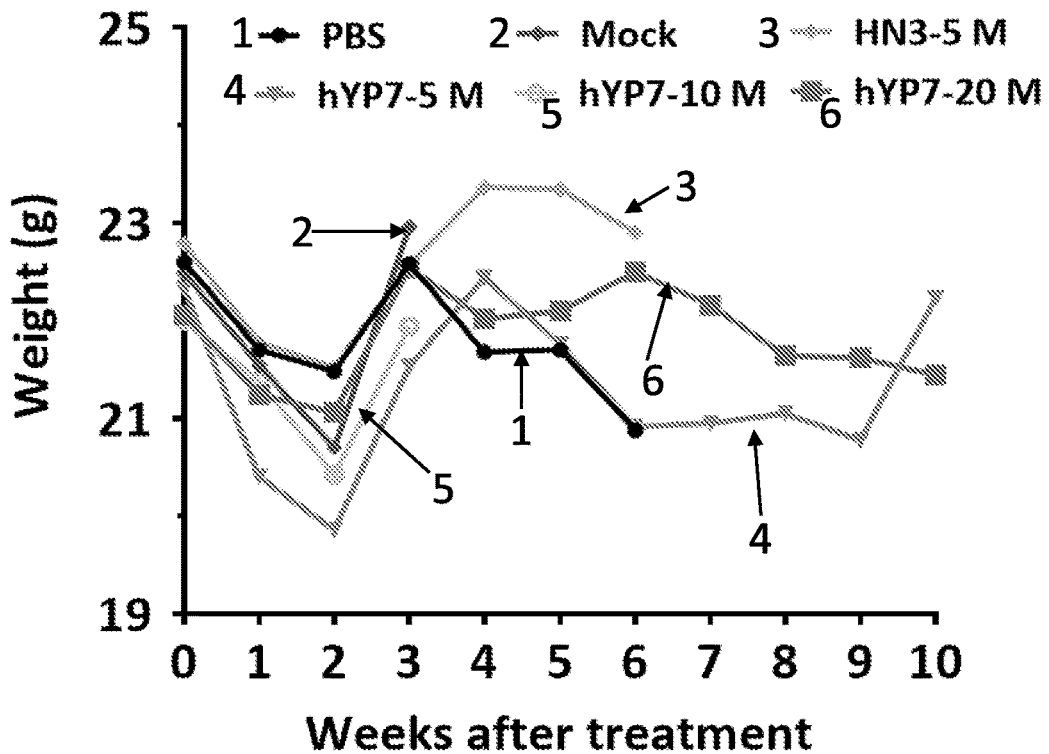
FIGS. 19A-19B show body weight of Hep3B and HepG2 tumor xenograft mice following treatment with GPC3-targeted CAR T cells.

To evaluate the antitumor activities of GPC3-specific CAR T cells in vivo, NSG mice were intraperitoneally injected with luciferase-expressing Hep3B cells (Hep3B-luc). Twelve days later, a single infusion of mock or CAR T cells was administered intraperitoneally (FIG. 14A). Two weeks after treatment, the groups with different doses of CAR (hYP7) T cells all showed reduced tumor burden comparing with the mock T cell-treated group (FIG. 14B and FIG. 14C). Although CAR (HN3) T cells exhibited modest cytolytic activity against Hep3B cells in vitro, no significant tumor growth inhibition was observed in the mice treated with CAR (HN3) T cells. Remarkably, 100% of NSG mice receiving 20 million CAR (hYP7) T cells were alive without recurrence by day 70, compared with only 50% survival in 5 million CAR (hYP7) T cell treatment group (FIG. 14D). Although GPC3-targeted CAR T cells initially caused body weight loss, mice gradually gained weight back (FIG. 19A). Moreover, the serum AFP levels in mice treated with 5 million (mean: 400 ng/mL) or 10 million (mean: 300 ng/mL) CAR (hYP7) T cells were significantly lower than the levels in mock T cell-treated mice (mean: 20000 ng/mL) after two weeks of treatment (FIG. 14E). Notably, the AFP levels in mice treated with 20 million CAR (hYP7) T cells were in the range of 25-78 ng/mL, which was close to the cut-off value (20 ng/mL) in human adults.

Figure 14F:
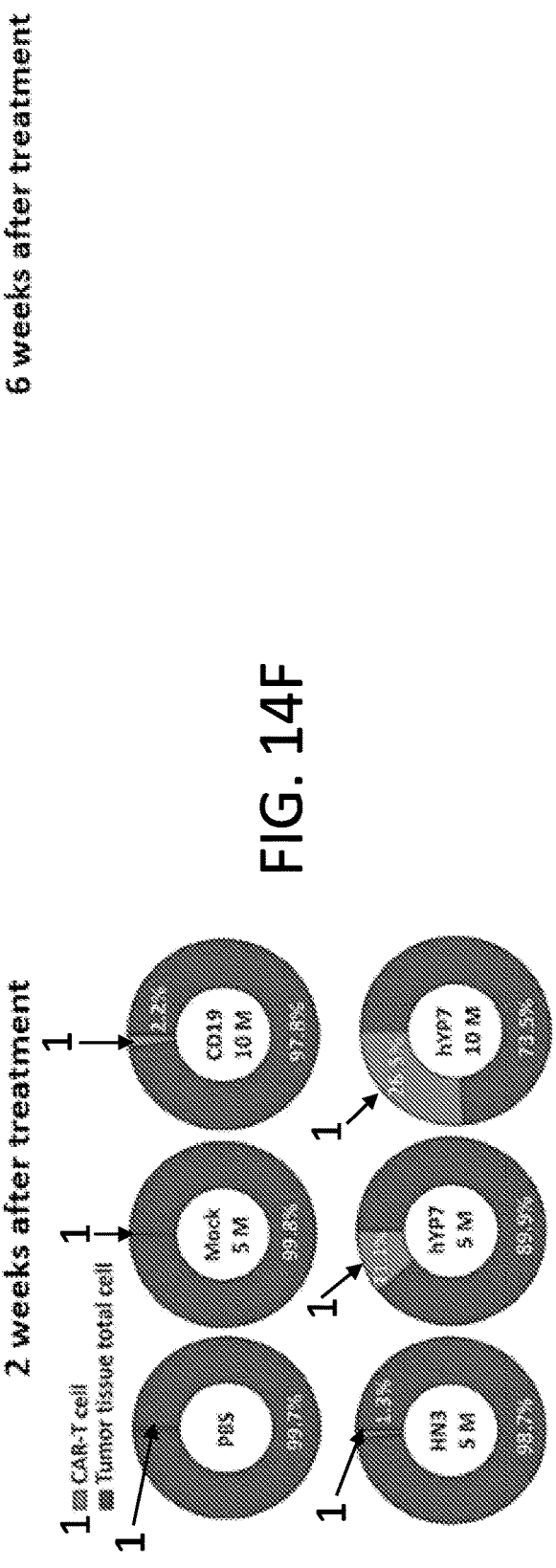

Robust in vivo expansion and persistence of genetically modified T cells are also considered critical predictors of durable clinical remissions in patients with cancer. To understand the persistence of infused CAR T cells, the percentage of CAR T cells was assessed using droplet digital PCR (ddPCR) using CAR-specific amplimers. As shown in FIG. 14F, 22.1% of CAR expression was found in the 5 million CAR (hYP7) group, whereas only 1.3% CAR was detected in 5 million CAR (HN3) group after 3 weeks of treatment. Moreover, 26.5% of CAR integration was detected in 10 million CAR (hYP7) group, demonstrating an inverse correlation between tumor burden and T cell persistence over time. By contrast, only 2.2% of CAR expression was detected in 10 million CD19 CAR T cell-treated mouse, which indicate that tumor antigen recognition drives the survival of infused T cells in vivo.

From the Hep3B peritoneal dissemination mouse model, it was found that mice developed tumor lesions on the liver and other tissues and organs in the abdominal cavity. Interestingly, Hep3B tumors in the mice treated with 5 million CAR (hYP7) T cells grew locally and restricted to the fat tissues far from the mouse liver, suggesting that CAR (hYP7) T cells prevent tumors from seeding and growing in the liver and spreading to other organs such as kidney, lung and heart.

Figure 15A:
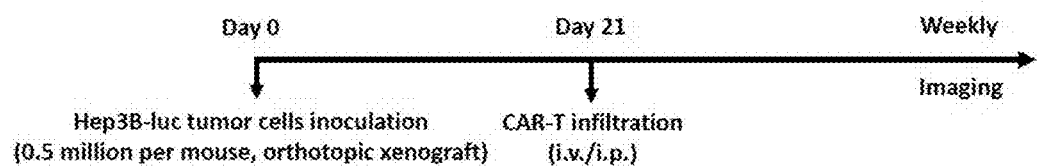
Figure 15B:
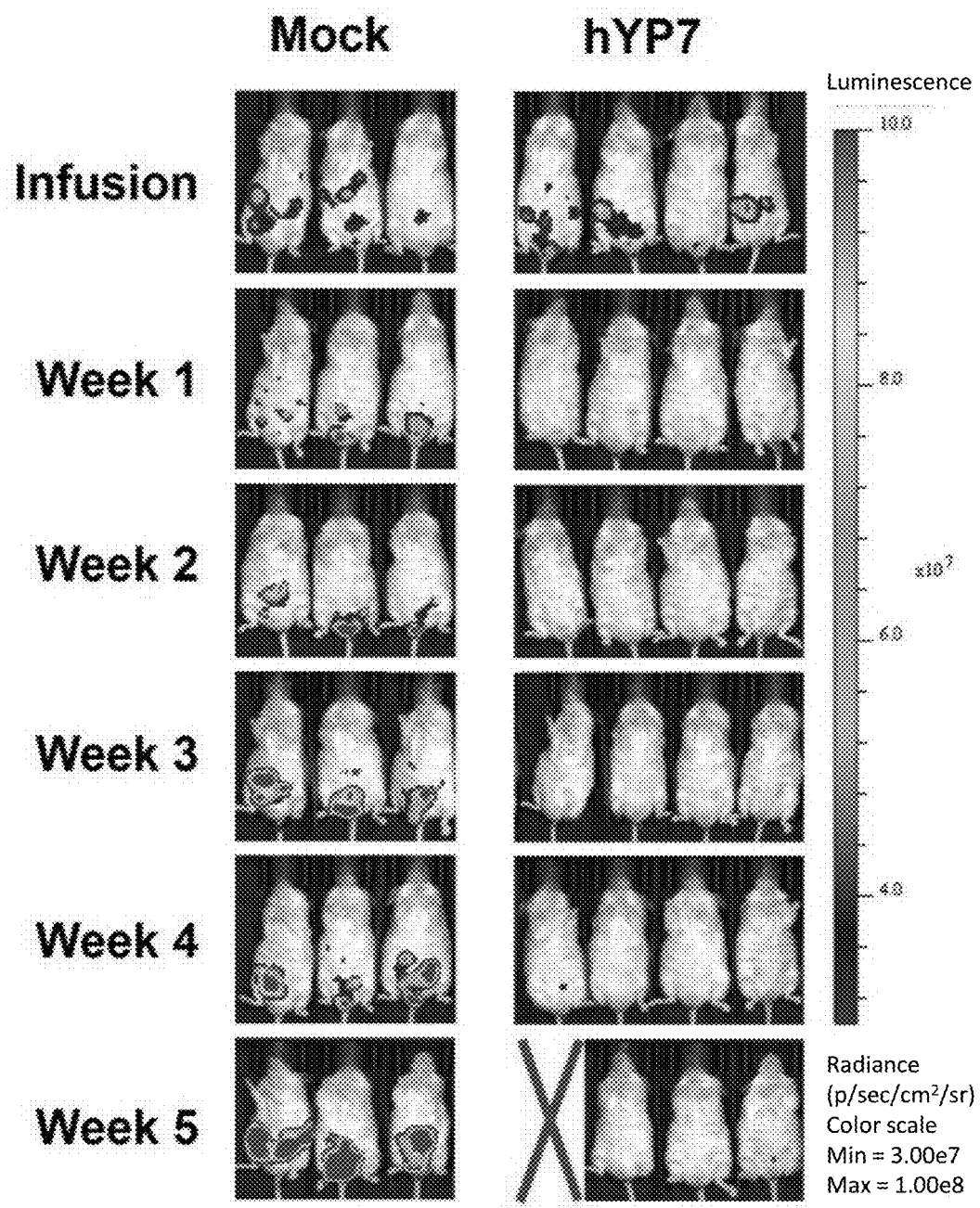
Figure 15D:
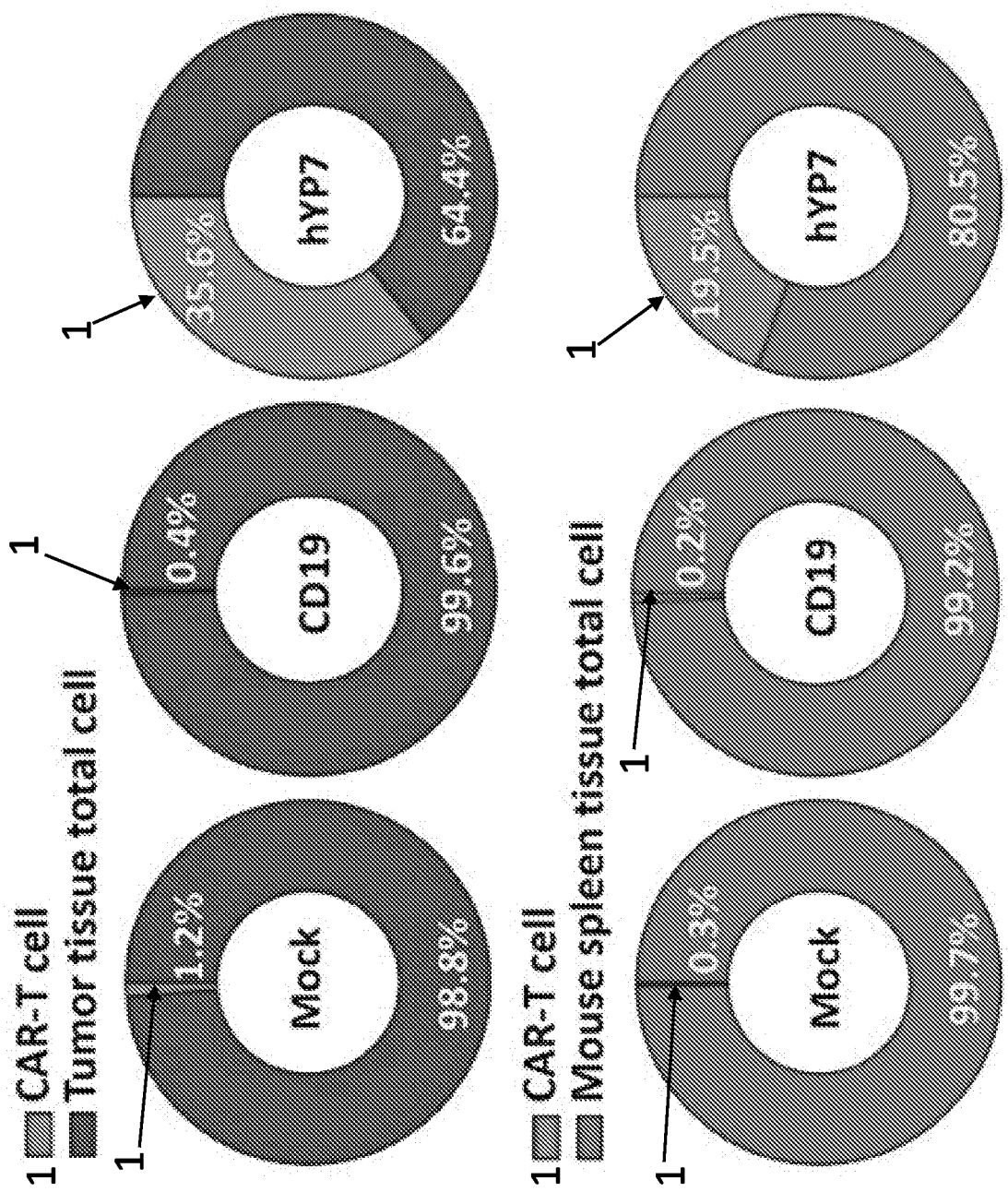
Figure 19B:
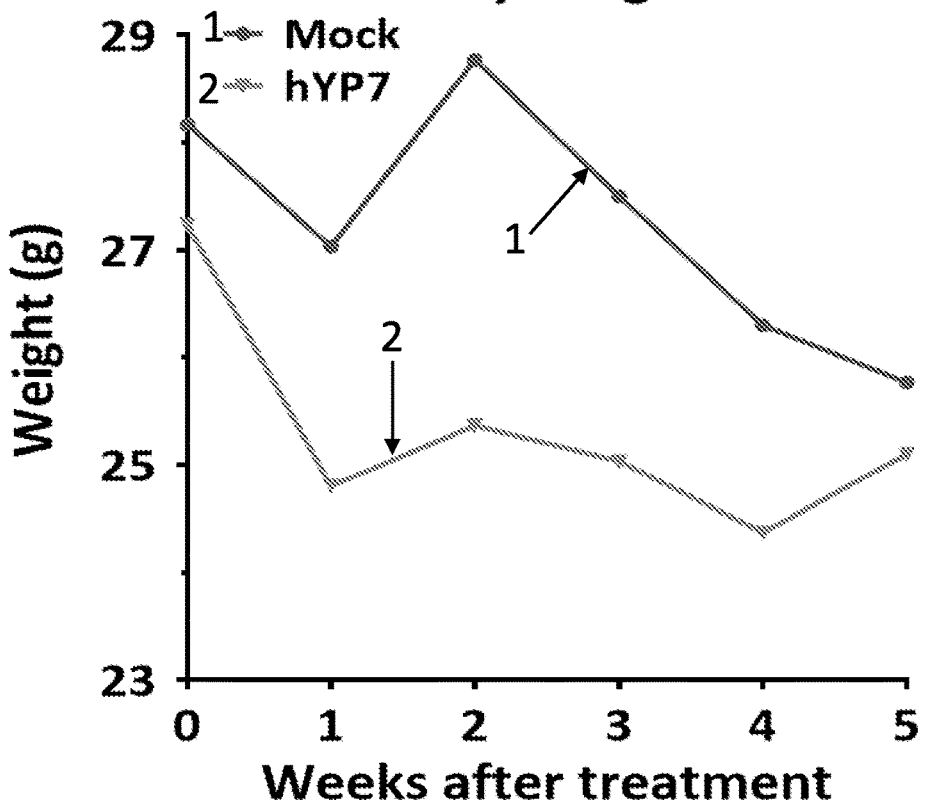

The efficacy of CAR (hYP7) T cells was also evaluated in the HepG2 peritoneal dissemination xenograft mouse model. NSG mice were intraperitoneally injected with luciferase-expressing HepG2 cells (HepG2-luc), followed 12 days later by 20 million CAR (hYP7) T cells (FIG. 15A). As shown in FIG. 15B and FIG. 15C, CAR (hYP7) T cells reduced tumor burden to background levels, with tumor flux much lower than in mice treated with mock T cells on day 21, further demonstrating superior antitumor efficacy of CAR (hYP7) T cells. Mice treated with CAR (hYP7) T cells had a transient decrease in body weight that returned to baseline levels and remained stable thereafter (FIG. 19B), consistent with a transient cytokine release syndrome. After five weeks of CAR (hYP7) T cell treatment, ddPCR detected 35.6% and 19.5% of CAR expression in genomic DNAs from tumor and mouse spleen, respectively (FIG. 15D). In contrast, CD19 CAR T cells showed no sign of gene integration in either tissue. Furthermore, human HepG2 cells migrated to mouse liver and CAR (hYP7) T cells restricted the spreading of tumor cells, similar to the observation in the Hep3B peritoneal xenograft mouse model.

Figure 16A:
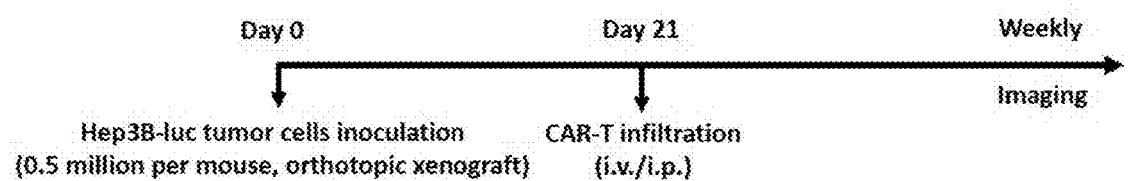
FIGS. 16A-16D show HCC eradication in the Hep3B orthotopic xenograft mouse model by CAR (hYP7) T cells.
Figure 16B:
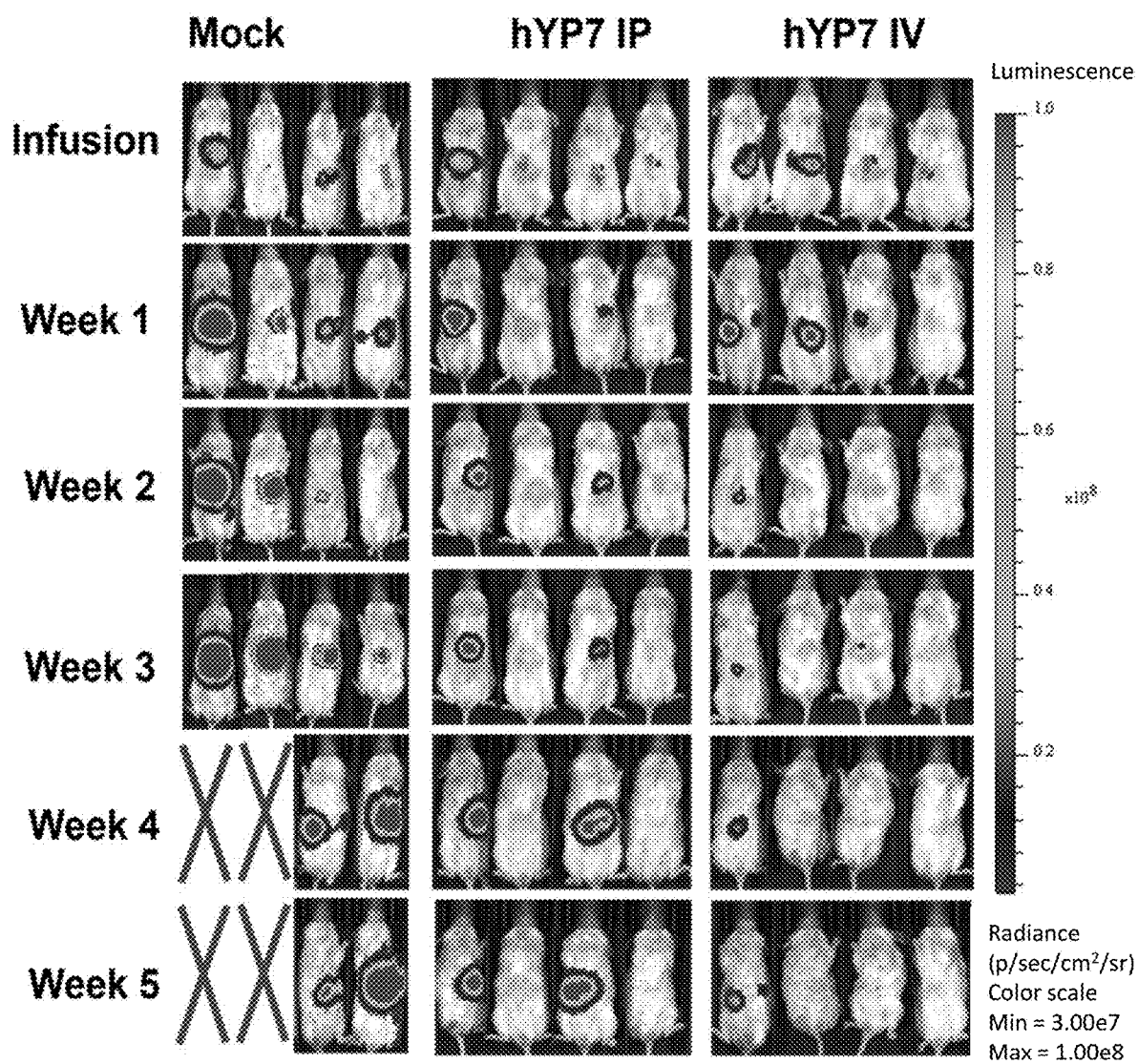
Figure 16C:
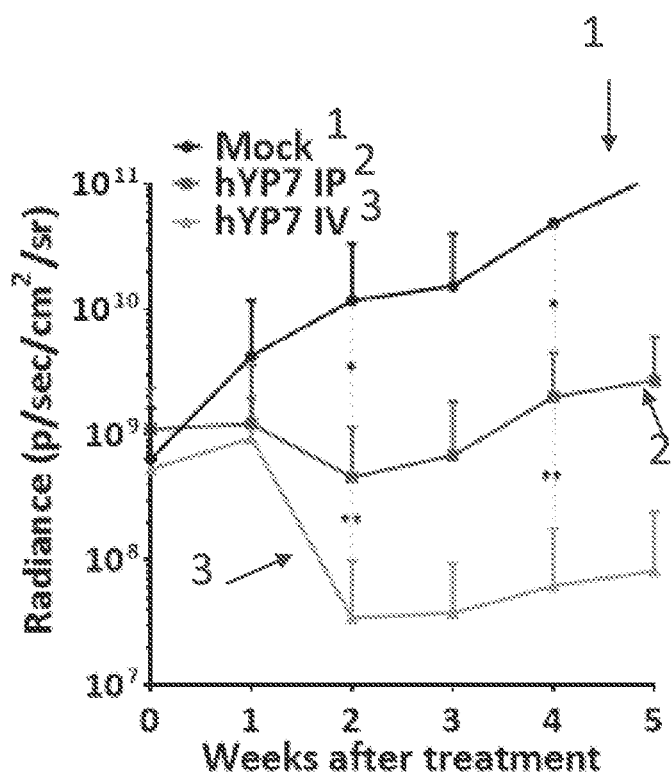
Figure 16D:
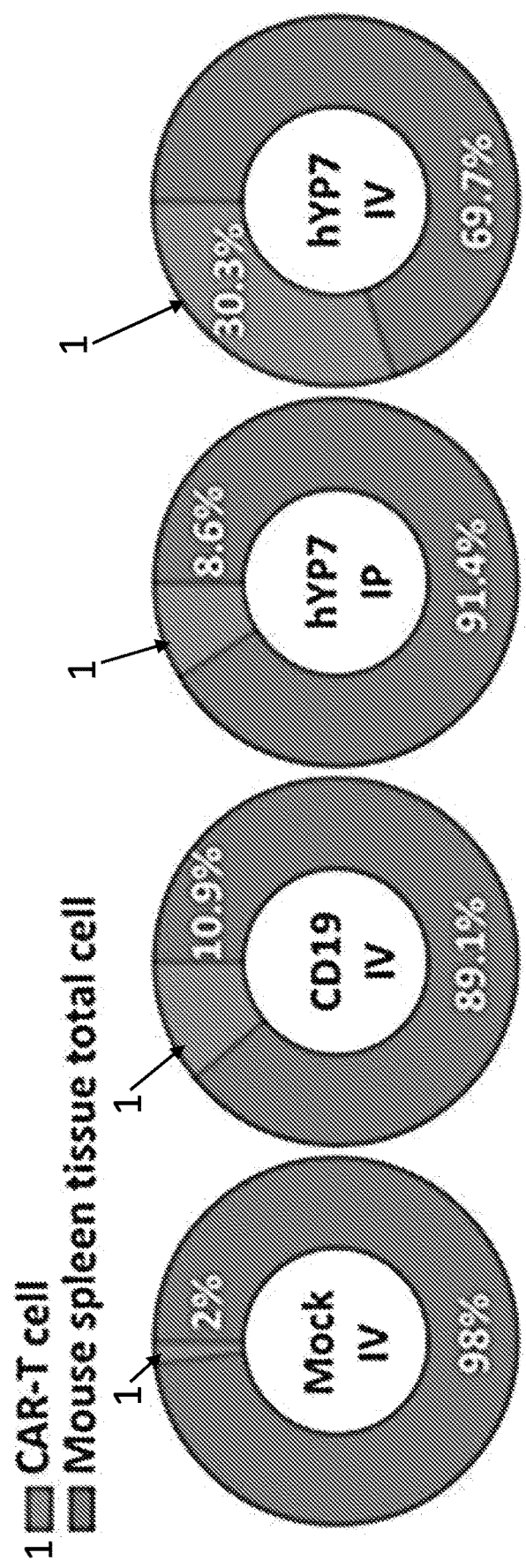
Figure 17A:
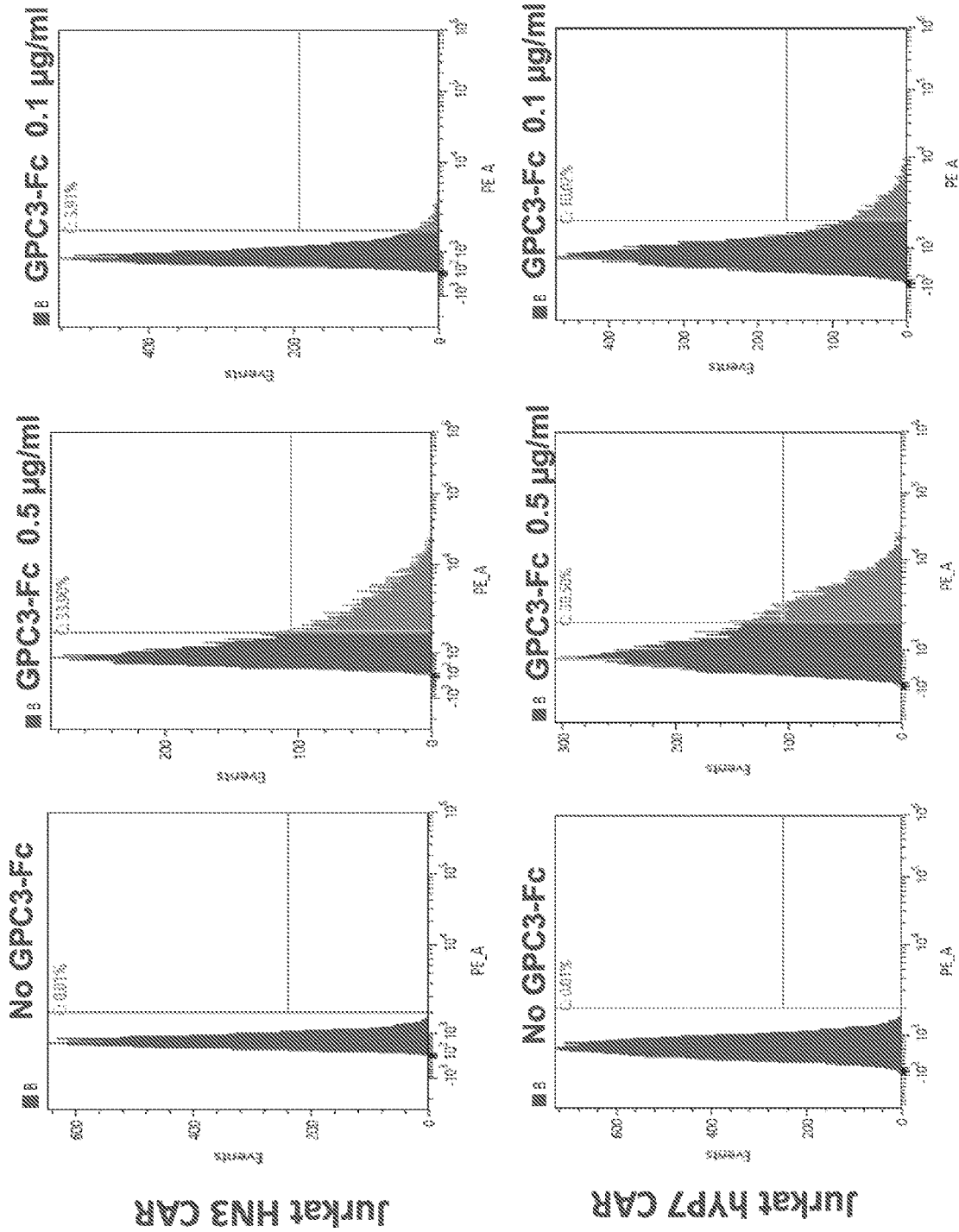
FIGS. 17A-17B are a series of flow cytometry plots (FIG. 17A) and Scatchard plots (FIG. 17B) showing binding of GPC3-targeted (HN3 and hYP7) Jurkat CAR T cells to GPC3-human Fc (hFc) fusion protein.
Figure 17B:
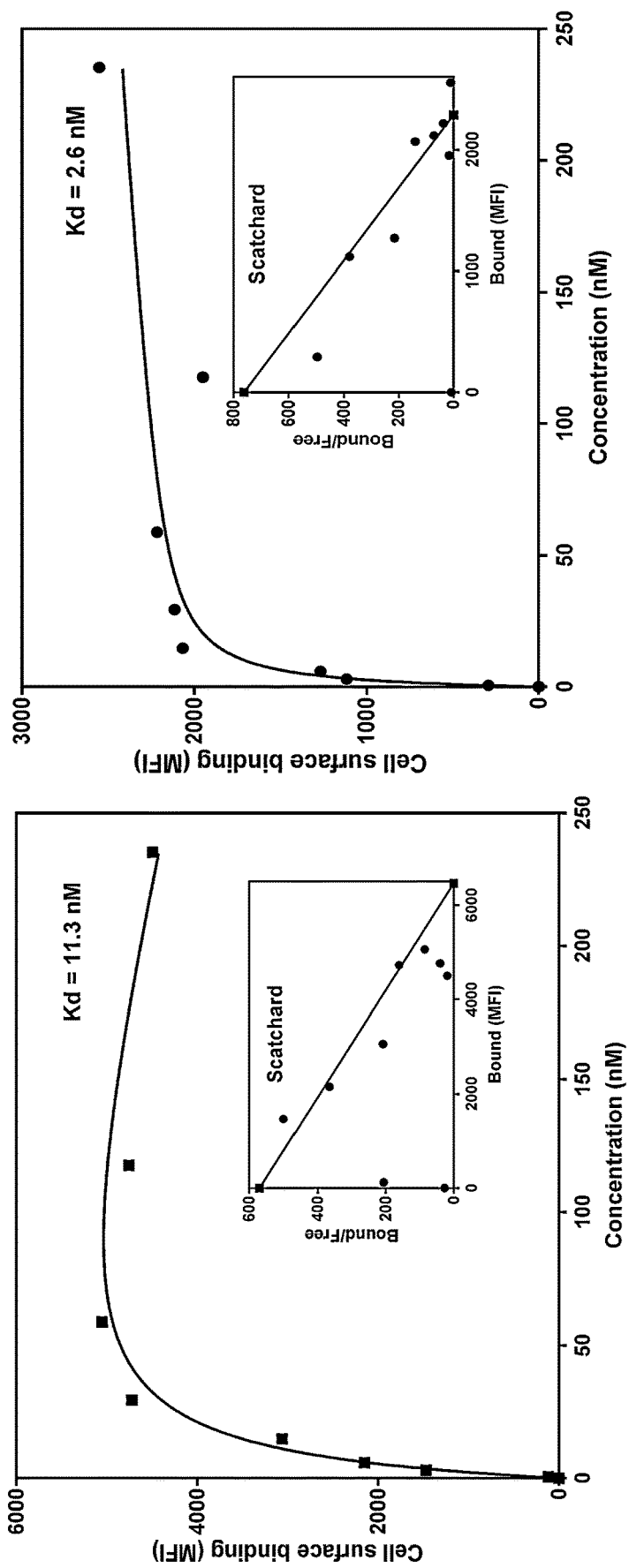

The antitumor activity of CAR (hYP7) T cells was further examined in an orthotopic HCC mouse model as it is more clinical relevant. Half million Hep3B-luc cells were injected into the liver of NSG mice, and tumor engraftment was confirmed by bioluminescent imaging (FIG. 16A). At day 21, CAR (hYP7) T cells were intraperitoneally or intravenously infused into mice. Although both routes of administration of CAR (hYP7) T cells led to a reduction in tumor size and significantly suppressed tumor growth when compared to the control group, intravenous injection of CAR T cells (hYP7 IV) resulted in greater tumor regression than peritoneal injection of CART cells (hYP7 IP) in mice (FIGS. 16B-16C). At the end of this study, 3 out of 4 mice in the hYP7 IV group were liver tumor free, whereas all mice in the mock T cell group carried large tumors. As shown in FIG. 16D, five weeks after CAR T cell infusion, 30.3% of CAR was detected in mouse spleen from hYP7 IV group, only 8.6% of CAR existed in mouse spleen from hYP7 IP group, which was consistent with antitumor efficacy of each route of administration in mice. Moreover, the luminescence imaging demonstrated that Hep3B cells grew in mouse liver, and infusion of CAR (hYP7) T cells either dramatically suppressed tumor growth or completely eliminated tumor cells in mice. Last, toxicology studies were performed to evaluate side effects of CAR (hYP7) T cell treatment. Mice in the hYP7 intravenous group showed increases in white blood cells and neutrophils, which can be involved in rapid immune response in vivo (Table 8). In addition, alanine aminotransferase (ALT) activity was elevated in one mouse receiving CAR (hYP7) T cells via tail vein; however, no gross evidence of liver damage was found following mouse necropsy. All organ weights of the treated mice were similar to those of the control group, except for the lung. No significant differences were detected in any other parameters measured. Taking together, these results demonstrate that CAR (hYP7) T cells can induce complete regression of HCC tumors in mice.

TABLE 8

Toxicity of CAR (hYP7) T cells in Hep3B orthotopic xenograft mice

| | Mouse group | | | | |
| --- | --- | --- | --- | --- | --- |
| | Mock | hYP7 IP | hYP7 IV | hYP7 IV | Normal |
| | | | Mouse ID | | |
| | #807 | #765 | #793 | #773 | Values |
| Parameters | | | | | |
| White blood cells (K/µl) | 2.24 | 1.78 | 5.68 | 11.06 | 1.80-10.70 |
| Red blood cells (M/µl) | 9.11 | 8.1 | 9.56 | 8.03 | 6.36-9.42 |
| Neutrophils (K/µl) | 2.0 | 1.29 | 4.98 | 6.13 | 0.10-2.40 |
| Albumin (g/dL) | 4.1 | 3.8 | 3.7 | 3.6 | 2.5-4.8 |
| Alkaline phosphatase (U/L) | 70 | 41 | 73 | 88 | 62-209 |
| Alanine aminotransferase (U/L) | 37 | 34 | 56 | 297 | 28-132 |
| Total bilirubin (mg/dL) | 0.3 | 0.3 | 0.3 | 0.2 | 0.1-0.9 |
| Creatinine (mg/dL) | 0.6 | 0.4 | 0.2 | 0.3 | 0.2-0.8 |
| Globulin (g/dL) | 1.3 | 1.4 | 1 | 1.1 | 0.0-0.6 |
| Total protein (g/dL) | 5.5 | 5.2 | 4.7 | 4.7 | 3.6-6.6 |
| Blood urea nitrogen (mg/dL) | 14 | 18 | 28 | 23 | 18-29 |
| Select organ weight (g) | | | | | |
| Brain | 0.497 | 0.519 | 0.459 | 0.46 | |
| Heart | 0.106 | 0.138 | 0.088 | 0.102 | |
| Kidney | 0.248 | 0.336 | 0.236 | 0.293 | |

TABLE 8-continued

Toxicity of CAR (hYP7) T cells in Hep3B orthotopic xenograft mice

| | Mouse group | | | | |
|---|---|---|---|---|---|
| | Mock | hYP7 IP | hYP7 IV | hYP7 IV | Normal |
| | | Mouse ID | | | |
| | #807 | #765 | #793 | #773 | Values |
| Liver | 1.315 | 1.378 | 0.71 | 0.933 | |
| Lung | 0.187 | 0.245 | 0.254 | 0.316 | |
| Spleen | 0.041 | 0.119 | 0.035 | 0.055 | |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A nucleic acid molecule encoding a chimeric antigen receptor (CAR), comprising in the 5' to 3' direction:
   a nucleic acid encoding a first granulocyte-macrophage colony stimulating factor receptor signal sequence (GMCSFRss);
   a nucleic acid encoding a tumor antigen-specific antibody or antigen-binding fragment thereof, wherein (1) the tumor antigen is glypican-3 (GPC3) and the nucleic acid encoding the GPC3-specific antibody or antigen-binding fragment comprises the variable heavy (VH) domain complementarity determining region 1 (CDR1), CDR2 and CDR3 nucleic acid sequences of SEQ ID NO: 25 and the variable light (VL) domain CDR1, CDR2 and CRR3 nucleic acid sequences of SEQ ID NO: 27; or (2) the tumor antigen is mesothelin and the nucleic acid encoding the mesothelin-specific antibody or antigen-binding fragment comprises the VH domain CDR1, CDR2 and CDR3 nucleic acid sequences of SEQ ID NO: 37 and the VL domain CDR1, CDR2 and CDR3 nucleic acid sequences of SEQ ID NO: 39;
   a nucleic acid encoding an extracellular hinge region;
   a nucleic acid encoding a transmembrane domain;
   a nucleic acid encoding an intracellular co-stimulatory domain;
   a nucleic acid encoding an intracellular signaling domain;
   a nucleic acid encoding a self-cleaving 2A peptide;
   a nucleic acid encoding a second GMCSFRss; and
   a nucleic acid encoding a truncated human epidermal growth factor receptor (huEGFRt).

2. The nucleic acid molecule of claim 1, wherein:
   the extracellular hinge region comprises a CD8a hinge region or a CD28 hinge region.

3. The nucleic acid molecule of claim 1, wherein the extracellular hinge region comprises a CD8a hinge region, the transmembrane domain comprises a CD8a transmembrane domain, the intracellular co-stimulatory domain comprises a 4-1BB co-stimulatory domain and the intracellular signaling domain comprises a CD3ζ signaling domain.

4. The nucleic acid molecule of claim 3, wherein:
   the nucleic acid encoding the CD8a hinge comprises the sequence of SEQ ID NO: 3.

5. The nucleic acid molecule of claim 1, wherein:
   the nucleic acid encoding the first GMCSFRss and the nucleic acid encoding the second GMCSFRss each comprise the sequence of SEQ ID NO: 1.

6. The nucleic acid molecule of claim 1, further comprising a human elongation factor 1α (EF1α) promoter sequence 5' of the nucleic acid encoding the first GMCSFRss.

7. The nucleic acid molecule of claim 1, wherein the antigen-binding fragment is a single-chain variable fragment (scFv).

8. The nucleic acid molecule of claim 1, wherein the tumor antigen is GPC3 and the nucleic acid encoding the GPC3-specific antibody or antigen-binding fragment comprises the VH domain CDR1, CDR2 and CDR3 nucleic acid sequences of SEQ ID NO: 25 and the VL domain CDR1, CDR2 and CDR3 nucleic acid sequences of SEQ ID NO: 27.

9. The nucleic acid molecule of claim 1, wherein the tumor antigen is GPC3, and wherein:
   the VH domain CDR1, CDR2 and CDR3 nucleic acid sequences respectively comprise nucleotides 91-105, 148-204 and 301-318 of SEQ ID NO: 25 and the VL domain CDR1, CDR2 and CDR3 nucleic acid sequences respectively comprise nucleotide 70-120, 166-186 and 283-309 of SEQ ID NO: 27.

10. The nucleic acid molecule of claim 9, wherein the nucleic acid encoding the GPC3-specific antibody-binding fragment comprises the sequence of nucleotides 73-807 of SEQ ID NO: 15.

11. A vector comprising the nucleic acid molecule of claim 1.

12. The vector of claim 11, wherein the vector is a viral vector.

13. The vector of claim 12, wherein the viral vector is a lentiviral vector.

14. An isolated host cell comprising the vector of claim 11.

15. A method of treating a GPC3-positive cancer in a subject, comprising administering to the subject a therapeutically effective amount of an isolated host cell comprising the nucleic acid molecule of claim 1, wherein the tumor antigen-specific antibody or antigen-binding fragment is a GPC3-specific antibody or antigen-binding fragment.

16. The method of claim 15, wherein the GPC3-positive cancer is a hepatocellular carcinoma (HCC), melanoma, ovarian clear-cell carcinoma, yolk sac tumor (YST), neuroblastoma, hepatoblastoma or Wilms' tumor.

17. A method of treating a mesothelin-positive cancer in a subject, comprising administering to the subject a therapeutically effective amount of an isolated host cell comprising the nucleic acid molecule of claim 1, wherein the tumor antigen-specific antibody or antigen-binding fragment is a mesothelin-specific antibody or antigen-binding fragment.

18. The method of claim 17, wherein the mesothelin-positive cancer is a mesothelioma, prostate cancer, lung cancer, stomach cancer, squamous cell carcinoma, pancreatic cancer, cholangiocarcinoma, triple negative breast cancer or ovarian cancer.

19. The method of claim 15, wherein the isolated host cells are T lymphocytes or natural killer (NK) cells.

20. The method of claim 19, wherein the T lymphocytes are autologous T lymphocytes or allogeneic T lymphocytes.

21. The method of claim 17, wherein the isolated host cells are T lymphocytes or natural killer (NK) cells.

22. The method of claim 21, wherein the T lymphocytes are autologous T lymphocytes or allogeneic T lymphocytes.

23. The nucleic acid molecule of claim 1, wherein the tumor antigen is GPC3, and wherein the VH domain CDR1, CDR2 and CDR3 nucleic acid sequences respectively comprise nucleotides 76-99, 151-180 and 295-318 of SEQ ID NO: 25 and the VL domain CDR1, CDR2 and CDR3 nucleic acid sequences respectively comprise nucleotides 79-114, 166-174 and 283-309 of SEQ ID NO: 27.

24. The nucleic acid molecule of claim 1, wherein the tumor antigen is GPC3, and wherein the nucleic acid encoding the GPC3-specific antibody-binding fragment comprises the VH domain nucleic acid sequence of SEQ ID NO: 25 and the VL domain nucleic acid sequence of SEQ ID NO: 27.

25. The nucleic acid molecule of claim 1, wherein the tumor antigen is mesothelin and the nucleic acid encoding the mesothelin-specific antibody or antigen-binding fragment comprises the VH domain CDR1, CDR2 and CDR3 nucleic acid sequences of SEQ ID NO: 37 and the VL domain CDR1, CDR2 and CDR3 nucleic acid sequences of SEQ ID NO: 39.

26. The nucleic acid molecule of claim 1, wherein the tumor antigen is mesothelin, and wherein the VH domain CDR1, CDR2 and CDR3 nucleic acid sequences respectively comprise nucleotides 91-108, 101-204 and 298-336 of SEQ ID NO: 37 and the VL domain CDR1, CDR2 and CDR3 nucleic acid sequences respectively comprise nucleotides 70-102, 148-168 and 265-303 of SEQ ID NO: 39.

27. The nucleic acid molecule of claim 1, wherein the tumor antigen is mesothelin, and wherein the VH domain CDR1, CDR2 and CDR3 nucleic acid sequences respectively comprise nucleotides 79-102, 154-177 and 292-336 of SEQ ID NO: 37 and the VL domain CDR1, CDR2 and CDR3 nucleic acid sequences respectively comprise nucleotides 79-96, 148-156 and 265-303 of SEQ ID NO: 39.

28. The nucleic acid molecule of claim 1, wherein the tumor antigen is mesothelin, and wherein the nucleic acid encoding the mesothelin-specific antibody-binding fragment comprises the VH domain nucleic acid sequence of SEQ ID NO: 37 and the VL domain nucleic acid sequence of SEQ ID NO: 39.

29. The nucleic acid molecule of claim 1, wherein the transmembrane domain comprises a CD8a transmembrane domain or a CD28 transmembrane domain.

30. The nucleic acid molecule of claim 1, wherein the intracellular co-stimulatory domain comprises a 4-1BB, CD28, ICOS, OX40, CD27 or DAP10 co-stimulatory domain.

31. The nucleic acid molecule of claim 1, wherein the intracellular signaling domain comprises a CD3ζ or an FcεRIγ signaling domain.

32. The nucleic acid molecule of claim 3, wherein the nucleic acid encoding the CD8α transmembrane domain comprises the sequence of SEQ ID NO: 5.

33. The nucleic acid molecule of claim 3, wherein the nucleic acid encoding the 4-1BB co-stimulatory domain comprises the sequence of SEQ ID NO: 7.

34. The nucleic acid molecule of claim 3, wherein the nucleic acid encoding the CD3ζ signaling domain comprises the sequence of SEQ ID NO: 9.

35. The nucleic acid molecule of claim 1, wherein the self-cleaving 2A peptide is a T2A peptide and the nucleic acid encoding the self-cleaving 2A peptide comprises the sequence of SEQ ID NO: 11.

36. The nucleic acid molecule of claim 1, wherein the nucleic acid encoding the huEGFRt comprises the sequence of SEQ ID NO: 13.

\* \* \* \* \*